US010107770B2

(12) United States Patent
Weindorf et al.

(10) Patent No.: US 10,107,770 B2
(45) Date of Patent: Oct. 23, 2018

(54) PORTABLE APPARATUS FOR SOIL CHEMICAL CHARACTERIZATION

(71) Applicants: Texas Tech University System, Lubbock, TX (US); Ramakrishna Mission Vivekananda University, West Bengal (IN)

(72) Inventors: David Weindorf, Lubbock, TX (US); Somsubhra Chakraborty, West Bengal (IN)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 0 days.

(21) Appl. No.: 15/319,816

(22) PCT Filed: Jun. 18, 2015

(86) PCT No.: PCT/US2015/036537
§ 371 (c)(1),
(2) Date: Dec. 19, 2016

(87) PCT Pub. No.: WO2015/195988
PCT Pub. Date: Dec. 23, 2015

(65) Prior Publication Data
US 2017/0122889 A1 May 4, 2017

Related U.S. Application Data

(60) Provisional application No. 62/013,692, filed on Jun. 18, 2014.

(51) Int. Cl.
*G01N 23/22* (2018.01)
*G01N 33/24* (2006.01)
(Continued)

(52) U.S. Cl.
CPC ....... *G01N 23/2206* (2013.01); *G01N 21/359* (2013.01); *G01N 21/3563* (2013.01);
(Continued)

(58) Field of Classification Search
CPC ............. G01N 21/359; G01N 21/3563; G01N 23/2206; G01N 23/223; G01N 33/24
See application file for complete search history.

(56) References Cited

U.S. PATENT DOCUMENTS 5,306,909 A * 4/1994 Jones ................. G01N 21/3577
250/255
2007/0003008 A1 * 1/2007 Warner ................ G01N 23/223
378/44
(Continued)

OTHER PUBLICATIONS

Andersson et al. Determination of bromine, chlorine, sulphur and phosphorus in peat by X-ray fluorescence spectrometry combined with single-element and multi-element standard addition. Talanta 37(2): 185-191. 1990.*
(Continued)

*Primary Examiner* — Dominic J Bologna
(74) *Attorney, Agent, or Firm* — Daniel J. Chalker; Edwin S. Flores; Chalker Flores, LLP

(57) ABSTRACT

The present invention determines one or more properties of a soil sample by scanning a soil sample using a visible near infrared diffuse reflectance (VisNIR) spectroradiometer, scanning the soil sample using a x-ray fluorescence (PXRF) spectrometer, receiving a diffuse reflectance spectra from the VisNIR spectroradiometer and an elemental data from the PXRF spectrometer, determining one or more properties of the soil sample using one or more processors and a predictive model that relates the diffuse reflectance spectra and the elemental data to the one or more properties, and providing the one or more properties of the soil sample to one or more input/output interface.

38 Claims, 39 Drawing Sheets

(51) Int. Cl.
  G01N 21/3563    (2014.01)
  G01N 21/359     (2014.01)
  G01N 23/223     (2006.01)
  G01N 23/2206    (2018.01)

(52) U.S. Cl.
  CPC ........... *G01N 23/223* (2013.01); *G01N 33/24* (2013.01); *G01N 2201/10* (2013.01); *G01N 2201/12* (2013.01); *G01N 2223/071* (2013.01); *G01N 2223/33* (2013.01); *G01N 2223/616* (2013.01)

(56) References Cited

U.S. PATENT DOCUMENTS

| | | | | |
|---|---|---|---|---|
| 2013/0191046 | A1* | 7/2013 | Henning | G01N 11/04 702/50 |
| 2015/0347647 | A1* | 12/2015 | Osborne | B09C 1/002 703/6 |

OTHER PUBLICATIONS

White, et al., "Infrared characterization of water and hydroxyl ion in the basic magnesium carbonate minerals." American Mineralogist, Jan.-Feb. 1971, vol. 56, pp. 46-53.

Williams, P.C., "Variables affecting near-infrared reflectance spectroscopic analysis." In:Williams, P., Norris, K., (Eds.), Near-infrared technology in the agricultural and food industries. Am. Assoc. of Cereal Chemists, St. Paul, MN, 1987, pp. 143-167.

Zhu, et al., "Characterizing soils using a portable X-ray fluorescence spectrometer: 1. Soil texture." Geoderma, 2011, vol. 167-168, pp. 167-177.

International Search Report and Written Opinion [PCT/US15/036537] dated Oct. 2, 2015.

Alavi Panah, et al., "Relationship Between the Landsat TM, MSS DATA and Soil Salinity." Journal of Agricultural Science and Technology, 2001, vol. 3, pp. 21-31.

Aldabaa, et al., "Combination of proximal and remote sensing methods for rapid soil salinity quantification." Geoderma, 2015, vol. 239-240, pp. 34-46.

Andrews, et al., "The Soil Management Assessment Framework: A Quantitative Soil Quality Evaluation Method." Soil Science Society of America Journal, Nov. 2004, vol. 68, No. 6, pp. 1945-1962.

Argyraki, et al., "Evaluation of Portable X-ray Fluorescence Instrumentation for in situ Measurements of Lead on contaminated Land." Analyst, Aug. 1997, vol. 122, pp. 743-749.

Barnes, et al., "Standard Normal Variate Transformation and Detrending of Near-Infrared Diffuse Reflectance Spectra." Applied Spectroscopy, May 1989, vol. 43, No. 5, pp. 772-777.

Bilgili, et al., "The Use of Hyperspectral Visible and Near Infrared Reflectance Spectroscopy for the Characterization of Salt-Affected Soils in the Harran Plain, Turkey." Arid Land Research and Management, Jan. 2011, vol. 25, No. 1, pp. 19-37.

Box, et al., "An Analysis of Transformations." Journal of the Royal Statistical Society, Jan. 1964, vol. 26, No. 2, pp. 211-252.

Brady, N.C. et al., "The nature and properties of soils." 14th Ed. Prentice Hall, Upper Saddle River, NJ., 2008, pp. 975.

Brown, et al., "Validation requirements for diffuse reflectance soil characterization models with a case study of VNIR soil C prediction in Montana." Geoderma, 2005, vol. 129, pp. 251-267.

Buddenbaum, et al., "The Effects of Spectral Pretreatments on Chemometric Analyses of Soil Profiles Using Laboratory Imaging Spectroscopy." Applied and Environmental Soil Science, Oct. 2012, pp. 1-13.

Chakraborty, et al., "Analysis of petroleum contaminated soils by spectral modeling and pure response profile recovery of n-hexane." Environmental Pollution, Jul. 2014, vol. 190, pp. 10-18.

Chakraborty, et al., "Spectral data mining for rapid measurement of organic matter in unsieved moist compost." Applied Optics, Feb. 2013, vol. 52, No. 4, pp. B82-B92.

Chang, et al., "Near-Infrared Reflectance Spectroscopy—Principal Components Regression Analyses of Soil Properties." Science Society of America Journal, 2001, vol. 65, pp. 480-490.

Clark, R.N. et al., "High spectral resolution reflectance spectroscopy of minerals." Journal of Geophysical Research, Aug. 10, 1990, 95 (B8), 12653-12680.

Clay, D.E. et al., "Factors influencing spatial variability of soil apparent electrical conductivity." Communications in Soil Science and Plant Analysis, 2001, 32(19-20), 2993-3008.

Csillag, et al., "Spectral band selection for the characterization of salinity status of soils." Remote Sensing of Environment, Mar. 1993, vol. 43, No. 3, pp. 231-242.

Eldeiry, et al., "Detecting Soil Salinity in Alfalfa Fields using Spatial Modeling and Remote Sensing." Science Society of America Journal, Jan.-Feb. 2008, vol. 72, No. 1, pp. 208-2011.

Farifteh, et al., "Assessing salt-affected soils using remote sensing, solute modelling, and geophysics." Geoderma, Feb. 2006, vol. 130, No. 3, pp. 191-206.

Farifteh, et al., "Quantitative analysis of salt-affected soil reflectance spectra: A comparison of two adaptive methods (PLSR and ANN)." Remote Sensing of Environment, Sep. 2007, vol. 110, No. 1, pp. 59-78.

Haaland, et al., "Partial least-squares methods for spectral analyses. 1. Relation to other quantitative calibration methods and the extraction of qualitative information." Analytical Chemistry, Jun. 1988, vol. 60, pp. 1193-1202.

Hu, et al., "Metals Analysis of Agricultural Soils via Portable X-ray Fluorescence Spectrometry." Bulletin of environmental contamination and toxicology, 2014, vol. 92, pp. 420-426.

Ji, J.F. et al., "Rapid and quantitative measurement of hematiteand goethite in the Chinese loess-paleosol sequence by diffuse reflectancespectroscopy." Clays and Clay Minerals, 2002 50 (2), 208-216.

Jones, A.A., "Methods of Soil Analysis—Part 2: Chemical and Microbiological Properties." Soil Science Society of America, Madison, WI. 1982.

Kalra, N.K. et al., "Potentiality of Landsat, SPOT and IRS satellite imagery, for recognition of salt affected soils in Indian Arid Zone." International J.of Remote Sensing, 1996, 17(15), 3001-3014.

Karlen, et al., "A preliminary watershed scale soil quality assessment in north central Iowa, USA." Soil & Tillage Research, Jun. 2008, vol. 99, No. 2, pp. 291-299.

Khan,et al., "Mapping salt-affected soils using remote sensing indicators—a simple approach with the use of GIS IDRISI." Paper presented at the 22nd Asian Conference on Remote Sensing., Nov. 2001, vol. 5, pp. 1-5.

Liu, et al., "Feasibility of Estimating Cu Contamination in Floodplain Soils using VNIR Spectroscopy—A Case Study in the Le'an River Floodplain, China." Soil and Sediment Contamination: An International Journal, 2012, vol. 21, No. 8, pp. 951-969.

Martens, H. et al., "Multivariate Calibration" Wiley, New York, USA. 1989.

Pozdnyakova, et al., "Geostatistical analyses of soil salinity in a large field." Precision Agriculture, Sep. 1999, vol. 1, No. 2, pp. 153-165.

Rhoades, et al., "Soil Salinity Assessment: Methods and interpretation of electrical conductivity measurements." Food and Agricultural Organization, 1999, BOOK.

Saeys, et al., "Potential for Onsite and Online Analysis of Pig Manure using Visible and Near Infrared Reflectance Spectroscopy." Biosystems Engineering, 2005, vol. 91, No. 4, pp. 393-402.

Shacklette, et al., "Element Concentrations in Soils and Other Surficial Materials of the Conterminous United States." U.S. Geological Survey Professional Paper 1270, 1984, pp. 1-16.

Soil Salinity Staff, "Diagnosis and improvement of saline and alkali soils." USDA Agricultural Handbook, Feb. 1954, No. 60.

Soil Survey Staff, "Land resource regions and major land resource areas of the United States, the Caribbean, and the Pacific Basin." United States Department of Agriculture Handbook 296, 2006. BOOK.

Soil Survey Staff, 2014a. Official soil series descriptions. USDA-NRCS. Available online at https://soilseries.sc.egov.usda.gov/osdname. asp (verified Mar. 10, 2014).

(56) References Cited

OTHER PUBLICATIONS

Soil Survey Staff, 2014b. Web soil survey. USDA-NRCS. Available online at http://websoilsurvey.sc.egov.usda.gov/App/HomePage.htm (verified Apr. 21, 2014).
Sonmez, et al., "Assessment of different soil to water ratios (1:1, 1:2.5, 1:5) in soil salinity studies." Geoderma, 2008, vol. 144, pp. 361-369.
Swanhart, "Measuring soluble salts in soils via portable x-ray fluorescence spectrometry." Master's Thesis, Doctoral dissertation, University of Florida, Dec. 2013, pp. 1-72.
Tamás, J. et al., "Analysis of a small agricultural watershed using remote sensing techniques." International J. of Remote Sensing, Sep. 10, 2006, 27(17), 3727-3738.
United State Geological Survey (USGS), 2014a. Frequently asked questions about the Landsat missions. Available online at http://landsat.usgs.gov/band_designations_landsat_satellites.php (verified Apr. 21, 2014).
United States Geological Survey (USGS), 2014b. Earth explorer. Available at http://earthexplorer.usgs.gov (verified Apr. 21, 2014).
Van der Voet, H., "Comparing the predictive accuracy of models using a simple randomisation test." Chemometrics and Intelligent Laboratory Systems, 1994, 25, 313-321.
Viscarra Rossel, et al., "Visible, near infrared, mid infrared or combined diffuse reflectance spectroscopy for simultaneous assessment of various soil properties." Geoderma, 2006, vol. 131, pp. 59-75.
Adeniyi, A.A. et al. "Determination of total petroleum hydrocarbons and heavy metals in soils within the vicinity of facilities handling refined petroleum products in Lagos metropolis." Environ. Int. Volume 28, Issues 1-2, Apr. 2002, pp. 79-82.
An, X. et al. "A portable soil nitrogen detector based on NIRS" Precis. Agric. Feb. 2014, vol. 15, Issue 1, pp. 3-16.
Balabin, R.M., et al., "Capabilities of near infrared spectroscopy forthe determination of petroleum macromolecule content in aromatic solutions." J. Near Infrared Spectrosc. 2007, 15, 343-349.
Batjes, N.H., 1996. "Total carbon and nitrogen in the soils of the world." Eur. J. Soil Sci. 1996, 47, 151-163.
Bellon-Maurel, V. et al. Critical reviews of chemometric indicators commonly used for assessing the quality of the prediction of soil attributes by NIR spectroscopy. Trends Anal. Chem. vol. 29, Issue 9, Oct. 2010, pp. 1073-1081.
Bishop, J.L. et al. "Infrared spectroscopic analyses on the nature of water in montmorillonite." Clay Clay Miner. 1994, 42, 702-716.
Breiman, L. "Random forests". Mach. Learn. Jan. 2001, 45, 5-32.
Bricklemyer, R.S. et al. "On-the-go VisNIR: potential and limitations for mapping soil clay and organic carbon." Comput. Electron. Agric. vol. 70, Issue 1, Jan. 2010, pp. 209-216.
Brown, D.J. et al. "Global soil characterization with VNIR diffuse reflectance spectroscopy." Geoderma 132 (2006) 273-290.
Brunet, D. et al. "Comparison between predictions of C and N contents in tropical soils using a Vis-NIR spectrometer including a fibre-optic probe versus a NIR spectrometer including a sample transport module." Biosyst. Eng.vol. 100, Issue 3, Jul. 2008, pp. 448-452.
Camilli, R. et al. "Tracking hydrocarbon plume transport and biodegradation at Deepwater Horizon." Science Aug. 19, 2010, 330, 201-204.
Carpenter, S.R. et al. "Nonpoint pollution of surface waters with phosphorus and nitrogen." Ecol. Appl. Aug. 1998, 8, 559-568.
Chakraborty, S. et al. "Rapid estimation of compost enzymatic activity by spectral analysis method combined with machine learning." Waste Manag. (2014) 34, 623-631.
Chakraborty, S., et al. "Assessing spatial variability of soil petroleum contamination using visiblenear infrared diffuse reflectance spectroscopy." J. Environ. Monit. (2012) 14, 2886-2892.
Chakraborty, S. et al. "Spectral reflectance variability from soil physicochemical properties in oil contaminated soils." Geoderma vols. 177-178, May 2012, pp. 80-89.
Chakraborty, S. et al. "Rapid identification of oil contaminated soils using visible near-infrared diffuse reflectance spectroscopy." J. Environ. Qual. (Jul. 2010) 39, 1378-1387.
Chakraborty. S., et al. "Development of a hybrid proximal sensing method for rapid identification of petroleum contaminated soils" Science of the Total Environment 514 (2015) 399-408 407.
Chukwuma, C.S. "Evaluating baseline data for trace elements pH, organic matter content and bulk density in agricultural soils in Nigeria." Water Air Soil Pollut. Jan. 1996, vol. 86, Issue 1-4, pp. 13-34.
Clark, R.N. et al. High spectral resolution reflectance spectroscopy of minerals. J. Geophys. Res. (Aug. 10, 1990) 95(B8), 12653-12680.
Compton, J.E. et al. "Soil nitrogen transformations and the role of light fraction organic matter in forest soils." Soil Biol. Biochem. vol. 34, Issue 7, Jul. 2002, pp. 933-943.
Craswell, E.T. et al. "The role and function of organic matter in tropical soils." Nutr. Cycl. Agroecosyst. (2001) 61, 7-18.
Eilers, P.H.C., et al., "Flexible smoothing with B-spline and penalties(with comments and rejoinder)." Stat. Sci. 1996, 11, 89-121.
Forrester, S., et al., "An infrared spectroscopic test for total petroleum hydrocarbon (TPH) contamination in soils. Proceedings of the 19th World Congress of Soil Science, Soil Solutions for a Changing World, Brisbane, Australia," 2010, Aug. 1-6,25 pp. 13-16.
Friedman, J.H. Greedy function approximation: a gradient boosting machine. Ann. Stat. (2001) 29, 1189-1232.
Fultz, L.M. et al. "Organic carbon dynamics and soil stability in five semiarid agro ecosystems." Agric. Ecosyst. Environ. (2013) 181, 231-240.
Gauch, H.G. et al. "Model evaluation by comparison of model based predictions and measured values." Agron. J. (Nov.-Dec. 2003) 95, 1442-1446.
Ge, Y., et al., "VisNIR spectra of dried ground soils predict properties of soils scanned moist and intact." Geoderma 2014, 221-222, 61-69.
Gogé, F. "Which strategy is best to predict soil properties of a local site from a national Vis-NIR database?" Geoderma (2014) 213, 1-9.
Gondal, M.A. "Detection of heavy metals in Arabian crude oil residue using laser induced breakdown spectroscopy." Talanta (2006) 69 (5), 1072-1078.
Graham, K.N., "Evaluation of analytical methodologies for diesel fuel contaminants in soil." MS thesis. The University of Manitoba, Canada (Unpublished results). 1998.
Groudeva, V.I., et al., "Bioremediation of waters contaminated with crude oil and toxic heavy metals." Int. J. Miner. Process. 2001, 62, 293-299.
Grujic, S., et al., "Heavy metals in petroleum contaminated surface soils in Serbia." Ann. Chim. 2004, 94 (12), 961-970.
Guyon, I. et al. "Gene selection for cancer classification using SVM." Mach. Learn. (2002) 46, 389-422.
Hewari, J. et al. "Determination of petroleum hydrocarbons in soil: SFE versus Soxhlet andwater effect on recovery." Int. J. Environ. Anal. Chem. (1995) 60, 123-137.
Hoerig, B., et al., "HyMap hyperspectral remote sensing to detect hydrocarbons." Int. J. Remote Sens. 2001, 8, 1413-1422.
Hoylea, F.C. et al. "Temperature and stubblemanagement influence microbial $CO_2$—C evolution and gross N transformation rates." Soil Biol. Biochem. (2006) 38, 71-80.
Hunt, G.R. "Spectral signatures of particulate minerals in the visible and near infrared." Geophysics (Apr. 1977) 42, 501-513.
ISO (International Organisation for Standardisation), 2013. ISO 13196: 2013(E).Soil Quality—Screening Soils for Selected Elements By Energy-Dispersive X-Ray Fluorescence Spectrometry Using a Handheld or Portable Instrument. BSI Standards Publication, London, UK.
Kelly, J.J., et al., "Effects of heavy metals contamination andre mediation on soil microbial communities in the vicinity of a Zinc smelter." J. Environ. Qual. (Feb. 1997) 27, 609-617.
Krivobokova, T. "Theoretical and Practical Aspects of Penalized Spline Smoothing." (Ph.D. dissertation). Aug. 2006 Bielefeld University, Bielefeld, Germany.
Lal, R. et al. "Soil carbon sequestration impacts on global climate change and food security."Science (2004) 304, 1623-1627.

(56) References Cited

OTHER PUBLICATIONS

Kusumo, B.H. et al. "The use of diffuse reflectance spectroscopy for in situ carbon and nitrogen analysis of pastoral soils." Aust. J. Soil Res. (2008) 46, 623-635.

Lang, M. et al. "Land-use type and temperature affect gross nitrogen transformation rates in Chinese and Canadian soils." Plant Soil (2010) 334, 377-389.

Ledley, T.S. et al. "Climate change and greenhouse gases." EOS Trans. Am. Geophys. Union (Sep. 28, 1999) 80, 453-474.

Lobell, D.B. et al. "Moisture effects on soil reflectance." Soil Sci. Soc. Am. J. (2002) 66, 722-727.

Malley, D.F., et al., "Analysis of diesel fuel contamination in soils by near-infrared reflectance spectrometry and solid phase micro extraction—gas chromatography." J. Soil Contam. 1999, 8 (4), 481-489.

Marx, B.D., et al., "Generalized linear regression on sampled signals and curves: a P-spline approach." Technometrics 1999, 41, 1-13.

Massoud, M.S., et al., "Bottom sediments of the Arabian Gulf: II. TPH and TOC contents as indicators of oil pollution and implications for the effect and fate of the Kuwait oil slick." Environ. Pollut. 1996, 93, 27-284.

McCarty, G.W. et al. "Mid-infrared and near-infrared diffuse reflectance spectroscopy for soil carbon measurement." (Mar.-Apr. 2002) Soil Sci. Soc. Am. J. 66, 640-646.

McCarty, G.W., Reeves, J.B., 2006. "Comparison of IR and MIR diffuse reflectance spectroscopy for field-scale measurement of soil fertility parameters." Soil Sci. 171, 94-102.

McDowell, M.L., et al., "Soil total carbon analysis in Hawaiian soils with visible, near-infrared and mid-infrared diffuse reflectance spectroscopy." Geoderma 2012, 189-190, 312-320.

Minasny, B. et al. "Removing the effect of soil moisture from NIR diffuse reflectance spectra for the prediction of soil organic carbon." Geoderma (2011) 167-168, 118-124.

Morgan, C.L.S., et al., "Simulated in situ characterization of soil organic and inorganic carbon with visible near-infrared diffuse reflectance spectroscopy." Geoderma 2009, 151, 249-256.

"Mouazen, A.M., et al., "Online measurement of some selected soil properties using a VIS-NIR sensor." Soil Tillage Res. 2007, 93,13-27."

Mullins, O.C. "The electronic absorption edge of petroleum." Appl. Spectrosc. (1992) 46, 1405-1411.

Muñoz, J.D., et al., "Soil carbon mapping using on-the-go near infrared spectroscopy, topography and aerial photographs." Geoderma 2011, 166, 102-110.

Nelson, D.W., et al., "Total carbon, organic carbon, and organic matter." In: Sparks, D.L. (Ed.), Methods of soil analysis—Part 3: Chemical methods. SSSA,Madison, WI, 1996, pp. 961-1010.

Okparanma, R.N. et al. "Analysis of petroleumcontaminated soils by diffuse reflectance spectroscopy and sequential ultrasonic solvent extraction—gas chromatography." Environ. Pollut. (Jan. 2014) 184, 298-305.

Onianwa, P.C., "Petroleum hydrocarbon pollution of urban top soil in Ibadan City, Nigeria." Environ. Int. 1995, 21, 341-343.

Oren, R. et al. "Soil fertility limits carbon sequestration by forest ecosystems in a CO2 enriched atmosphere." (May 24, 2001) Nature 411, 469-472.

Oyedeji, A.A. et al. "Effect of crude oil-contaminated soil on germination and growth performance of *Abelmoschus asculentus* L. Moench—a widely cultivated vegetable crop in Nigeria." Am. J. Plant Sci. (Oct. 2012) 3, 1451-1454.

Parsons, C. et al. "Quantification of trace arsenic in soils by field-portable X-ray fluorescence spectrometry: considerations for sample preparation and measurement conditions." J. Hazard Mater. (2012) 262, 1213-1222.

"Paulette, L., et al., "Rapid assessment of soiland contaminant variability via portable X-ray fluorescence spectroscopy: Copşa Mică, Romania." Geoderma 2015, 243-244, 130-140."

Reeves III, J. et al. "The potential of diffuse reflectance spectroscopy for the determination of carbon inventories in soils." Environ. Pollut. 116 (2002), S277-S284.

Rossel, R.A.V. et al. "Using data mining to model and interpret soil diffuse reflectance spectra." Geoderma (2010) 158, 46-54.

Sankey, J.B. et al. "Comparing local vs. global visible and near-infrared (VisNIR) diffuse reflectance spectroscopy (DRS) calibrations for the prediction of soil clay, organic C and inorganic C." Geoderma (2008) 148,149-158.

Sarkhot, D.V. "Comparison and detection of total and available soil carbon fractions using visible/near infrared diffuse reflectance spectroscopy." Geoderma (2011) 164, 22-32.

Schwartz, G. et al. "Quantitative analysis of total petroleum hydrocarbons in soils: comparison between reflectance spectroscopy and solvent extraction by 3 certified laboratories." Appl. Environ. Soil Sci. (2012) 1-11.

Selige, T., et al., "High resolution topsoil mapping using hyperspectral image and field data in multivariate regression modeling procedures." Geoderma 2006, 136, 235-244.

Sharma, A., et al., "Characterizing soils via portable X-ray fluorescence spectrometer: 3. Soil reaction (pH)." Geoderma 2014a, 232-234, 141-147.

Sharma, A., et al., "Characterization of soils via portable X-ray fluorescence spectrometer: 4. Cation exchange capacity (CEC)." Geoderma 2014b, 239-240,130-134.

Smith, L.C. et al. "Analysis of environmental and economic damages from British Petroleum's Deepwater Horizon oil spill." Albany Law Rev. (Feb. 22, 2011) 74 (1), 563-585.

"Song, Y., et al., "Diffuse reflectance spectroscopy for monitoring potentially toxic elements in the agricultural soils of Changjiang River Delta, China." Appl. Clay Sci. 2012, 64, 75-83."

Stenberg, B. et al. Chapter five—visible and near infrared spectroscopy in soil science. In: Sparks, D.L. (Ed.), Advances in Agronomy. Academic Press, (2010) pp. 163-215.

Stevens, A. et al. "Measuring soil organic carbon in croplands at regional scale using airborne imaging spectroscopy." Geoderma (2010) 158, 32-45.

Swanhart, S., et al., "Measuring soil salinity via portable X-ray fluorescence spectrometry." Soil Sci. 2015, (Accepted; in press Dec. 5, 2014).

Terhoeven-Urselmans, T., et al., "Usefulness of near-infrared spectroscopy to determine biological and chemical soil properties:importance of sample pre-treatment." Soil Biol. Biochem. 2008, 40 (5), 1178-1188.

Ulmanu, M. et al. "Rapid determination of some heavy metals in soil using an x-ray fluorescence portable instrument." Res. J. Agric. Sci. (Sep. 2011) 43, 235-241.

Vasques, G.M., et al., "Spectroscopic models of soil organic carbon in Florida, USA." J. Environ. Qual. 2010, 39, 923-934.

"Vasques, G.M., et al., "Comparison of multivariate methods for inferential modeling of soil carbon using visible/near-infrared spectra." Geoderma 2008,146, 14-25."

Vasques, G.M. et al. "Modeling of soil organic carbon fractions using visible-near-infrared spectroscopy." Soil Sci. Soc. Am. J. (Jan.-Feb. 2009) 73, 176-184.

Wang, D. et al. "Synthesized use of VisNIR DRS and PXRF for soil characterization: Total carbon and total nitrogen." Geoderma (2015) 243-244, 157-167.

Wang, K., et al., "Predictive mapping of soil total nitrogen at a regional scale: a comparison between geographically weighted regression and cokriging." Appl.Geogr. 2013a, 42, 73-85.

"Wang, S., et al., "Prediction of soil texture using FT-NIR spectroscopy and PXRF spectrometry with data fusion." Soil Sci. 2013b, 178, 626-638."

Weindorf, D.C. et al., "Direct soil gypsum quantification via portable x-ray fluorescence spectroscopy." Soil Sci. Soc. Am. J., Oct. 11, 2013, 77,2071-2077.

Weindorf, D.C. et al. "Use of portable X-ray fluorescence spectrometry for environmental quality assessment of peri-urban agriculture." Environ. Monit. Assess. (2012) 184, 217-227.

Weindorf, D.C., et al, "Evaluation of portable X-ray fluorescence for gypsum quantification in soils." Soil Sci. 2009, 174, 556-562.

(56) References Cited

OTHER PUBLICATIONS

Weindorf, D.C. et al. "Enhanced pedon horizonation using portable Xray fluorescence spectrometry." Soil Sci. Soc. Am. J. (Mar.-Apr. 2012) 76, 522-531.

Weindorf, D.C., et al., "Characterizing soils via portable x-ray fluorescence spectrometer: 2. Spodic and albic horizons." Geoderma 2012c, 189-190, 268-277.

Wiedenbeck, M., 2009. "Field-portable XRF: a geochemist's dream?" Elements 2009, 9, 7-8.

Zhao, Y. et al. "Temporal and spatial variations of nutrients in Baiyangdian Lake, North China." J. Environ. Inf. (Jun. 2011) 17, 102-108.

Zhu, Y. et al., "Determination of soil calcium using field portable15 x-ray fluorescence." Soil Sci. 2009, 174, 151-155.

Zhu, Y., et al., "Characterizing surface soil water with field portable diffuse reflectance spectroscopy." J.Hydrol. 2010, 391, 133-140.

\* cited by examiner

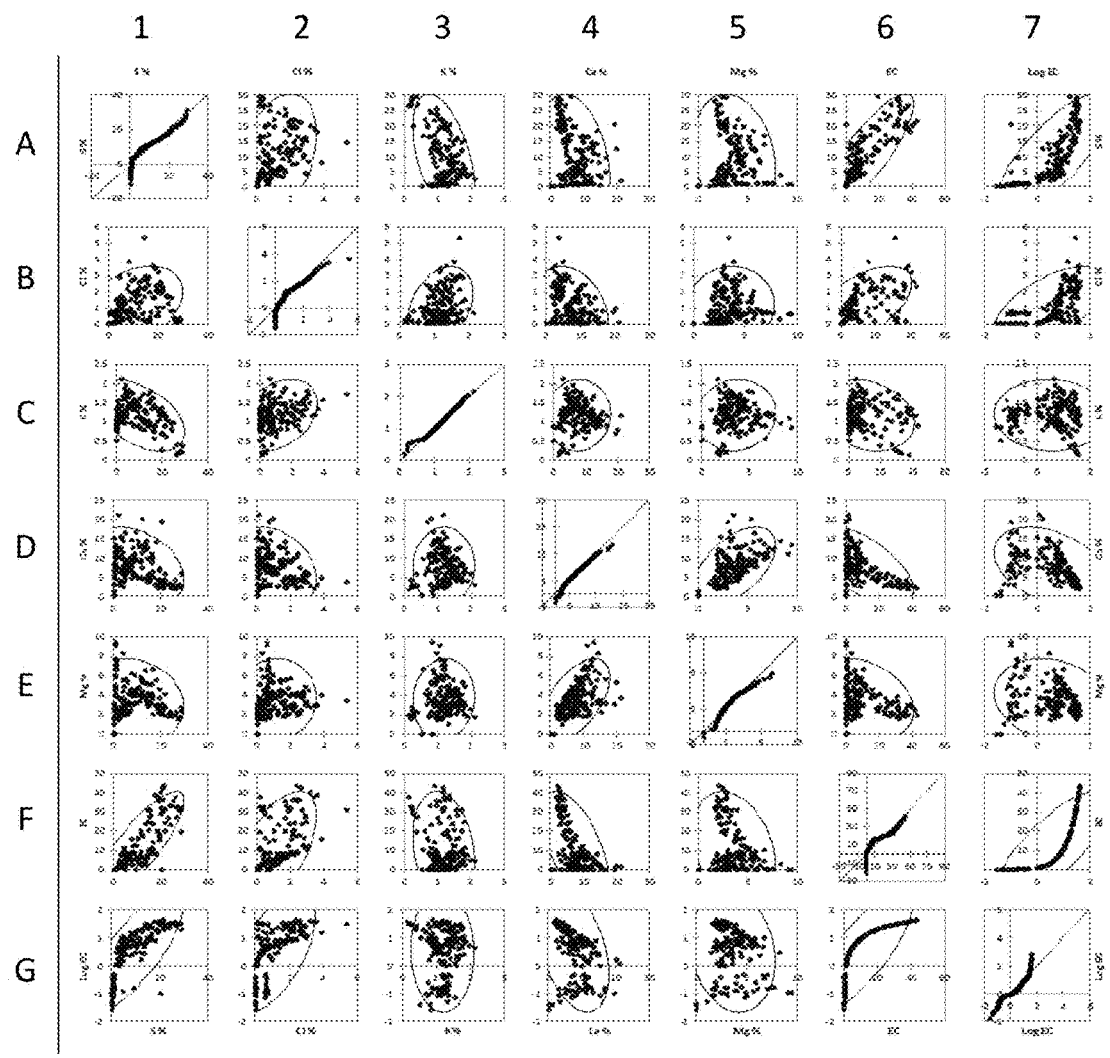
FIGS. 5A1-5G7

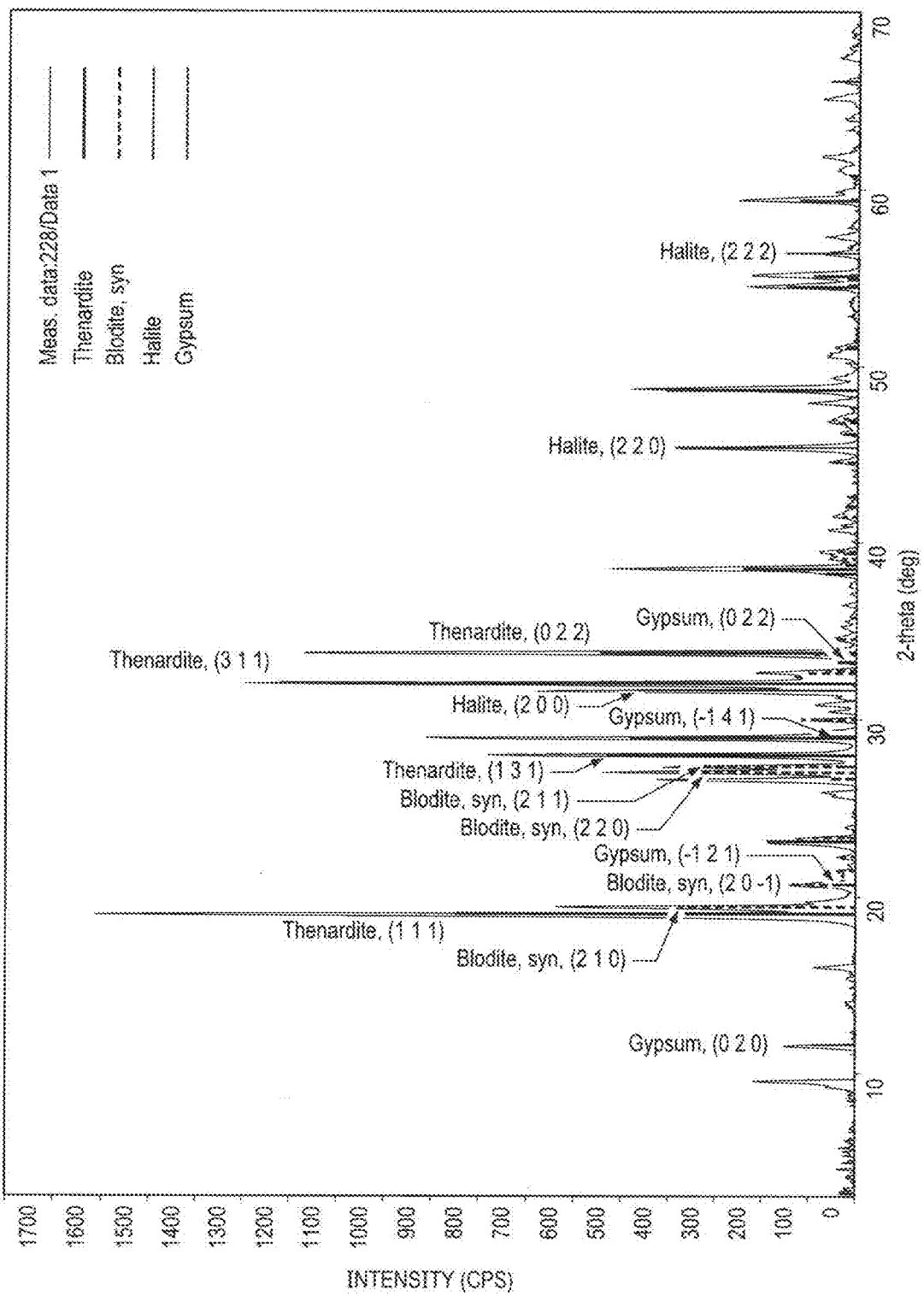

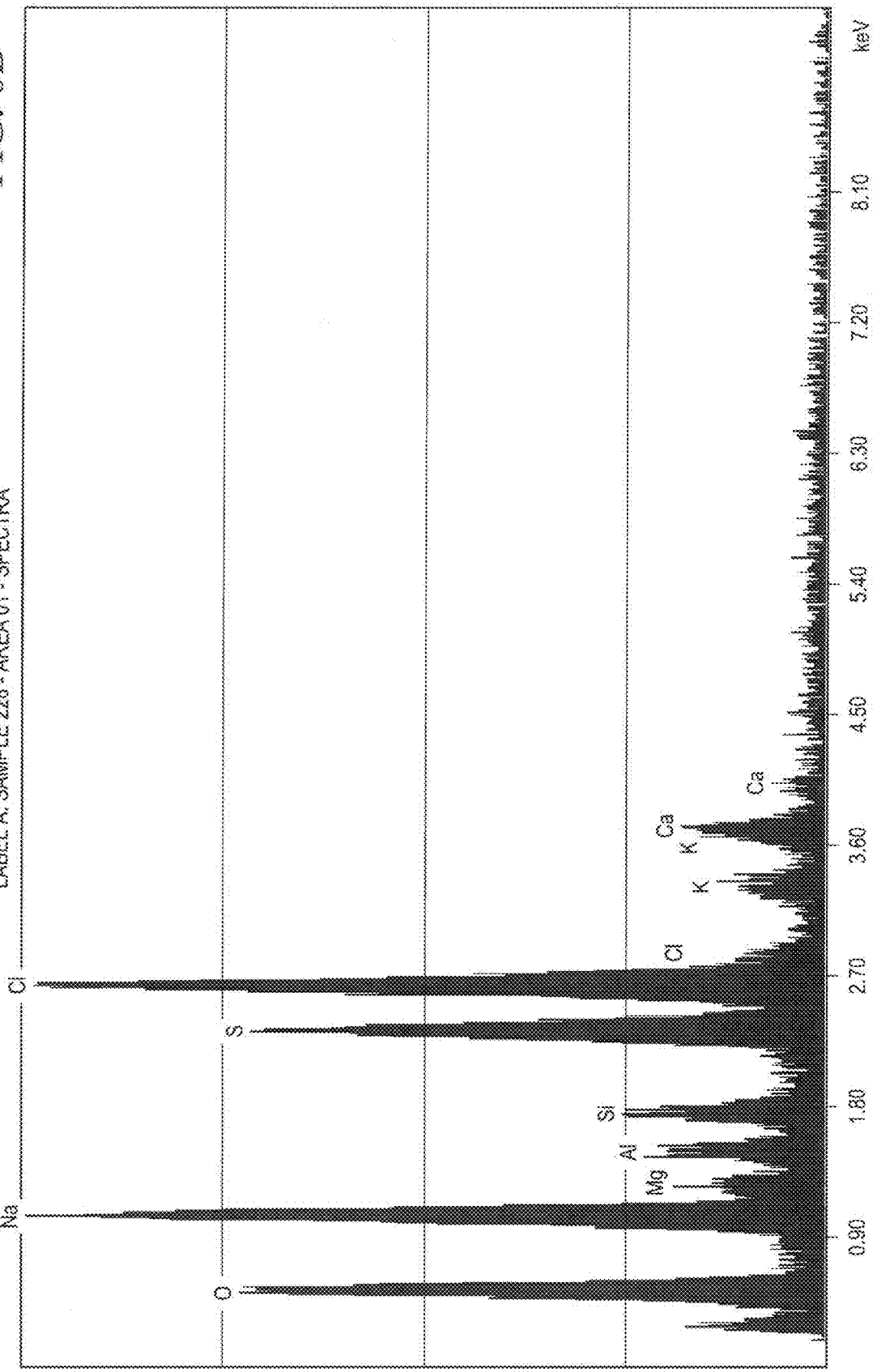

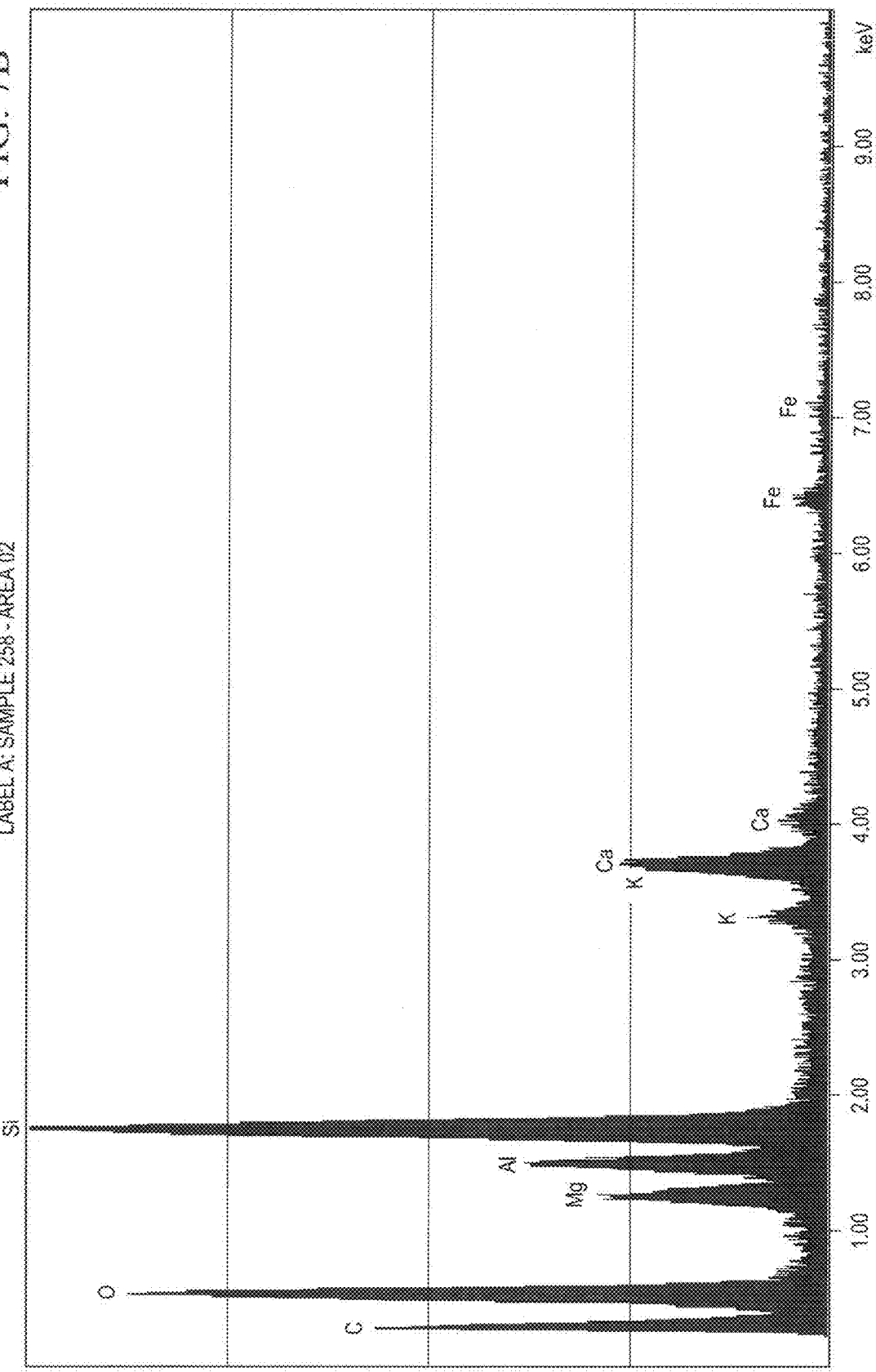

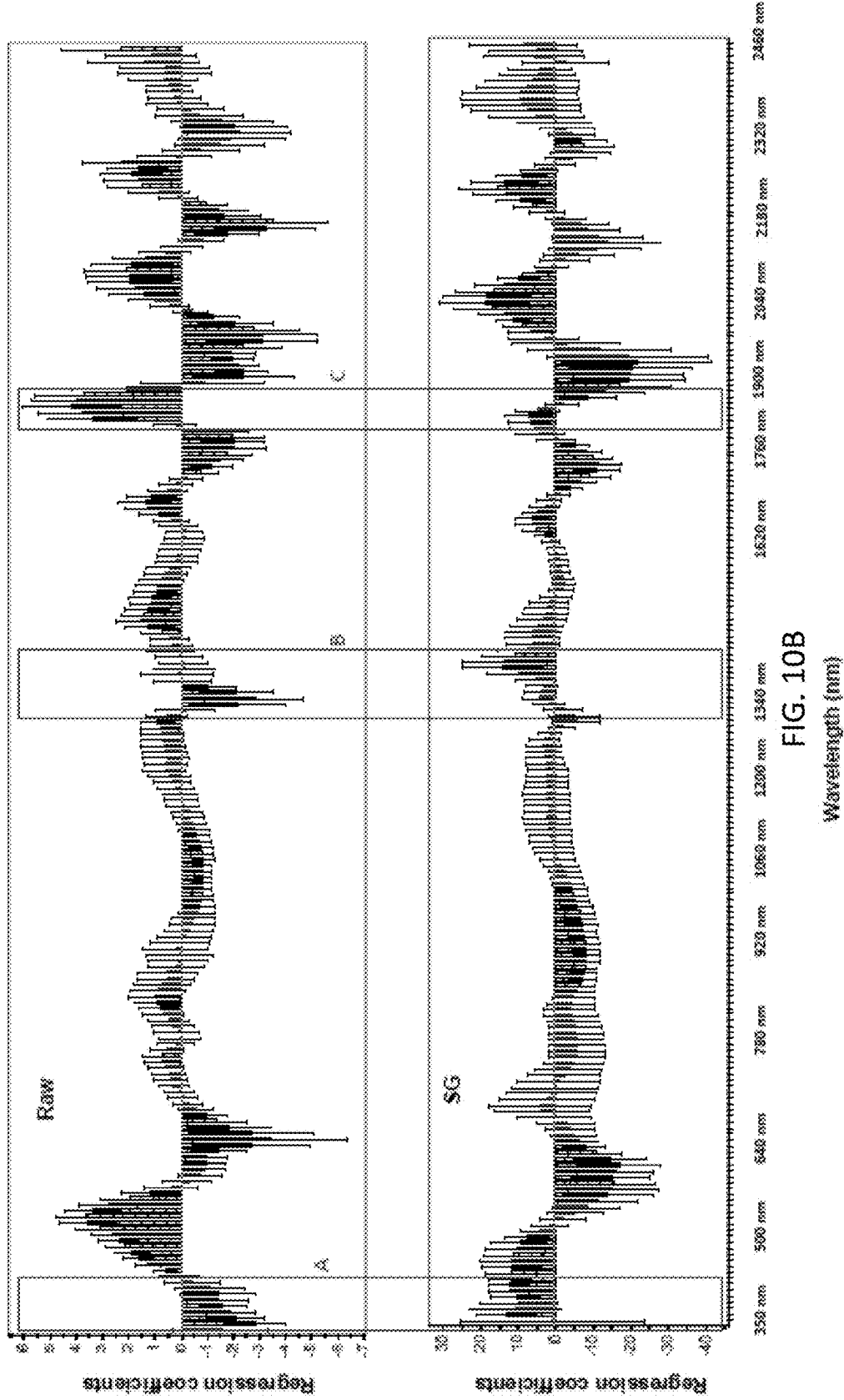

Table 4
Descriptive statistics of PXRF elements, total N and total C used in the multivariate models

| Statistic | Total C | Total N | K | Ca | Ti | V | Mn | Fe | Zn | Rb | Sr | Zr | pB |
|---|---|---|---|---|---|---|---|---|---|---|---|---|---|
| | % | | mg kg⁻¹ | | | | | | | | | | |
| Minimum | 0.067 | 0.0006 | 6738.0 | 1729.00 | 871.0 | 18.0 | 56.0 | 4993.0 | 16.1 | 26.1 | 36.7 | 168.0 | 4.8 |
| Maximum | 6.160 | 0.330 | 21,001.0 | 350,673.0 | 4379.0 | 108.0 | 880.0 | 29,694.0 | 120.0 | 111.7 | 339.0 | 683.0 | 111.0 |
| 1st Quartile | 0.321 | 0.038 | 12,529.0 | 4623.5 | 2112.0 | 41.0 | 201.0 | 13,324.5 | 36.6 | 63.0 | 100.0 | 313.5 | 11.3 |
| Median | 0.523 | 0.060 | 17,277.0 | 5721.0 | 3085.0 | 64.0 | 384.0 | 18,576.0 | 51.0 | 77.5 | 166.0 | 429.0 | 13.5 |
| 3rd Quartile | 1.355 | 0.135 | 18,466.0 | 15,521.0 | 3295.0 | 78.0 | 438.0 | 23,292.0 | 63.2 | 94.1 | 286.0 | 526.0 | 20.9 |
| Mean | 0.832 | 0.084 | 15,801.2 | 11,018.7 | 2764.9 | 60.6 | 338.6 | 18,145.4 | 49.7 | 76.9 | 183.5 | 420.6 | 15.3 |
| Standard deviation (n-1) | 0.712 | 0.062 | 3469.8 | 20,032.0 | 714.4 | 21.3 | 135.2 | 604.12 | 16.8 | 19.9 | 87.0 | 122.6 | 6.2 |

FIG. 27

Table 5
Correlation matrix (p-values) of PXRF elements, total N and total C used in the multivariate models.

| Variables | Total N | K | Ca | Ti | V | Mn | Fe | Zn | Rb | Sr | Zr | Pb | Total C |
|---|---|---|---|---|---|---|---|---|---|---|---|---|---|
| Total N | 0 | | | | | | | | | | | | |
| K | <0.0001[a] | 0 | | | | | | | | | | | |
| Ca | <0.0001 | 0.774 | 0 | | | | | | | | | | |
| Ti | <0.0001 | <0.0001 | 0.032 | 0 | | | | | | | | | |
| V | <0.0001 | <0.0001 | 0.007 | <0.0001 | 0 | | | | | | | | |
| Mn | <0.0001 | <0.0001 | 0.132 | <0.0001 | <0.0001 | 0 | | | | | | | |
| Fe | 0.193 | <0.0001 | 0.656 | <0.0001 | <0.0001 | <0.0001 | 0 | | | | | | |
| Zn | <0.0001 | <0.0001 | 0.022 | <0.0001 | <0.0001 | <0.0001 | <0.0001 | 0 | | | | | |
| Rb | <0.0001 | <0.0001 | <0.0001 | <0.0001 | <0.0001 | <0.0001 | <0.0001 | <0.0001 | 0 | | | | |
| Sr | <0.0001 | <0.0001 | <0.0001 | <0.0001 | <0.0001 | <0.0001 | <0.0001 | <0.0001 | <0.0001 | 0 | | | |
| Zr | <0.0001 | 0.029 | <0.0001 | 0.505 | <0.0001 | 0.066 | <0.0001 | <0.0001 | <0.0001 | <0.0001 | 0 | | |
| Pb | <0.0001 | <0.0001 | <0.0001 | <0.0001 | <0.0001 | <0.0001 | <0.0001 | <0.0001 | <0.0001 | 0.240 | <0.0001 | 0 | |
| Total C | <0.0001 | 0.003 | <0.0001 | 0.000 | <0.0001 | 0.059 | 0.001 | <0.0001 | <0.0001 | <0.0001 | <0.0001 | <0.0001 | 0 |

[a]Values in bold are different from 0 with a significance level alpha = 0.05.

FIG. 28

Table 6
Validation statistics of multivariate models using 30% validation set (n=203).

| Property (%) | Approach | Model | $R^2$ | RMSE (%) | RPD[a] | Bias (%) |
|---|---|---|---|---|---|---|
| *Random splitting scheme* | | | | | | |
| Total C | VisNIR + PXRF | RF[b] | 0.83 | 0.319 | 2.42 | -0.039 |
| | | RCR[c] | 0.93 | 0.209 | 3.69 | -0.026 |
| Total N | VisNIR + PXRF | RF | 0.91 | 0.019 | 3.39 | -0.001 |
| | | PSR | 0.91 | 0.019 | 3.35 | -0.002 |
| Total C | VisNIR | RF | 0.81 | 0.331 | 2.33 | -0.043 |
| | | PSR | 0.90 | 0.233 | 3.31 | -0.025 |
| Total N | VisNIR | RF | 0.90 | 0.019 | 3.23 | -0.0009 |
| | | PSR | 0.89 | 0.020 | 3.14 | -0.0015 |
| Total C | PXRF | RF | 0.77 | 0.366 | 2.11 | -0.051 |
| Total N | PXRF | RF | 0.90 | 0.020 | 3.20 | -0.002 |
| *Without separating soil profile* | | | | | | |
| Total C | VisNIR + PXRF | RF | 0.86 | 0.216 | 2.69 | 0.044 |
| | | PSR | 0.88 | 0.201 | 2.90 | 0.039 |
| Total N | VisNIR + PXRF | RF | 0.89 | 0.018 | 2.99 | 0.005 |
| | | PSR | 0.88 | 0.018 | 2.93 | 0.003 |
| Total C | VisNIR | RF | 0.84 | 0.232 | 2.50 | 0.040 |
| | | PSR | 0.87 | 0.202 | 2.87 | 0.041 |
| Total N | VisNIR | RF | 0.85 | 0.020 | 2.65 | 0.005 |
| | | PSR | 0.88 | 0.019 | 2.89 | 0.003 |
| Total C | PXRF | RF | 0.85 | 0.222 | 2.61 | 0.110 |
| Total N | PXRF | RF | 0.85 | 0.020 | 2.66 | 0.010 |

[a] RPD, Residual prediction deviation.
[b] RF, Random forest regression.
[c] PSR, Penalized spline regression.

FIG. 29

Table 7
Prediction accuracies of TC and TN using whole field holdout validation. Models were created using random forest regression with two fields and then validated using the third field. Twelve separate models were calibrated and validated.

| Validation field | Parameter | RMSE-test(%) | | RPD[a] | | Bias (%) | |
|---|---|---|---|---|---|---|---|
| | | VisNIR | VisNIR + PXRF | VisNIR | VisNIR + PXRF | VisNIR | VisNIR + PXRF |
| Nebraska | TC | 0.82 | 0.80 | 0.53 | 0.55 | -0.64 | -0.64 |
| | TN | 0.07 | 0.06 | 0.54 | 0.62 | -0.06 | -0.05 |
| Lubbock | TC | 0.82 | 0.80 | 0.76 | 0.78 | 0.48 | 0.44 |
| | TN | 0.06 | 0.06 | 0.32 | 0.32 | 0.05 | 0.05 |
| California | TC | 1.96 | 2.00 | 0.07 | 0.07 | 1.90 | 1.96 |
| | TN | 0.12 | 0.11 | 0.13 | 0.13 | 0.11 | 0.10 |

[a] RPD, Residual prediction deviation.

FIG. 30

Table 8
Soil series and taxonomic classification of samples (n=108) utilized for a PXFR + VisNir DRS study of hydrocarbon contamination in West Texas, USA.

| n | Soil Series | Classification [a] |
|---|---|---|
| 2 | Portales | Fine-loamy, mixed, superactive, thermic Aridic Calciustolls |
| 40 | Olton | Fine, mixed, superactive, thermic Aridic Paleustolls |
| 2 | Layton/Mobeetie | Mixed, mesic Psammentic Haploxerolls/coarse-loamy, mixed, superactive, thermic Aridic Haplustepts |
| 5 | Vernon | Fine, mixed, active, thermic Typic Haplustepts |
| 3 | Miles | Fine-loamy, mixed, superactive, thermic Typic Paleustalfs |
| 27 | Mobeetie/Potter | Coarse-loamy, mixed, superactive, thermic Aridic Haplustepts/loamy-skeletal, carbonatic, thermic Petronodic Ustic Haplocalcids |
| 7 | Patricia/Amarillo | Fine-loamy, mixed, superactive, thermic Aridic Paleustalfs/fine-loamy, mixed, superactive, thermic Aridic Paleustalfs |
| 15 | Amarillo | Fine-loamy, mixed, superactive, thermic Aridic Paleustalfs |
| 6 | Acuff | Fine-loamy, mixed, superactive, thermic Aridic Paleustolls |
| 1 | Abilene | Fine, mixed, superactive, thermic Pachic Argiustolls |

[a] Soil Survey Staff (2014)

FIG. 31

Table 9
Summary statistics of soil (n = 108) samples utilized for a PXRF + VisNIR DRS study of hydrocarbon contamination in West Texas, USA.

| | TPH | Log$_{10}$ (TPH + 1) | Al | Si | K | Ca | Ti | Mn |
|---|---|---|---|---|---|---|---|---|
| | mg kg$^{-1}$ | | | | | | | |
| Minimum | 0.00 | 0.000 | 8891.28 | 46,772.44 | 3327.63 | 275.27 | 1010.35 | 65.59 |
| Maximum | 326,294.48 | 5.514 | 34,595.56 | 220,289.36 | 14,740.18 | 149,770.88 | 6067.06 | 504.76 |
| 1$^{st}$ quartile | 14,057.06 | 4.148 | 18,806.46 | 103,589.36 | 7848.56 | 14,858.24 | 1950.74 | 205.79 |
| Median | 54,678.88 | 4.738 | 23,811.48 | 134,800.24 | 8933.81 | 32,825.52 | 2282.81 | 255.09 |
| 3rd quartile | 117,384.43 | 5.069 | 26,522.36 | 152,328.08 | 9980.20 | 53,295.69 | 2525.84 | 302.09 |
| Mean | 80,421.66 | 4.265 | 22,760.72 | 130,253.44 | 8951.10 | 35,561.34 | 2351.78 | 261.30 |
| Variance (n -1) | 6,388,692,219.66 | 1.834 | 35,559,837.21 | 1,533,794,474.09 | 4,167,447.98 | 669,698,764.13 | 601,855.61 | 8589.18 |
| Standard deviation | 79,929.30 | 1.354 | 5963.21 | 39,163.69 | 2041.43 | 25,878.54 | 775.79 | 92.68 |

| Fe | Cu | Zn | Rb | Sr | Y | Zr | Pb |
|---|---|---|---|---|---|---|---|
| 7072.50 | 7.45 | 14.27 | 17.08 | 25.18 | 4.93 | 90.24 | 6.05 |
| 44,104.87 | 485.16 | 1828.91 | 107.82 | 1985.51 | 26.11 | 382.28 | 594.11 |
| 14,775.25 | 15.96 | 53.40 | 39.20 | 83.07 | 10.80 | 173.00 | 14.00 |
| 18,046.71 | 21.69 | 77.65 | 46.32 | 109.39 | 12.93 | 201.37 | 22.62 |
| 21,311.67 | 33.32 | 135.47 | 54.19 | 138.37 | 15.98 | 262.33 | 43.49 |
| 19,106.42 | 41.36 | 147.85 | 47.61 | 185.42 | 13.41 | 213.70 | 42.41 |
| 46,883,696.62 | 4055.53 | 46,145.58 | 233.83 | 83,880.78 | 19.07 | 4149.32 | 4447.61 |
| 6847.17 | 63.68 | 214.82 | 15.29 | 289.62 | 4.37 | 64.42 | 66.69 |

FIG. 32

Table 10
Summary model statistics obtained for soil (TPH +1) by two difference approaches using derivative spectra and three different multivariate algorithms. Also ratios of PSR+RF model with other model results are shown. For example, a value of 1.26 for PLS model only means the $R^2$ of PSR+RF using derivative spectra is ~26% higher than the former.

| Approach | Model[a] | PLS LF[b] | $R^2$ | RMSE (log$_{10}$ mg kg$^{-1}$) | RPD[c] | RPIQ[d] | Bias (log$_{10}$ mg kg$^{-1}$) | $R^2$ | RMSE (log$_{10}$ mg kg$^{-1}$) | RPD |
|---|---|---|---|---|---|---|---|---|---|---|
| | | | Independent validation | | | | | Ratio with PSR + RF results for PXRF + VisNIR | | |
| VisNIR | PLS | 3 | 0.73 | 0.59 | 1.96 | 0.63 | -0.167 | 1.07 | 0.89 | 1.12 |
| | PSR | - | 0.70 | 0.75 | 1.86 | 0.60 | -0.140 | 1.11 | 0.71 | 1.18 |
| | RF | - | 0.61 | 0.70 | 1.64 | 0.57 | -0.241 | 1.28 | 0.75 | 1.34 |
| VisNIR + PXRF | PLS | 1 | 0.62 | 0.70 | 1.64 | 0.55 | -0.244 | 1.26 | 0.75 | 1.34 |
| | PSR | - | 0.73 | 0.59 | 1.96 | 0.65 | -0.167 | 1.07 | 0.89 | 1.18 |
| | PSR + RF | - | 0.78 | 0.53 | 2.19 | 0.75 | -0.166 | 1.00 | 1.00 | 1.00 |
| | PSR + linear regression | - | 0.72 | 0.60 | 1.93 | 0.65 | -0.060 | 1.08 | 0.88 | 1.14 |

[a] PLS, partial least squares regression; PSR, penalized spline regression; RF, random forest.
[b] PLS LF, partial least squares regression latent factor.
[c] RPD, residual prediction deviation.
[d] RPIQ, ratio of performance to inter-quartile distance.

FIG. 33

PORTABLE APPARATUS FOR SOIL CHEMICAL CHARACTERIZATION

CROSS REFERENCE TO RELATED APPLICATIONS

This application claims priority to, and is the National Phase of International Application No. PCT/US2015/036537, filed on Jun. 18, 2015, which claims the benefit under 35 U.S.C. § 119(e) of U.S. Provisional Application No. 62/013,692, filed Jun. 18, 2014. All of which are hereby incorporated by reference in their entirety.

FIELD OF INVENTION

The present invention relates generally to the field of chemical and, more particularly, to a portable apparatus for soil chemical characterization using x-ray fluorescence spectrometry and visible near infrared diffuse reflectance spectroscopy.

BACKGROUND ART

Soil Salinity:

Salt affected soils are caused by excess accumulation of salt typically most pronounced at the soil surface. Salt is often derived from geological formations featuring shale, marl, limestone, sylvite, gypsum, and halite. Variability of soil salinity is affected by parent material, soil type, and landscape position [10]. Moreover, salts can be transported to the soil surface by capillary action from brackish water tables and accumulated due to evaporation. They can also accumulate as a result of anthropogenic activities such as fertilization or oil production. Soil salinity is generally measured via electrical conductivity (EC) in soil saturated paste (ECp), its liquid extract (ECe), or using different soil to water suspensions [34]. Soil with an ECe greater than 4 dS m$^{-1}$, is referred to as saline [7]. Plant tolerance of salinity is species specific, but values greater than 4 dS m$^{-1}$ constrain the growth of many agronomic crops. Developed in the mid-1950s, ECe is one of the most widely reported soil quality assessment parameters [2, 22, 35]. Regular monitoring of soil salinity is essential for efficient soil and water management and sustainability of agricultural lands [5], especially in arid and semiarid environments. Yet, traditional laboratory methods for soil salinity characterization can be laborious and costly. Additionally, many soils are highly spatially variable, with salinity changing rapidly over small distances relative to topography and other factors [29]. Thus, a large number of soil samples are often required to adequately characterize soil salinity across landscapes.

To alleviate the cost of extensive sampling, previous studies have used remotely sensed (RS) data/imagery for detecting soil salinity. Specifically, soil salinity is related to different spectral bands, ratios, and parameters extracted from satellite imagery using soil and vegetation based indices [14, 15, 21, 23, 40]. While promising, these methods are limited by factors such as spatial and spectral resolution of the image, vegetation coverage, and atmospheric effects ([16]; Metternich and Zinck, 2008). One of the newest RS satellites available for research is Landsat 8, which was launched on Feb. 11, 2013. Landsat 8 orbits the entire Earth every 16 days in an 8-day offset from Landsat 7. The collected data is orthorectified and available to download at no charge. Landsat 8 carries two different instruments: 1) the operational land imager (OLI) sensor involves refined heritage bands, and 2) the thermal infrared sensor (TIRS) provides two thermal bands. Both sensors supply improved signal-to-noise (SNR) radiometric performance quantized over a 12-bit dynamic range. They provide 4096 potential grey levels in an image compared with only 256 grey level in the previous 8-bit instrument. Therefore, the improved signal to noise performance enables better characterization of land cover state and condition. The final products are delivered as 16-bit images scaled to 55,000 grey levels.

Landsat 8 images include nine spectral bands with a spatial resolution of 30 m for bands 1 to 7 and 9. A new ultra-blue band is useful for coastal and aerosol studies and band 9 is useful for cirrus cloud detection. The resolution of band 8 is 15 m while thermal bands 10 and 11 are useful in providing more accurate surface temperatures via 100 m resolution. Table 1 shows the differences between Landsat 7 and Landsat 8.

TABLE 1

Comparison between Landsat 7 and Landsat 8 spectral bands, wavelength (nm), and detector resolution (m) [41]

| Landsat 7 | | | Landsat 8 | | |
|---|---|---|---|---|---|
| Bands | Wavelength | Resolution | Bands | Wavelength | Resolution |
| 1 (blue) | 0.45-0.52 | 30 | 1 (coastal aerosol) | 0.43-0.45 | 30 |
| 2 (green) | 0.52-0.60 | 30 | 2 (blue) | 0.45-0.51 | 30 |
| 3 (red) | 0.63-0.69 | 30 | 3 (green) | 0.53-0.59 | 30 |
| 4 (NIR) | 0.77-0.90 | 30 | 4 (red) | 0.64-0.67 | 30 |
| 5 (SWIR 1) | 1.55-1.75 | 30 | 5 (NIR) | 0.85-0.88 | 30 |
| 6 (TIRS) | 10.4-12.50 | 60 | 6 (SWIR 1) | 1.57-1.65 | 30 |
| 7 (SWIR 2) | 2.09-2.35 | 30 | 7 (SWIR 2) | 2.11-2.29 | 30 |
| 8 (Panchromatic) | 0.52-0.90 | 15 | 8 (Panchromatic) | 0.50-0.68 | 15 |
| | | | 9 (circus) | 1.36-1.39 | 30 |
| | | | 10 (TIRS 1) | 10.60-11.19 | 100 |
| | | | 11 (TIRS 2) | 11.50-12.51 | 100 |

A different approach for rapidly characterizing soil salinity is offered by proximal sensing techniques using either visible near infrared diffuse reflectance spectroscopy (Vis-NIR DRS) or portable x-ray fluorescence (PXRF) spectrometry. Fariteh et al. (2007) studied DRS to determine its capability to identify different salt minerals in addition to quantifying soil salinity levels using samples artificially treated by different salt minerals in the laboratory, as well as those collected from a field experiment. Weindorf et al. [47] tested the effectiveness of PXRF for directly quantifying of gypsum and soil salinity. Results showed a good correlation between lab data and PXRF predictions using a simple linear regression for gypsum ($r^2$=0.88) and soil salinity ($r^2$=0.84) with low RMSEs. Swanhart [39] used multiple linear regression to relate PXRF elemental data (Cl, S, K, Ca) to saline, coastal soils from Louisiana, USA with a $r^2$ of 0.86 and a RMSE of 0.67 between the datasets. Early studies investigating remote sensing or hyperspectral reflectance spectroscopy mainly explored their potential for spectral characterization of different salt mineral types or for qualitative and quantitative characterization of salinity using samples artificially spiked in the laboratory [5]. Thus, the number of such studies featuring quantitative assessment of soil salinity under natural field conditions is limited.

Carbon and Nitrogen:

Both carbon and nitrogen are critical elements in soils. Soil total carbon (TC) can improve soil fertility, quality, and water retention, and ultimately maintain and increase crop production [91]. In addition, the soil carbon pool, as the largest reservoir in the terrestrial ecosystem, is 3.3 times the size of the atmospheric pool and 4.5 times the size of the biotic pool [79]. Small changes in the soil carbon pool may influence global climate change. Soil TC loss due to cultivation degrades soil fertility and quality, reduces biomass productivity, and adversely impacts water quality; depletions exacerbated by projected global warming [79, 86]. Soil total nitrogen (TN), a critical macronutrient for plant growth, is a major determinant and indicator of soil fertility and quality, and also the most commonly deficient soil nutrient [98, 87]. However, excessive nitrogen contents in soil not only lead to non-point source pollution, such as eutrophication and associated water-quality problems [61, 124], but also can be released to the atmosphere as greenhouse gases (e.g., nitrous oxide, N2O) [81]. Moreover, the C:N ratio is a good indicator of the degree of decomposition and quality of the organic matter held in the soil [53]. Soil TC is the driving force of biological activity, serving as the primary source of energy and nutrients for many soil organisms [66], and an important factor affecting nitrogen mineralization and immobilization in soils [65, 72, 80]. Soil nitrogen, as a key nutrient, can directly influence carbon sequestration in terrestrial ecosystems [95]. Therefore, spatial predictions of soil TC and TN contents are needed for a wide range of agricultural and environmental applications [91, 116].

For decades, classical laboratory-based methods have been utilized for quantifying soil TC and TN content. Two basic approaches are used to quantify TC in soils, namely, dry combustion and wet combustion [92]. Dry combustion requires separate determinations for inorganic- and organic-C, is time consuming, relatively expensive, and not adaptable to in situ determinations [99]. Wet combustion is a semi-quantitative estimate of soil carbon due to the lack of a universal conversion factor for each soil analyzed; it is time-consuming, tedious, and generates toxic waste that must be disposed of properly [92, 66]. Another relatively inexpensive and rapid technique, loss-on-ignition (LOI) has been shown to be inaccurate in some instances due to the decomposition of certain mineral fractions at high temperatures [92, 79]. The Dumas [67] (dry combustion) and [76] (wet oxidation) methods have gained general acceptance for determination of TN in the laboratory. However, both methods are time consuming, destructive to the sample being analyzed, and fail to recover some forms of N, particularly N in certain heterocyclic compounds and compounds containing N—N and N—O linkages [54]. The Dumas method is also expensive and has lower precision than Kjeldahl approaches [54]. Another method of quantification involves ion sensing electrodes, as a quick and reliable alternative to chemical-based laboratory methods for nitrate measurements. However, interference from other similar and undesired ions can be problematic; sometimes causing instability in attaining equilibrium [78]. Also, cell membranes, reference electrodes, and amplifier distortions may cause anomalous readings [78]. The disadvantages of all these traditional laboratory analysis methods are compounded by the large number of samples required for accurate assessment [84, 86]. Although these traditional methods are relatively accurate and widely accepted, they require extensive lab work and destroy the sample during processing. Therefore, there is a growing demand for rapid, cost effective, and nondestructive approaches for predicting C and N in situ. Proximal soil sensing techniques have the potential to eliminate the aforementioned constraints.

One popular proximal soil sensing technique, visible near infrared (VisNIR) spectroscopy, is quick, cost-effective, non-destructive, requires little sample preparation with no hazardous chemicals used, and is highly adaptable to automated and in situ measurements [85, 46]. Such approaches have attracted widespread interest in soil science since the 1980s [108]. The same spectra from scanning a soil with VisNIR spectroscopy can be used for the prediction of a variety of soil properties simultaneously [102], especially soil carbon. Many recent studies have been conducted on quantifying TC [114, 86], soil organic carbon, inorganic carbon [101, 89, 71] and other soil carbon fractions [115, 102] using VisNIR spectroscopy in the laboratory, in situ, or using airborne imaging spectroscopy [90, 89, 109, 70]. Comparatively fewer studies have focused on estimating soil nitrogen [103, 60, 52] through these approaches, let alone simultaneously with soil carbon. Although these studies obtained excellent results, which showed that it is a viable alternative for the routine quantitative analysis of soil carbon, lab-based VisNIR can only provide semi-quantitative estimation with residual prediction deviation (RPD)=1.5-2.0 [57]. Many factors, including moisture, particle size, mineral composition, and the presence of Fe, influence the reflectance of soils [74, 82, 99] and soil VisNIR spectra are largely non-specific, quite weak, and broad due to overlapping absorptions of soil constituents [100]. Morgan et al. [89] found VisNIR spectra alone do not provide sufficient accuracy for stand-alone C sequestration measurement, monitoring and verification. VisNIR spectroscopy alone will never provide complete soil characterization.

Another proximal soil sensing technique, x-ray fluorescence spectrometry has been used since the 1930s [20]. Given technological advances in recent years, portable x-ray fluorescence (PXRF) spectrometry has been developed and improved greatly with a number of significant advantages including minimal sample preparation, high sample throughputs, and the rapid, nondestructive, accurate, low cost, and in situ identification of many elements [112, 50]. Therefore, PXRF has become increasingly popular and been adopted by environmental consultancies, research institutions, and governmental agencies such as the US Environmental Protection Agency via Method 6200 [113], the International Organization for Standardization (ISO) [75], and the National Institute for Occupational Safety and Health (NIOSH) Method 7702 [93] for the analysis of soil and sediments. Portable x-ray fluorescence spectrometry can quantify elements from z=15 (P) through 94 (Pu) and is useful for environmental monitoring of many elements in soils and other geological materials [47, 123]. Applied to soil science, many studies have focused on metal contamination assessment using PXRF [119, 122, 96, 73], and PXRF elemental data has been used as a proxy for a wide number of soil parameters such as pH [104], cation exchange capacity [105], soil calcium and gypsum [118, 47, 125], soil texture [50], soil salinity [110], and soil horizon differentiation [120, 121]. However, PXRF cannot presently be used to quantify lighter elements [94] (e.g., Na, N, C, H, Li) given their stable electron configurations and low fluorescent energies. Few studies have attempted to predict soil carbon and nitrogen by using PXRF, given that indirect approaches to these determinations are required as direct measurements are not possible. However, Weindorf et al. [121] tried to link organic carbon content with PXRF elemental concentration while differentiating spodic horizons, and found some associations of soil carbon and nitrogen with PXRF elemental data.

Many studies have reported successful prediction of soil properties using a single instrument (e.g., VisNIR, PXRF, and so on). However, single sensors provide no robust capability to measure soil properties successfully at different sampling sites because of the complex nature of soils [117]. Wang et al. [117] predicted soil texture using Fourier transform near-infrared (NIR) spectroscopy and PXRF spectrometry with data fusion and concluded soil textural fractions predicted with sample data and sensor data fusion methods (e.g., clay, validation $R^2=0.83$-$0.86$, RPD=1.94-2.39) were more accurate than those with individual sensors and individual data sets (e.g., clay, validation $R^2=0.61$-$0.74$, RPD=1.56-2.36).

Petroleum Contaminated Soils:

Soil petroleum contamination is a serious environmental concern because of its neurotoxic effects on humans and animals [132]. The growth of the petroleum industry worldwide and marketing of petroleum products have resulted in countless chances for spillage. Most commonly, when an underground storage tank is removed, soil petroleum contamination is discovered which may pose an even more worrisome problem, groundwater contamination. Moreover, environmental pollution resulting from crude oil drilling has put numerous food crops under considerable risk [160]. On Apr. 20, 2010, the largest accidental marine oil spill in the history of the petroleum industry occurred following a sea-floor oil spill gusher from the Deepwater Horizon drilling rig explosion in the Gulf of Mexico south of Louisiana, USA. To date, the total costs associated with lost jobs, contaminated food and water, cleanup, restoration, and environmental damage have not been fully determined [133] and may not be for many years. Initial estimates placed the cost of damages to the Oil Company, environment, and US Gulf Coast economy at $36.9 billion [163], but later estimates by the Oil Company were closer to $41.0 billion. Undoubtedly, rapid and cost-effective means of identifying total petroleum hydrocarbon (TPH) content in contaminated soils could substantially reduce the cost involved in their restoration.

Rapid and wide scale characterization of soil petroleum contamination is not feasible with traditional gas chromatography based methods since these are prohibitively expensive, extremely laborious, time consuming, sometimes show high variability (an order of magnitude) in TPH results across commercial laboratories, lack field-portability, and warrant rigorous field sampling [140, 153].

Remote sensing tools appear to be a viable technology to provide a comprehensive solution to this problem [164]. Specifically, a mounting body of literature underlines the usefulness of visible and near-infrared (VisNIR) diffuse reflectance spectroscopy (DRS) (350-2500 nm) as a rapid and noninvasive technique for the estimation of several soil properties simultaneously and in-situ with minimum or no sample pretreatments [13, 59, 46, 115]. Chakraborty et al. [134, 62, 135, 12] demonstrated the capability of VisNIR DRS to estimate soil petroleum contamination from a single reflectance spectrum of the contaminated soil by means of multivariate regression models. Other researchers also independently showed the robustness of VISNIR DRS models for rapidly estimating TPH and polycyclic aromatic hydrocarbons [145, 141, 162, 156]. The underlying principle is based on the diagnostic absorption bands (primarily overtones and combinations) in the VisNIR region arising from the C—H bond in hydrocarbons, helping in both qualitative and quantitative analysis of contaminated soils.

Another soil sensing technique, X-ray fluorescence spectrometry, has been used since 1930s [20]. Given technological advances in recent years, portable X-ray fluorescence (PXRF) spectrometry has been developed and improved greatly with a number of significant advantages including minimal sample preparation, high sample throughputs, and the rapid, nondestructive, accurate, low cost, and in-situ identification of many elements [112, 166, 50]. Therefore, PXRF has become increasingly popular for soil/sediment analysis with references such as Method 6200 [113] among others. PXRF can quantify elements from z=15 (P) through 94 (Pu) and is useful for environmental monitoring of many elements in soils and other geological materials [47, 123]. Applied to soil science, many studies have focused on metal contamination assessment using PXRF [119, 122, 96, 161, 73], and PXRF elemental data has been used as a proxy for a wide number of soil parameters such as pH [104], cation exchange capacity [105], soil calcium and gypsum [118, 47, 125], soil texture [50], soil salinity [110], and soil horizonation [120, 121].

SUMMARY OF THE INVENTION

Three alternative methods (VisNIR DRS, PXRF, and RS) for determining soil characteristics were compared to traditional laboratory analysis. With respect to soil salinity, elemental concentrations (determined via PXRF) of S and Cl were found to be most strongly correlated to soil EC (1:5). With consideration of VisNIR DRS data, two multivariate algorithms were tested (PLS and SVR) and generally produced strong, significant relationships to soil EC (1:5). Comparing the relative accuracies of PXRF and RS in predicting soil EC (1:5), both produced suboptimal results relative to VisNIR DRS alone. Evaluated independently, the techniques were generally ranked as VisNIR DRS>PXRF>RS. Conversely, the synthesis of VisNIR DRS and PXRF datasets produced predictive results better than the prior art. The synthesis of all three datasets produced the best predictive results; better than any one technique taken independently. As these types of data are quick, easy, and inexpensive to collect, two or three datasets can be combined for optimal soil salinity prediction. The present invention provides researchers with a tool that obtains results of comparable quality to lab-derived data, yet with less time and effort than traditional laboratory salinity determinations.

For example, the present invention provides a computerized method for determining one or more properties of a soil sample using a visible near infrared diffuse reflectance (VisNIR) spectroradiometer, a x-ray fluorescence (PXRF) spectrometer, a probe connected to the VisNIR spectroradiometer and the PXRF spectrometer, one or more processors communicably coupled to the VisNIR spectroradiometer and the PXRF spectrometer, and one or more input/output interfaces communicably coupled to the one or more processors. The soil sample is scanned using a visible near infrared diffuse reflectance (VisNIR) spectroradiometer. The soil sample is also scanned using a x-ray fluorescence (PXRF) spectrometer. A diffuse reflectance spectra is received from the VisNIR spectroradiometer and elemental data is received from the PXRF spectrometer. The one or more processors determine one or more properties of the soil sample using a predictive model that relates the diffuse reflectance spectra and the elemental data to the one or more properties. The one or more properties of the soil sample are provided to one or more input/output interfaces. The foregoing method can be performed by a computer program embodied on a non-transitory computer readable medium.

In addition, the present invention provides an apparatus that includes a probe, a visible near infrared diffuse reflectance (VisNIR) spectroradiometer connected to the probe, a x-ray fluorescence (PXRF) spectrometer connected to the probe, one or more processors communicably coupled to the VisNIR spectroradiometer and PXRF spectrometer, and one or more input/output interfaces communicably coupled to the one or more processors. The one or more processors scan the soil sample using the VisNIR spectroradiometer, scan the soil sample using the PXRF spectrometer, receive a diffuse reflectance spectra from the VisNIR spectroradiometer and elemental data from the PXRF spectrometer, determine one or more properties of the soil sample using a predictive model that relates the diffuse reflectance spectra and the elemental data to the one or more properties, and provide the one or more properties of the soil sample to the one or more input/output interfaces.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which:

FIGS. 5A1-5G7 are matrix plots showing correlation between PXRF sensed elements and soil salinity parameters;

FIGS. 6A and 6B are graphs showing saline, playa soil sample mineralogy as determined by x-ray diffraction (FIG. 6A) and elemental composition as determined by EDS (FIG. 6B) for soils from West Texas, USA;

FIGS. 7A and 7B are graphs showing non-saline, upland soil sample mineralogy as determined by x-ray diffraction (FIG. 7A) and elemental composition as determined by EDS (FIG. 7B) for soils from West Texas, USA;

FIGS. 10A and 10B are weighted regression coefficients (black) of the partial least squares model using Raw (FIG. 10A) and SG (FIG. 10B) spectra of soil samples;

FIG. 27 is a table of descriptive statistics of PXRF elements, total N and total C used in the multivariate models (Table 4);

FIG. 28 is a table of correlation matrix (p-values) of PXRF elements, total N and total C used in the multivariate models (Table 5);

FIG. 29 is a table of validation statistics of multivariate models using 30% validation set (n=203) (Table 6);

FIG. 30 is a table of prediction accuracies of TC and TN using whole field holdout validation (Table 7);

FIG. 31 is a table of soil series and taxonomic classification of samples (n=108) utilized for a PXFR+VisNir DRS study of hydrocarbon contamination in West Texas, USA (Table 8);

FIG. 32 is a table of summary statistics of soil (n=108) samples utilized for a PXRF+VisNIR DRS study of hydrocarbon contamination in West Texas, USA (Table 9); and FIG. 33 is a table of Summary model statistics obtained for soil (TPH+1) by two difference approaches using derivative spectra and three different multivariate algorithms (Table 10).

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Note that these terms may be used interchangeable without limiting the scope of the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Figure 1:
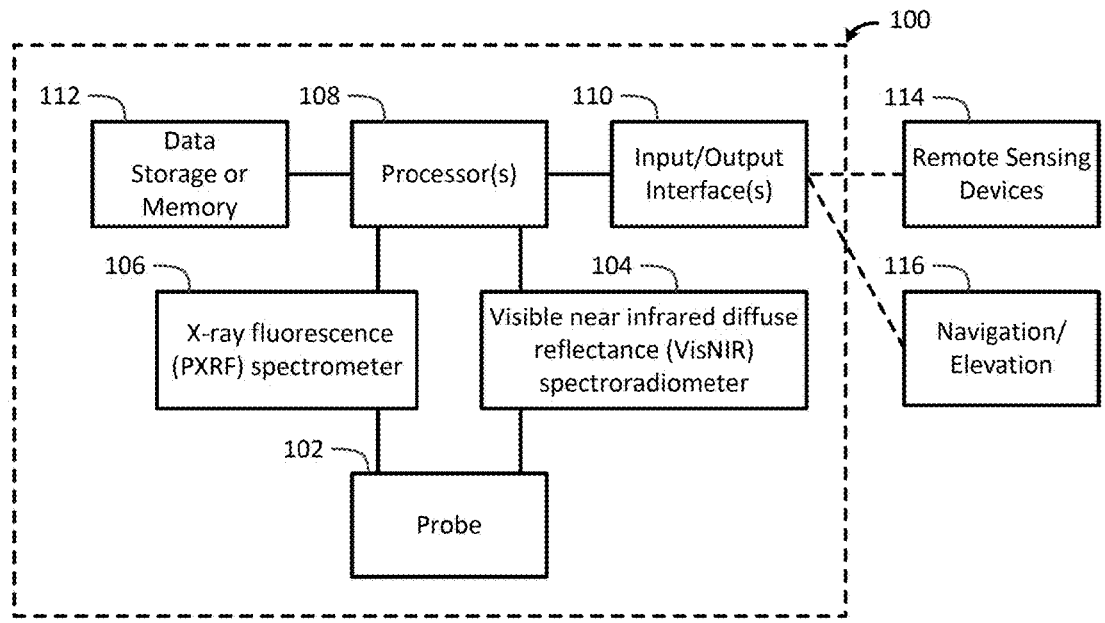
FIG. 1 is a block diagram of an apparatus in accordance with one embodiment of the present invention.

Now referring to FIG. 1, a block diagram of an apparatus 100 in accordance with one embodiment of the present invention is shown. The apparatus 100 includes a probe 102, a visible near infrared diffuse reflectance (VisNIR) spectroradiometer 104 connected to the probe 102, a x-ray fluorescence (PXRF) spectrometer 106 connected to the probe 102, one or more processors 108 communicably coupled to the VisNIR spectroradiometer 104 and PXRF spectrometer 106, and one or more input/output interfaces 110 communicably coupled to the one or more processors 108. The one or more processors 108 scan the soil sample using the VisNIR spectroradiometer 104, scan the soil sample using the PXRF spectrometer 106, receive a diffuse reflectance spectra from the VisNIR spectroradiometer 104 and elemental data from the PXRF spectrometer 106, determine one or more properties (e.g., chemical properties, physical properties, etc.) of the soil sample using a predictive model that relates the diffuse reflectance spectra and the elemental data to the one or more properties, and provide the one or more properties of the soil sample to the one or more input/output interfaces. Non-limiting examples of the one the one or more properties of the soil sample are salinity, textural constituents, soil pH, soil carbon content or clay mineralogy. The apparatus can be portable such that the one or more processors 108 perform the scanning, receiving, determining and providing steps in situ.

The one or more processors 108 may transmit or receive data wirelessly via the one or more input/output interfaces 110. The one or more input/output interfaces 110 can be any type of wired or wireless interface to other components, devices or systems either remote or locally located to the apparatus 110. The one or more input/output interfaces 110 may be a display, a data storage, a printer, a communications interface, etc.

For example, the one or more processors 108 may receive a set of multispectral reflectance values related to the soil sample from a remote sensing device 114 when the predictive model further relates the set of multispectral reflectance values to the one or more properties. The remote sensing device 114 can be a satellite (e.g., Landsat 7, Landsat 8, etc.) in which case the one or more processors 108 further extract the multispectral reflectance values from a satellite imagery using a soil and vegetation based indices. Alternatively, the one or more processors 108 may receive the set of multispectral reflectance values related to the soil sample from the remote sensing device 114 by retrieving the set of multispectral reflectance values from a memory or a data storage 112 communicably coupled to the one or more processors 108 or remote data storage via the one or more input/output interfaces 110. In addition, the one or more processors 108 may determine a geographic location of the soil sample using a space-based satellite navigation system 116 or an elevation of the soil sample.

The one or more processors 108 may also calibrate the predictive model, reduce dimensionality and qualitative discrimination of the diffuse reflectance data, etc. The predictive model uses a partial least squares regression (PLS) multivariate algorithm or a support vector regression (SLR) multivariate algorithm.

Figure 2:
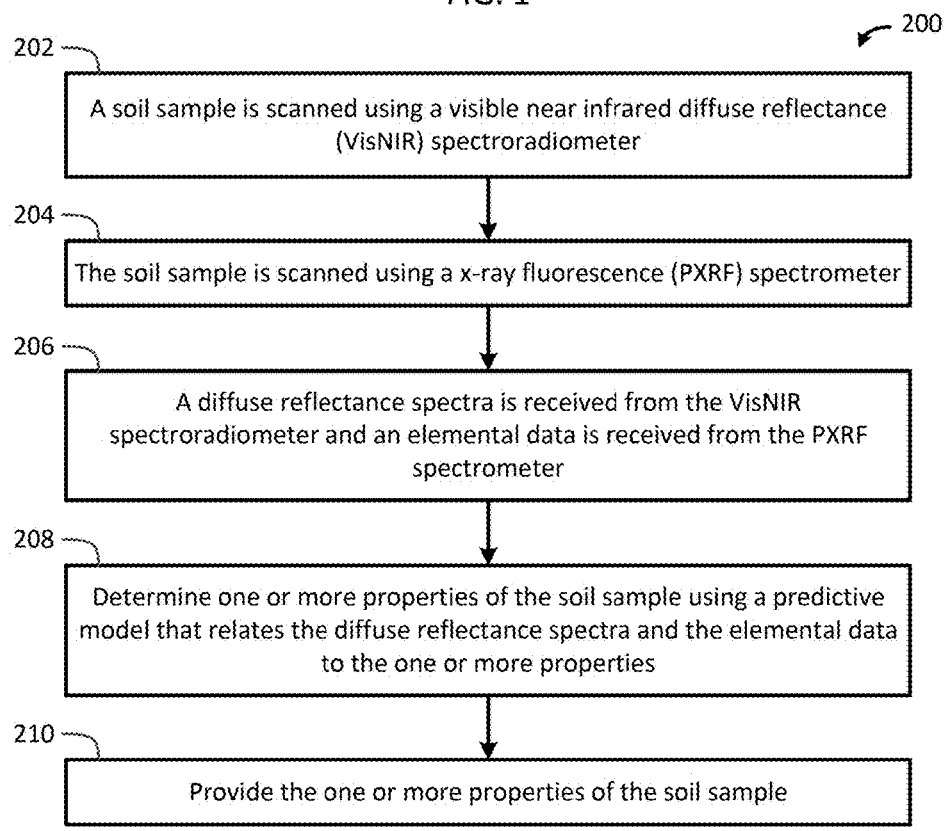
FIG. 2 is a flow chart of a method in accordance with one embodiment of the present invention.

Referring now to FIG. 2, a flow chart of a computerized method 200 for determining one or more properties of a soil sample in accordance with one embodiment of the present invention is shown. The method is performed using an apparatus as shown in FIG. 1 or other suitable systems, devices or components. The soil sample is scanned using a visible near infrared diffuse reflectance (VisNIR) spectroradiometer in block 202. The soil sample is also scanned using a x-ray fluorescence (PXRF) spectrometer in block 204. A diffuse reflectance spectra is received from the VisNIR spectroradiometer and elemental data is received from the PXRF spectrometer in block 206. One or more properties (e.g., chemical properties, physical properties, etc.) of the soil sample are determined using a predictive model that relates the diffuse reflectance spectra and the elemental data to the one or more properties in block 218. The one or more properties of the soil sample are provided to one or more input/output interfaces in block 210. Non-limiting examples of the one or more properties of the soil sample are salinity, textural constituents, soil pH, soil carbon content or clay mineralogy. The scanning, receiving, determining and providing steps can be performed in situ. The foregoing method can be performed by a computer program embodied on a non-transitory computer readable medium.

Additional steps may include: (1) calibrating the predictive model; (2) placing the probe in contact with or proximate to the soil sample; (3) reducing dimensionality and qualitative discrimination of the diffuse reflectance data; (4) receiving a set of multispectral reflectance values related to the soil sample from a remote sensing device, and wherein the predictive model further relates the set of multispectral reflectance values to the one or more properties; (5) extracting the multispectral reflectance values from a satellite imagery using a soil and vegetation based indices; (6) retrieving the set of multispectral reflectance values from a memory or a data storage communicably coupled to the one or more processors; (7) determining a geographic location of the soil sample using a space-based satellite navigation system; (8) determining an elevation of the soil sample; and/or (9) any other desired step.

The present invention demonstrates that proximal or remotely sensed data can be efficiently used as a proxy for soil salinity assessment, which could result in substantial cost savings relative to traditional lab salinity measurements. However, soil salinity is only one example of how the present invention can be used. For example, the spectral and elemental datasets collected via scanning can be used for the prediction of multiple other soil parameters such as textural constituents (e.g., clay), soil pH, soil organic carbon content, and clay mineralogy whereas soil slurry or paste methods are useless in this regard. Other desired parameters can be determined using the present invention. The incorporation of ancillary PXRF elemental data and RS based multispectral reflectance values with VisNIR DRS spectra provide the best predictive ability; considerably better than each approach individually.

Various non-limiting examples of studies using the present invention will now be described: 1) surface soil salinity, 2) total carbon and total nitrogen, and 3) identification of petroleum contaminated soils. Other uses of the present invention will be apparent to those skilled in the art.

Surface Soil Salinity:

A study was conducted to evaluate the feasibility of the present invention using three different methods for predication surface soil salinity, namely remote sensing (RS), visible near infrared diffuse reflectance spectroscopy (VisNIR DRS), and portable x-ray fluorescence (PXRF) spectrometry. The study is described herein as a non-limiting example of the present invention. The objectives of the study were to: 1) collect a large number of soil samples representing a wide range of soil salinity, 2) evaluate the collected samples using both traditional laboratory methods (e.g., electrical conductivity of a 1 part soil to five parts water— EC (1:5) dS m$^{-1}$) as well as the newly proposed approaches described herein, 3) establish relationships between EC (1:5) and either proximally sensed (i.e. VisNIR and/or PXRF) and/or remotely sensed (i.e. Landsat 8) data, and 4) investigate the soil salinity predictability by using various statistically rigorous approaches (e.g., partial least squares regression (PLS)). Testing was also conducted to determine whether or not a multi-sensing approach is optimal using statistical measures such as regression coefficient ($R^2$) and prediction precision (RMSE).

Two saline playas were evaluated in West Texas, USA featuring 91 and 74 soils collected via random stratified sampling at 0-5 cm and representing a wide variety of soil salinity from high levels inside the playa bottoms to lower levels on the annulus and surrounding uplands. Samples were subjected to PXRF and VisNIR DRS scanning under laboratory conditions, and compared to Landsat spectral data and traditional laboratory analyses of salinity (e.g., 1:5 v/v suspensions). Results showed a broad range of EC (1:5) (0.028 to 43.41 dS m$^{-1}$). Derived from PXRF, both Cl and S were significantly, positively correlated with $\log_{10}$ transformed EC (1:5). VisNIR partial least squares prediction models produced strong residual prediction deviations (RPDs) of 2.49 to 2.91. Validation statistics of Savitzky-Golay support vector regression outperformed all other VisNIR models tested with an RPD of 3.1. While the performance of each technique produced variable success independently, combining the three techniques produced the highest predictability (RPD=3.35). With all three types of data (VisNIR DRS, PXRF, and RS) being quick and easy to collect, their synthesis in predictive models offers excellent potential for providing soil salinity measurements comparable to standard, laboratory derived data.

Figure 3A:
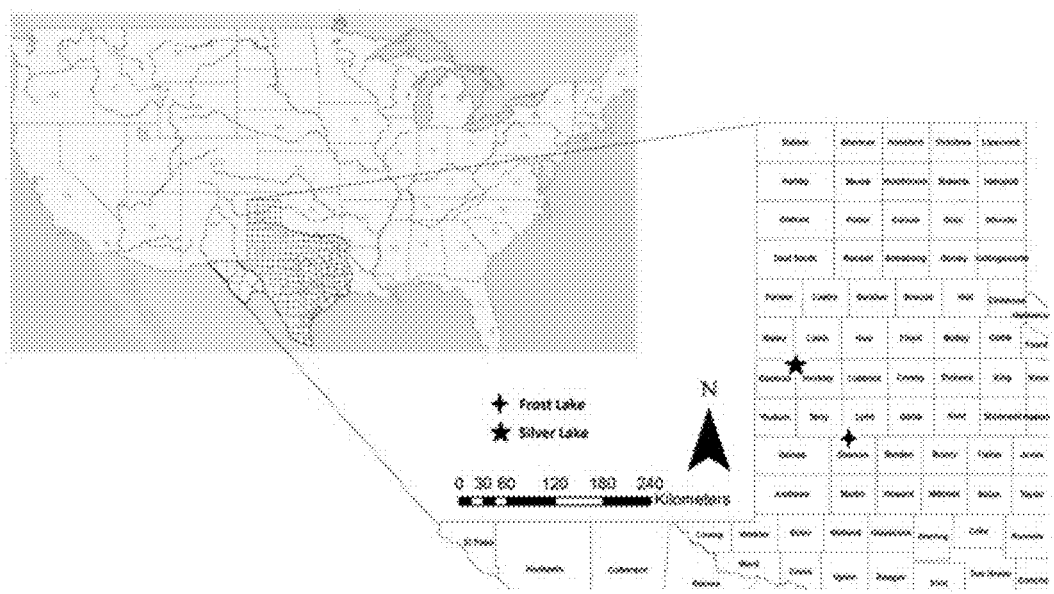
FIG. 3A is a map showing the location of two saline playas sampled in Northwestern Texas, USA.
Figure 3B:
FIGS. 3B and 3C are images of Frost Lake and Silver Lake, respectively.
Figure 3C:
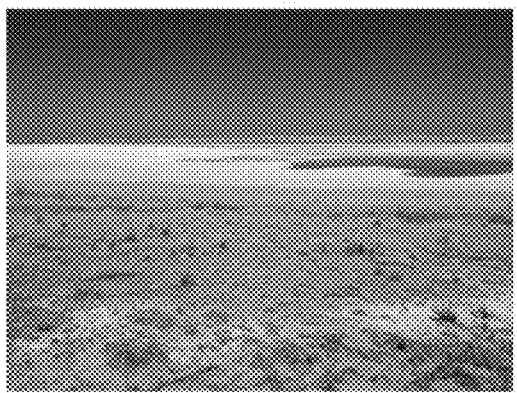

Two saline playas were sampled in January and February 2014 in Northwestern Texas, USA (32° 57' 22.74" to 32° 57' 46.85" N and 102° 0' 33.12" to 102° 0' 54.21" W) (FIG. 3A). The Silver Lake site (FIG. 3C) is located in the western Texas panhandle near the Texas/New Mexico border. It lies between the counties of Cochran and Hockley (~33.8° N; 102.6° W). The Frost Lake site (FIG. 3B) is located to the southeast some 100 km away and on the boundary between Lynn and Dawson counties (32.9° N; 102.0° W). Sampling was conducted following a prolonged dry period (both playas were mostly dry). A total of 165 soil samples were collected and used in regression analysis described below. These areas of Texas fall in Major Land Resource Area (MLRA) 77C: Southern High Plains—Southern Part. The area is characterized by a semi-arid climate with 405-560 mm annual precipitation, average annual temperature of 13 to 17° C., and a frost free period averaging 225 days yr$^{-1}$ [36]. The surface of this MLRA is covered primarily by aeolian deposits of the Blackwater Draw formation of Pleistocene age [36]. Lacustrine deposits of dolomite, with interbedded clastic sediments are also common and derived from the Blanco (Pliocene), Tule, Double Lakes, and Takoha (Pleistocene) formations [36]. Draws and insets also expose the Ogallala formation (Miocene-Pliocene) in some places. The Frost Lake playa covers an area of ~20 ha and is bisected by the Lynn-Dawson County line.

A total 91 surface (0-5 cm) soils were collected via random stratified sampling to include the playa basin, annulus, and surrounding upland. The Soil Survey Staff [37, 38] mapped the soils at Frost Lake mostly as water with upland surrounding areas characterized by the Arvana (Fine-loamy, mixed, superactive, thermic Petrocalcic Paleustalfs) and Cedarlake (Fine-loamy, mixed, superactive, calcareous, thermic Typic Halaquepts) soil series. The Silver Lake playa covers an area of ~88 ha and is bisected by the Cochran-Hockley County line. A total of 74 surface (0-5 cm) soils were collected via random stratified sampling to include the playa basin, annulus, and surrounding upland. The Soil Survey Staff [37, 38] mapped the soils at Silver Lake mostly as salt deposits with part of the playa mapped as a sanitary landfill, surrounded by Drake series (Fine-loamy, mixed, superactive, thermic Aridic Calciustepts) dunes. At each site, soils were sampled with small hand shovel and placed in sealed plastic bags for transport back to the laboratory. The location of all sampling sites was georeferenced with a Garmin e-Trex (Garmin Ltd., Schaffhausen, Switzerland) global positioning system receiver (location error approx. ±5 meters).

Two types of remotely sensed data were used in this study to facilitate comparison to standard laboratory analysis. First, Landsat imagery was queried for the areas that cover the two saline playas; Frost Lake and Silver Lake. Second, digital elevation model (DEM) data was used to assess topographic variability at the study sites.

The two 2014 Landsat 8 images covering the two playas were as follows: path 30; row 37 for Frost Lake, and path 31; row 36 for Silver Lake [42]. The two DEM datasets, ASTGTM2_N32W103 and ASTGTM2_N33W103 for Frost Lake and Silver Lake, respectively, were obtained from National Aeronautics and Space Administration (NASA) [27].

The digital number (DN) values of Landsat 8 images and the corresponding elevations from the DEM were extracted by point using the spatial analyst tool in ArcGIS 10.2 (ESRI, The Redlands, Calif., USA). Specifically, Landsat imagery bands 2 to 8 were used for comparison to laboratory derived soils data. Statistically, the extracted values from Landsat imagery and DEMs were correlated to the standard laboratory analysis data for soil salinity (EC 1:5 v/v) via support vector regression.

Soil analyses were conducted in the Texas Tech University Pedology Laboratory in Lubbock, Tex., USA. Upon arrival, samples were air dried and lightly ground to pass a 2 mm sieve prior to all other analyses. Soil EC (1:5) was determined in a 1:5 (v/v) soil water slurry using 20 g soil and 100 ml MilliQ™ (18.2 MΩ) (Merck Millipore, Billerica, Mass., USA) water. Samples were shaken for 1 h and allowed to settle for 30 min prior to analysis per Loveday [24] and Rayment and Higginson [30]. Salinity measurements were made using an YSI Model 30 salinity, conductivity, and temperature system (Yellow Springs, Ohio, USA).

For each air-dried sample, PXRF scanning was conducted with a DP-6000 Delta Premium® PXRF (Olympus, Waltham, Mass., USA). The instrument features a Rh x-ray tube operated at 10-40 kV with integrated large area silicon drift detector (165 eV). Prior to scanning, the instrument was calibrated with a '316' alloy calibration clip tightly fitted over the aperture. The instrument was operated in Soil Mode (3 beam) which is capable of detecting the following suite of elements: V, Cr, Fe, Co, Ni, Cu, Zn, Hg, As, Se, Pb, Rb, Sr, Zr, Mo, Ag, Cd, Sn, Sb, Ti, Mn, P, S, Cl, K, and Ca; each sample was then scanned a second time using Geochem Mode (2 beam) such that Mg was obtained. Scanning for Soil and Geochem Modes was conducted at 30 s per beam. Geochem scans were conducted in triplicate and averaged, with the spectrometer repositioned between each scan. Soil Mode scans were conducted once on each sample; yet each individual scan was an average of internal scans taken at 1 sec intervals.

In the laboratory, the 165 air-dried soil samples were scanned using a PSR-3500® portable VisNIR spectroradiometer (Spectral Evolution, Lawrence, Mass., USA) with a spectral range of 350 to 2500 nm. The spectroradiometer had a 2-nm sampling interval and a spectral resolution of 3.5, 10, and 7-nm from 350 to 1000 nm, 1500 nm, and 2100 nm, respectively. Scanning was facilitated with a contact probe featuring a 5 W built-in light source. Samples were allowed to assume room temperature (25° C.), evenly distributed in an opaque polypropylene sample holder and scanned from the top with the contact probe connected to the PSR-3500® with a metal-clad fiber optic cable. Full contact with the sample was ensured to avoid outside interference. Each sample was scanned four times with a 90° rotation between scans to obtain an average spectral curve. Each individual scan was an average of 10 internal scans over a time of 1.5 seconds. The detector was white referenced (after each sample) using a 12.7 cm×12.7 cm NIST traceable radiance calibration panel, ensuring that fluctuating downwelling irradiance could not saturate the detector.

Raw reflectance spectra were processed via a statistical analysis software package, R version 2.11.0 (R Development Core Team, 2008) using custom "R" routines [11]. These routines involved (i) a parabolic splice to correct for "gaps" between detectors, (ii) averaging replicate spectra, (iii) fitting a weighted (inverse measurement variance) smoothing spline to each spectra with direct extraction of smoothed reflectance at 10 nm intervals.

This study used four spectral pretreatments to prepare the smoothed soil spectra for analysis, and two multivariate algorithms to develop the VisNIR predictive models. Spectral pretreatments helped in reducing the influence of the side information contained in the spectra. The pretreatment transformations applied were—raw reflectance, Savitzky-Golay (SG) first derivative using a first-order polynomial across a ten band window, multiplicative scatter correction (MSC), standard normal variate transformation followed by detrending (SNV-DT), log (1/reflectance) or absorbance (ABS), and normalization by range (NRA). Barnes et al. proposed SNV-DT to remove multiplicative interferences of scatter and particle size and to explain the difference in baseline shift and curvilinearity in diffuse reflectance spectra. [4] SNV, which is also known as z-transformation or centering and scaling [28], normalizes each spectrum $\rho$ to a zero mean and unit variance by subtracting the mean of this spectrum $\rho'$ and dividing the difference by its standard deviation $\sigma\rho$ (Eq. 1):

$$SNV=(\rho-\rho')/\sigma_\rho \qquad (1)$$

This is followed by a detrending step which is a 2nd-order polynomial fit to the SNV transformed spectrum and subtracted from the original spectrum to correct for wavelength-dependent scattering effects [8]. All pretreatment transformations were implemented in the Unscrambler® X 10.3 software (CAMO Software Inc., Woodbridge, N.J.). All four spectra were included as candidate explanatory variables for EC (1:5) in subsequent VisNIR models.

For each VisNIR spectral pretreatment, two multivariate methods tested were partial least squares regression (PLS) and support vector regression (SVR) [18, 44]. Since the original site wise EC (1:5) values were non-normally distributed (p>0.05) and highly influenced by outliers, Box-Cox transformation [6] was applied to the original EC data using $\lambda=0$ ($\log_{10}$-transformation) to bring the data to a Gaussian distribution. Both PLS and SVR models were developed based on $\log_{10}$-transformed ($\lambda=0$) EC (1:5) values. As implied by its name, the solution of the support vector methods, which can be solved through quadric programming, often depends on a small subset of samples in the data, which are called support vectors. The support vector methods have demonstrated superior performances and can be easily extended to nonlinearly transformed feature space via a technique called the "kernel trick". Subsequently, the linear SVR is applied on that high-dimensional space. Although the boundary for linear SVR on that high-dimensional space is linear, when it projects back to its original space, it becomes nonlinear. In the present study, the epsilon SVR was used with linear kernel and one cross validation (LOOCV) for the SVR was left out. The PLS model was developed with LOOCV to relate the variation in EC (1:5) to the variation in a multi-component variable (e.g., wavelength).

Figure 4:
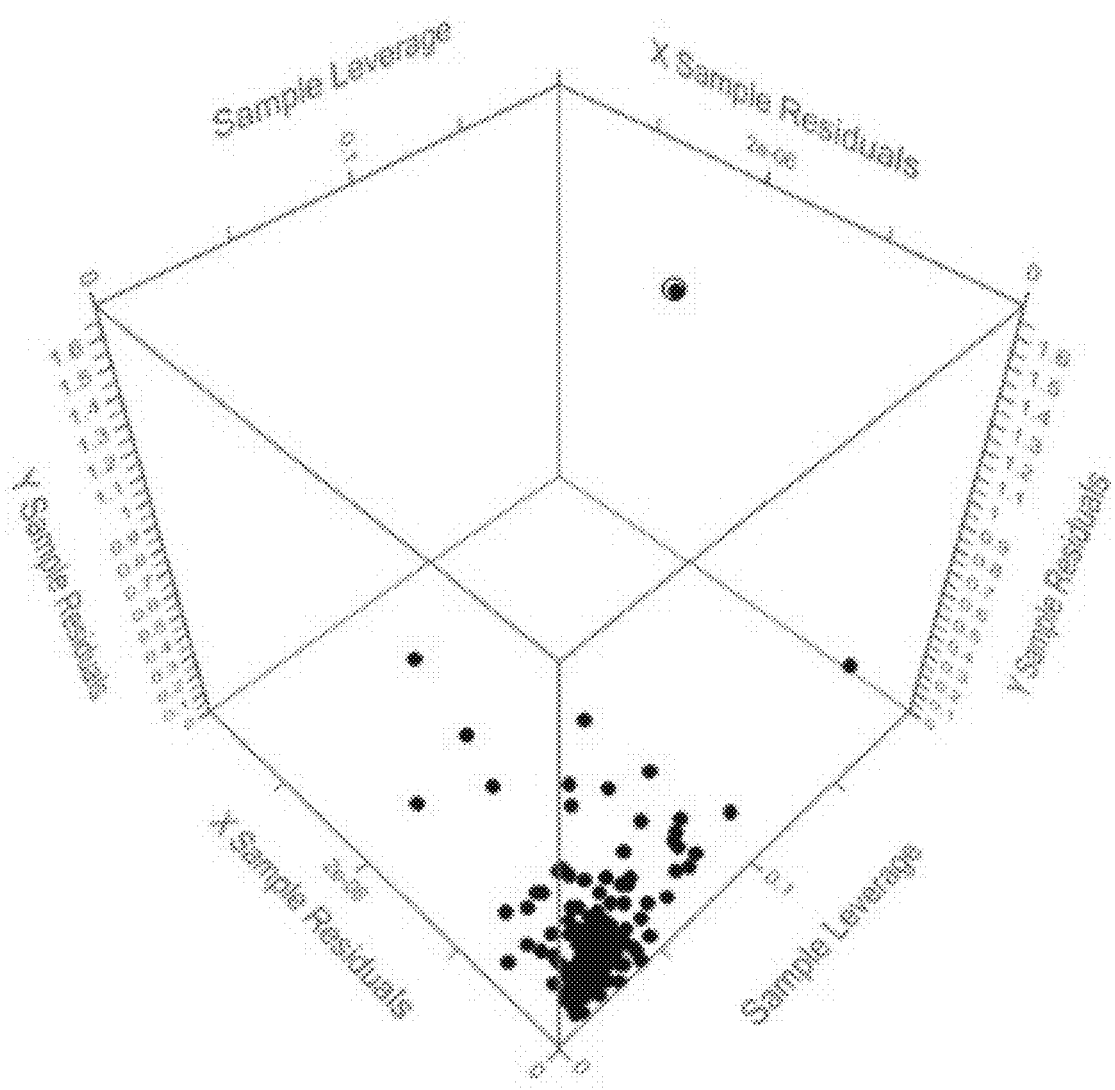
FIG. 4 is a plot showing the detection of outliers after partial least-squares regression analysis in accordance with one embodiment of the present invention.

The optimum number of PLS latent factors (rotations of principal components for a slightly different optimization criterion) was selected on the basis of the number of factors with the smallest total residual validation Y-variance or highest total explained validation Y-variance (CAMO Software Inc., Woodbridge, N.J.). During PLS model calibration, influence plots were created a priori for excluding influential X- and Y-outliers (FIG. 4: A potential sample outlier, marked in circle, is shown as an example). These plots were created by plotting the residual X and Y-variances against leverages. Samples with a high leverage and high residual X- or Y-variance were considered as potential outliers (CAMO Software Inc., Woodbridge, N.J.). Next, the projected influence plots were used to verify those samples with high residuals. However, the outliers were carefully examined by marking them one-by-one and plotting the X-Y relation outliers for several model factors to monitor their influence on the shape of the X-Y relationship.

Moreover, SVR models were developed for correlating soil EC (1:5) with PXRF metal data and Landsat image extracted reflectance values for both sites. Note that, initially only five elements (S, Cl, Ca, Mg, and K) were considered for PXRF model calibration. The coefficient of determination ($R^2$), RMSE, and residual prediction deviation (RPD) [49] were used as rubrics for judging model generalizing capability (See [12] for details). Finally, all three approaches (concatenating the best performing VisNIR spectral treatment, PXRF sensed elements, and Landsat band reflectance values) were combined to investigate if they could together improve soil EC (1:5) predictability.

Subsequently, principal component analysis (PCA) was employed for dimensionality reduction and qualitative VisNIR discrimination of the inherently different soil samples for best performing spectral pretreatment. Pairwise scatterplot of the first two PCs provided a visual assessment of how different saline soils from the two sites were, separated in the PC space. PCA was performed using R version 2.11.0 and the function 'prcomp'. Other statistical analyses were done in XLStat version 2014 (Addinsoft, Paris, France).

To validate the results, x-ray diffraction (XRD) and scanning electron microscopy coupled with energy-dispersive x-ray spectroscopy (SEM/EDS) were used to investigate mineralogical and elemental composition. Four samples with different levels of salinity (the highest and lowest content) were selected for analyses.

Representative aliquots of each sample (<2 mm grain size) were split into two subsamples. As for XRD analysis, subsamples were crushed and ground by hand with an alumina/agate mortar and pestle to a grain size of less than 5 μm to mitigate the well-known effects of preferred orientation on powder x-ray diffraction data; such effects are notable in the analysis of phyllosilicate phases, especially clay minerals. Powdered samples were packed into a standard back-fill powder diffraction sample holder. Powder XRD data was collected from 3 to 70° 2θ with a Rigaku Miniflex X-Ray diffractometer (Rigaku Corporation, Tokyo, Japan) using Cu Kα radiation ($\lambda$=1.54187 Å). Intensities were measured at 0.05° steps with counting times of 1.25° per minute. Phase identification (i.e. pattern matching) of the XRD data was carried out using the Rigaku PDXL software and the International Center for Diffraction Data 2010 PDF-2 database.

For SEM/EDS analysis, representative aliquots of samples were mounted on a standard 8 mm aluminum SEM stub. The stub was inserted into a Hitachi SN-4300 scanning electron microscope SEM (Hitachi Ltd., Chiyoda, Tokyo, Japan) with a Schottky Field Emission source. The microscope was operated in variable pressure mode (150 to 200 Pa) using an emission current of 53 nA and an accelerating voltage of 12 or 15 kV. Secondary electron (SE) images were collected using an Environmental Secondary Electron Detector (ESED), and back-scattered electron images were collected with a YAG detector. Qualitative compositional information on elements present in representative regions of samples were collected using an Oxford ISIS Energy Dispersive Spectrometer featuring an ultrathin window detector and operated with EDAS Genesis software. Each soil sample was randomly scanned at different scales of magnification.

Statistical moments related with soil salinity and its correlation with PXRF sensed elements are explained as follows: the EC showed a broad range from 0.028 to 43.41 dS m$^{-1}$ while log transformed EC (1:5) values ranged from −1.56 to 1.63 log$_{10}$ dS m$^{-1}$ (Table 2). These values were used as the dependent variable for subsequent PLS and SVR modeling (Table 3). Shacklette and Boerngen [33] established mean concentrations of 50 elements across the United States including total Ca, Mg, K, and S; which were compared to the PXRF readings for Ca, Mg, K, and S in the current study samples (Table 2). Additionally, the latter mean values were compared to the average of total Ca, Mg, K, and S concentrations of Vinogradov [45], calculated based on worldwide samples. While the mean PXRF K reading of targeted soil samples (1.18%) was lower than averages of the abovementioned studies, averages of other elements were substantially higher, likely related to the high salt contents of the studied soils.

TABLE 2

Descriptive statistics for PXRF sensed elements along with EC (1:5)

| Statistic | S % | Cl % | K % | Ca % | Mg % | EC (dS m$^{-1}$) | Log$_{10}$ EC (1:5) (log$_{10}$ dS m$^{-1}$) |
|---|---|---|---|---|---|---|---|
| No. of Observations | 165 | 165 | 165 | 165 | 165 | 165 | 165 |
| Minimum | 0.156 | 0.024 | 0.144 | 0.199 | 0 | 0.028 | −1.561 |

TABLE 2-continued

Descriptive statistics for PXRF sensed elements along with EC (1:5)

| Statistic | S % | Cl % | K % | Ca % | Mg % | EC (dS m$^{-1}$) | Log$_{10}$ EC (1:5) (log$_{10}$ dS m$^{-1}$) |
|---|---|---|---|---|---|---|---|
| Maximum | 29.359 | 5.370 | 2.123 | 21.207 | 9.510 | 43.410 | 1.638 |
| 1$^{st}$ Quartile | 2.395 | 0.384 | 0.973 | 4.475 | 2.439 | 1.041 | 0.017 |
| Median | 7.705 | 0.756 | 1.209 | 7.463 | 3.280 | 5.895 | 0.770 |
| 3$^{rd}$ Quartile | 15.694 | 1.719 | 1.411 | 10.240 | 4.480 | 16.625 | 1.221 |
| Mean | 9.682 | 1.132 | 1.182 | 7.749 | 3.608 | 10.676 | 0.524 |
| Kurtosis | −0.702 | 1.275 | 0.599 | 0.231 | 1.110 | 0.201 | −0.731 |
| Skewness | 0.646 | 1.121 | −0.501 | 0.629 | 0.868 | 1.141 | −0.711 |
| Variance (n − 1) | 68.343 | 0.976 | 0.137 | 16.874 | 2.825 | 145.362 | 0.762 |
| Standard Deviation (n − 1) | 8.267 | 0.988 | 0.371 | 4.108 | 1.681 | 12.057 | 0.873 |
| Shaklette and Boerngen [33] (Mean) | 0.160 | — | 1.5 | 2.4 | 0.9 | — | — |
| Vinogradov (1979) (Mean) | 0.085 | — | 1.36 | 2.37 | 0.63 | — | — |

TABLE 3

Calibration and leave-one-out cross-validation statistics for different approaches employed for quantifying soil EC (1:5)

| Approach | Spectral Preprocessing[a] | PLS LF[b] | Model[c] | Calibration R$^2$ | RMSE (log$_{10}$ dS m$^{-1}$) | Validation R$^2$ | Validation RMSE (log$_{10}$ dS m$^{-1}$) | RPD[d] |
|---|---|---|---|---|---|---|---|---|
| VisNIR DRS | Raw | 9 | PLS | 0.91 | 0.258 | 0.88 | 0.299 | 2.91 |
| | | | SVR | 0.89 | 0.286 | 0.88 | 0.306 | 2.85 |
| | SG | 5 | PLS | 0.91 | 0.262 | 0.89 | 0.302 | 2.88 |
| | | | SVR | 0.95 | 0.196 | 0.90 | 0.280 | 3.10 |
| | MSC | 8 | PLS | 0.87 | 0.292 | 0.86 | 0.330 | 2.63 |
| | | | SVR | 0.90 | 0.276 | 0.88 | 0.300 | 2.90 |
| | SNV-DT | 8 | PLS | 0.90 | 0.278 | 0.87 | 0.316 | 2.75 |
| | | | SVR | 0.92 | 0.243 | 0.89 | 0.286 | 3.04 |
| | ABS | 9 | PLS | 0.88 | 0.305 | 0.84 | 0.350 | 2.49 |
| | | | SVR | 0.85 | 0.336 | 0.82 | 0.366 | 2.38 |
| | NRA | 8 | PLS | 0.89 | 0.289 | 0.86 | 0.332 | 2.62 |
| | | | SVR | 0.90 | 0.280 | 0.88 | 0.303 | 2.87 |
| PXRF | | | SVR | 0.72 | 0.475 | 0.71 | 0.485 | 1.79 |
| Landsat | | | SVR | 0.48 | 0.663 | 0.44 | 0.685 | 1.27 |
| Landsat + PXRF + VisNIR DNS | SG | | SVR | 0.95 | 0.185 | 0.91 | 0.260 | 3.35 |

[a]Raw, original reflectance; SG, Savitzky-Golay first derivative using a first-order polynomial across a ten band window; MSC, multiplicative scatter correction; SNV-DT, standard normal variate followed by detrending; ABS, log(1/reflectance); NRA, normalization by range.
[b]PLS LF, partial least squares regression latent factor.
[c]PLS, partial least squares regression; SYR, support vector regression.
[d]RPD, residual prediction deviation.

While scanning with PXRF, attempts were made to try to minimize known sources of error: 1) moisture, 2) sample homogeneity, and 3) inter-elemental interferences. Zhu et al. [50] noted that excessive (>20%) soil moisture degraded the accuracy of PXRF data. Specifically, when only dry sample scans were considered, the correlation between PXRF readings and laboratory measurements improved substantially. Another disadvantage of in-situ measurements is the degree of uncertainty caused by sample heterogeneity [3, 50]. Jones [20] noted that sample homogeneity is promoted when soils are dried and ground to pass a 2-mm sieve; practices followed as part of this study. Importantly, many salt impacted soils occur in naturally dry environments such as deserts where soil moisture would be nominal. Notwithstanding that, probably some amount of inter-elemental interferences could not be removed while their precise identification was beyond the scope of the study.

Figure 7A:
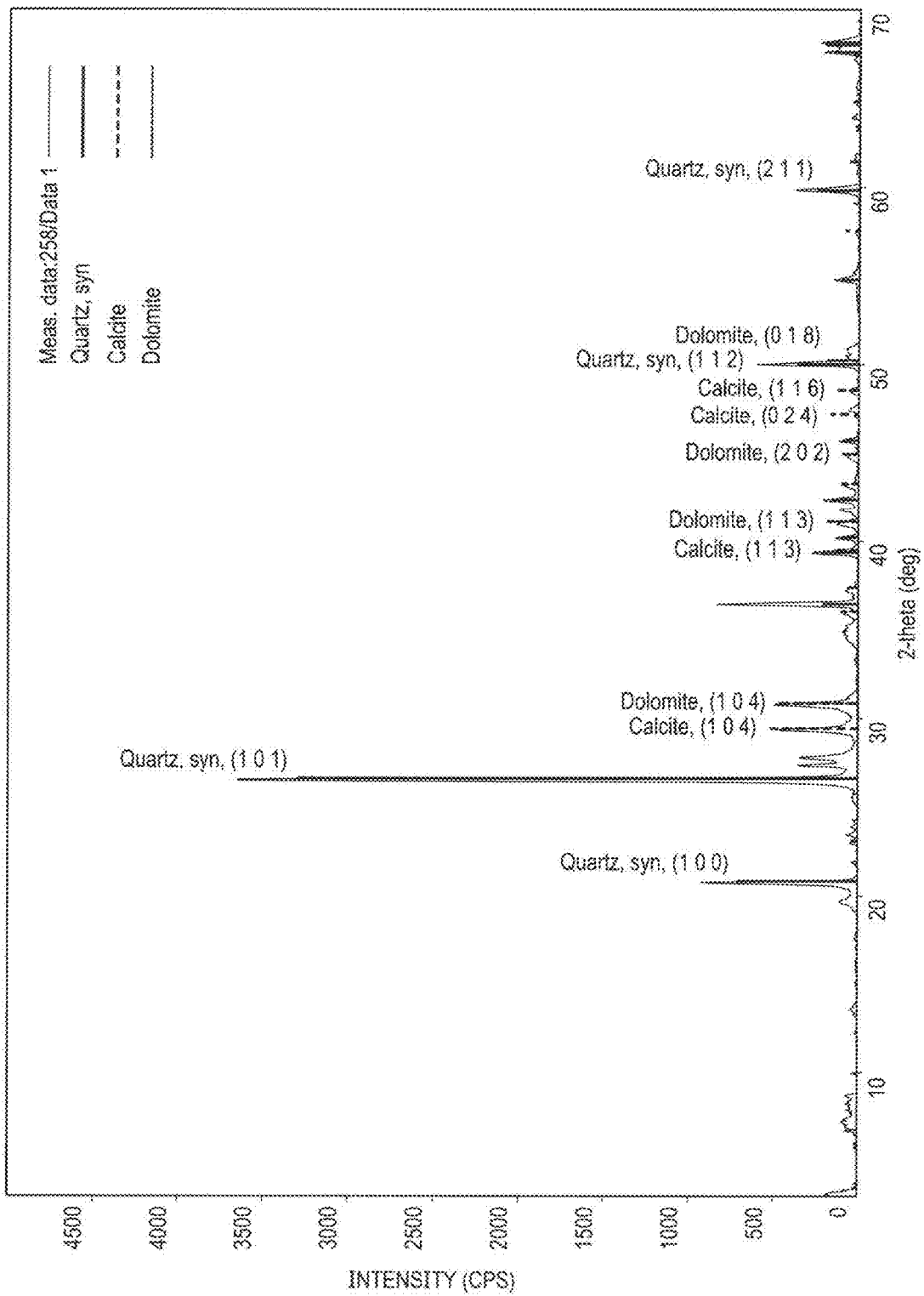
Figure 8A:
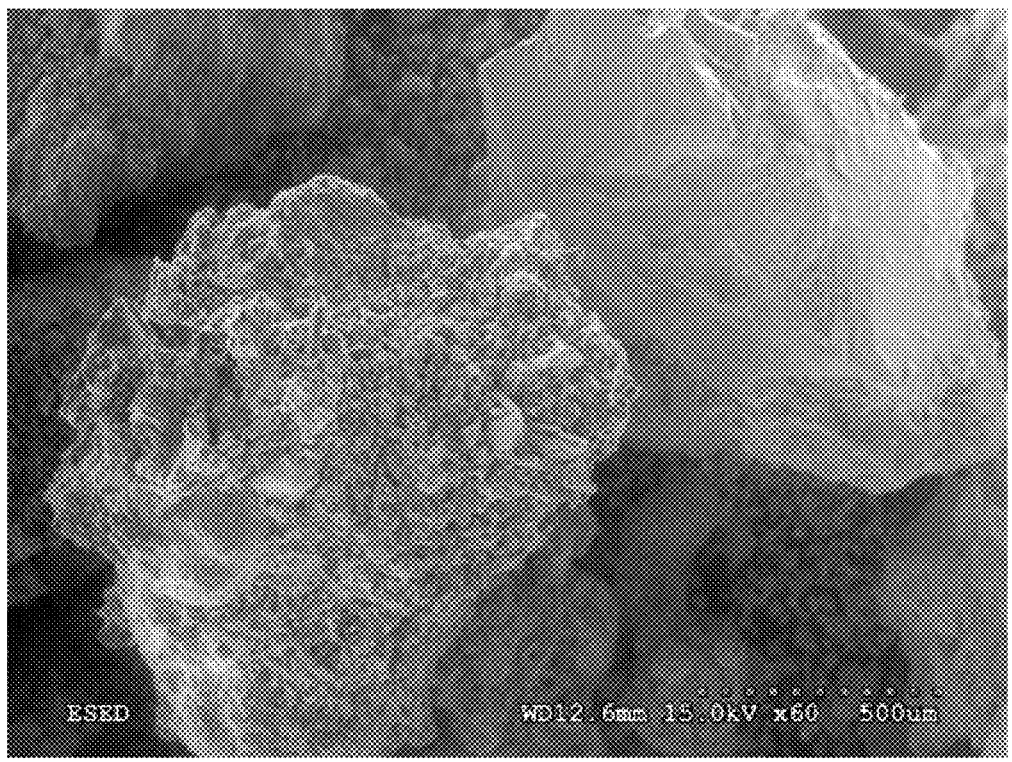
FIGS. 8A and 8B are images showing scanning electron microscopy of gypsum particle morphology from saline playas of West Texas, USA.
Figure 8B:
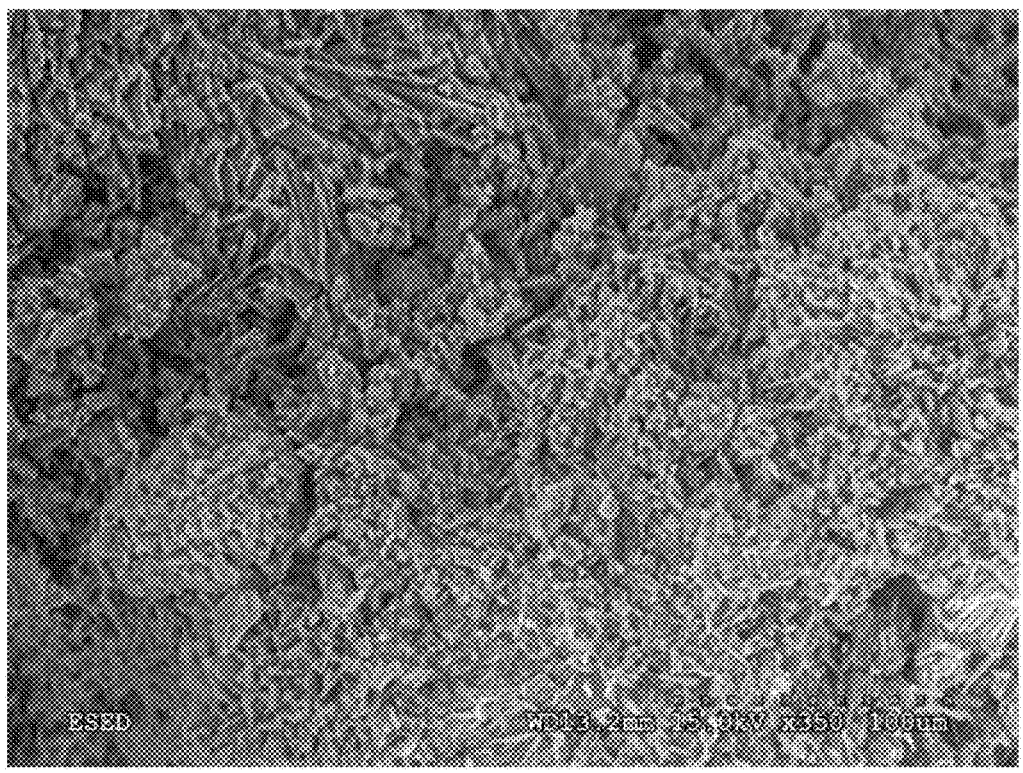
Figure 9A:
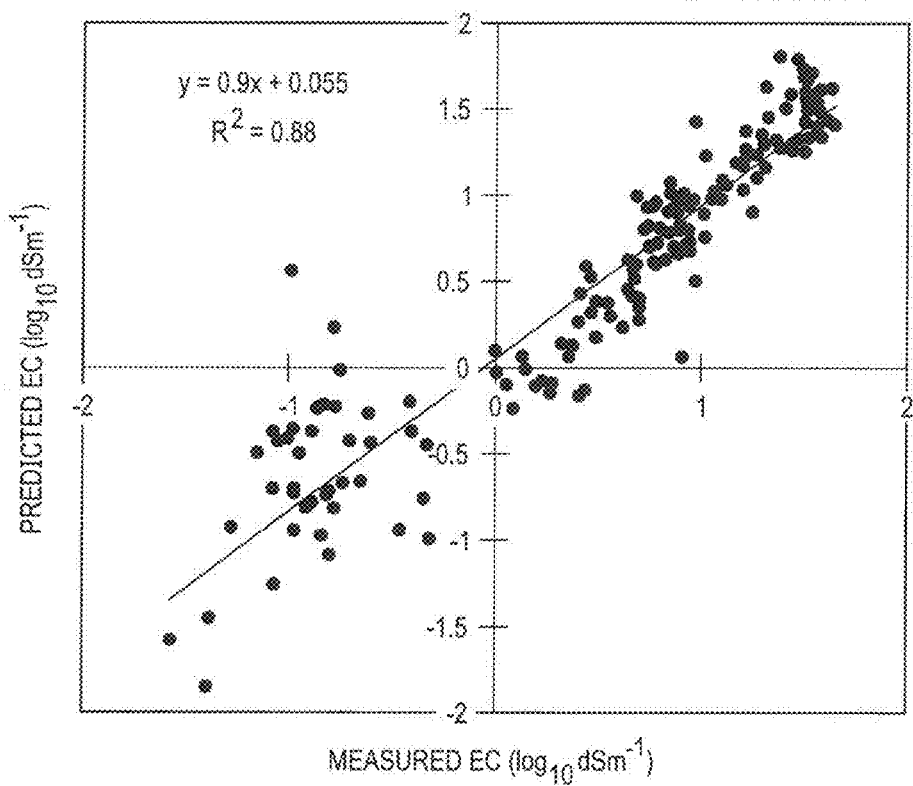
FIGS. 9A-9F are plots showing lab-measured vs. PLS predicted soil EC ($Log_{10}$ dS $m^{-1}$) using leave one out cross validation for Raw (FIG. 9A), SG (FIG. 9B), MSC (FIG. 9C), SNV-DT (FIG. 9D), ABS (FIG. 9E), and NRA pretreatment (FIG. 9F)
Figure 9B:
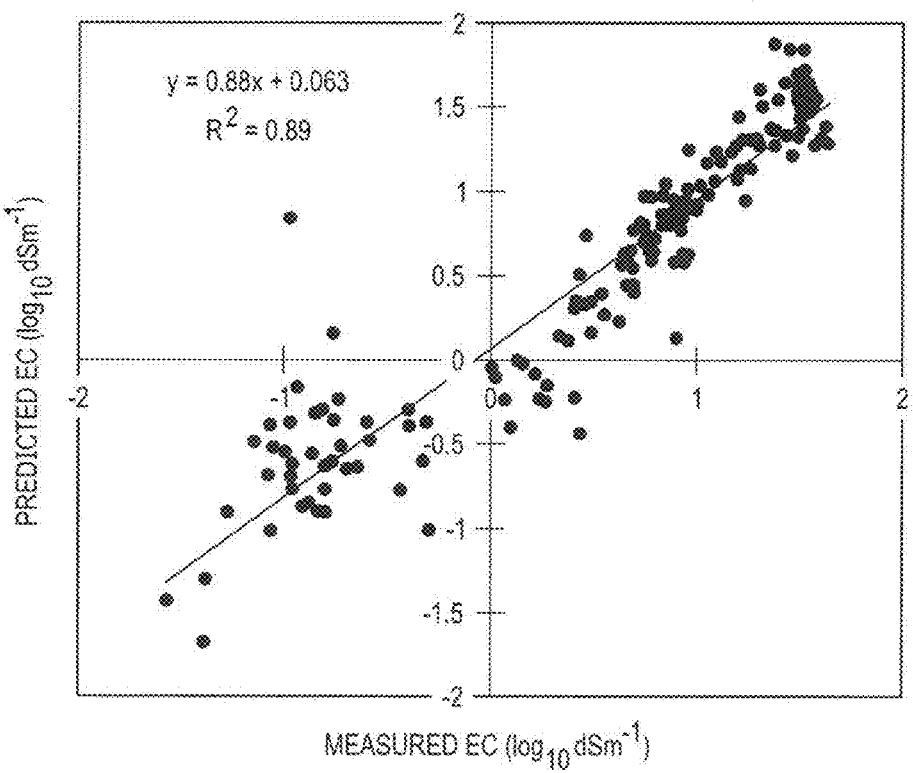
Figure 9C:
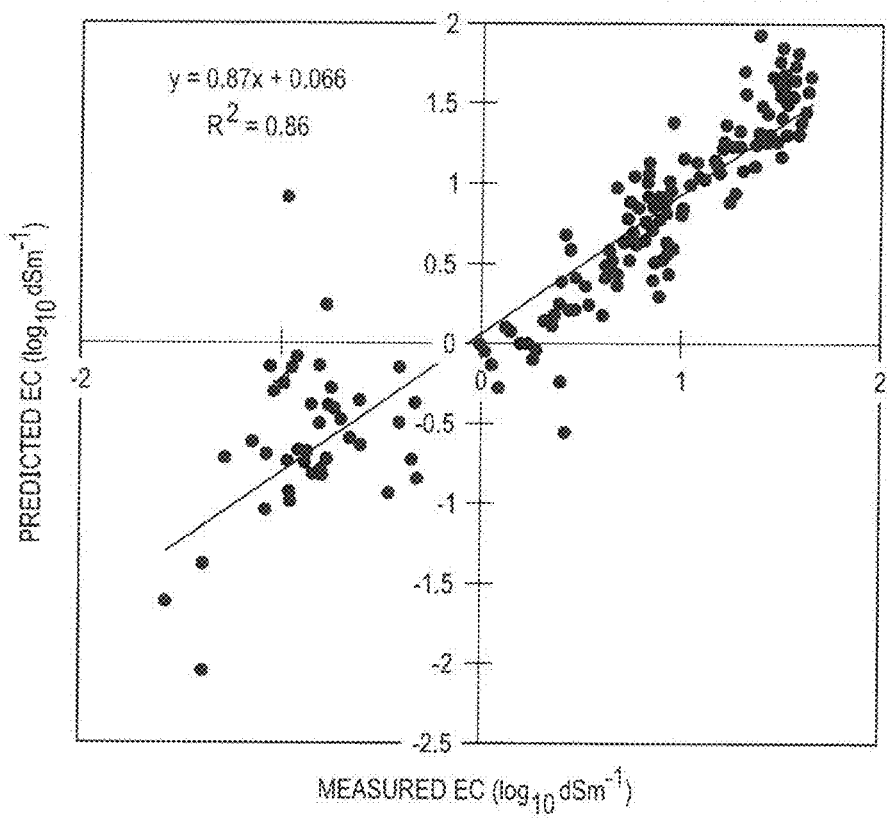
Figure 9D:
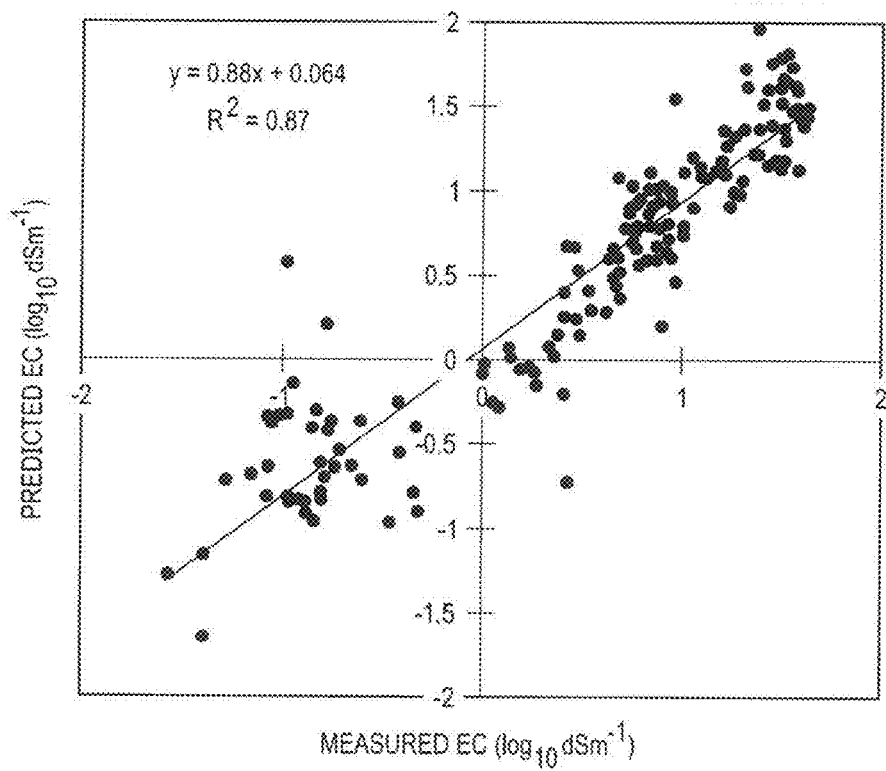
Figure 9E:
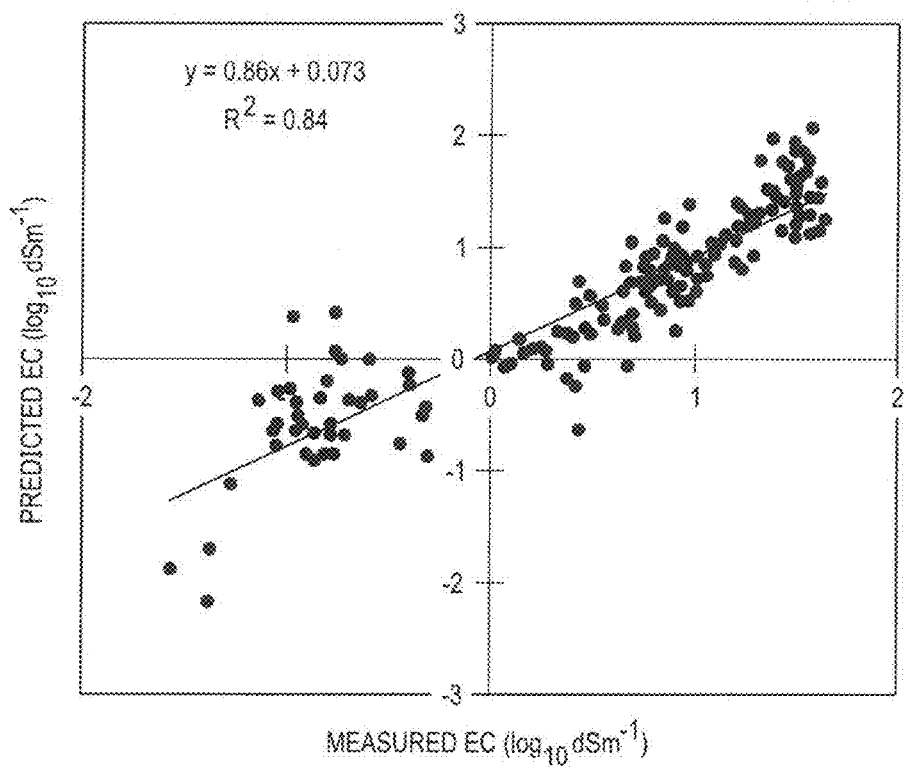
Figure 9F:
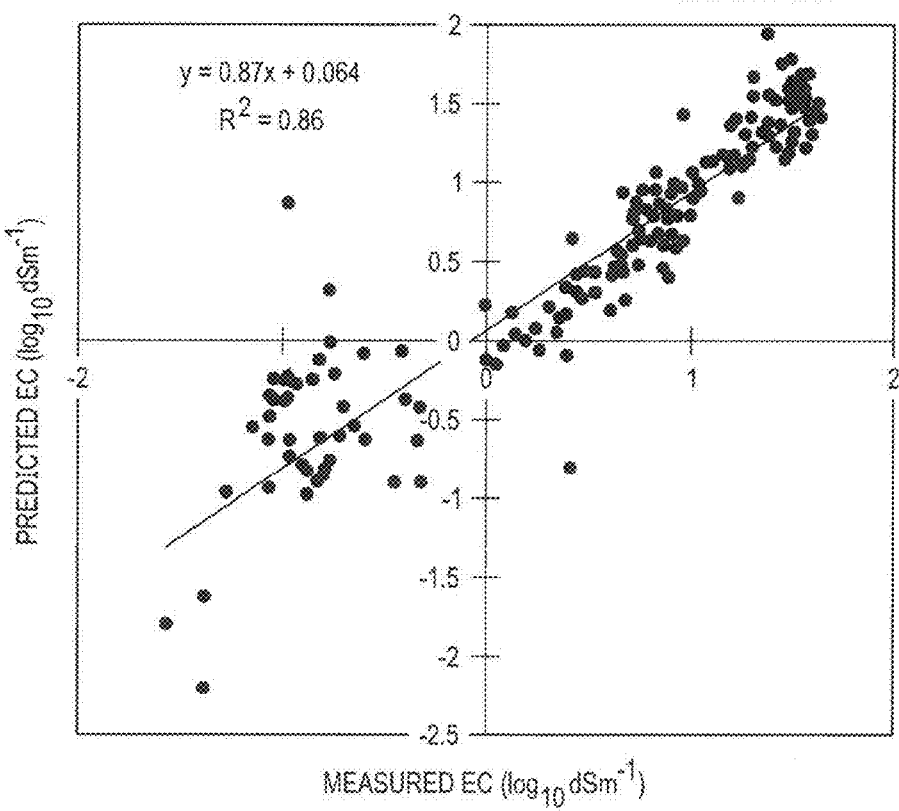
Figure 11A:
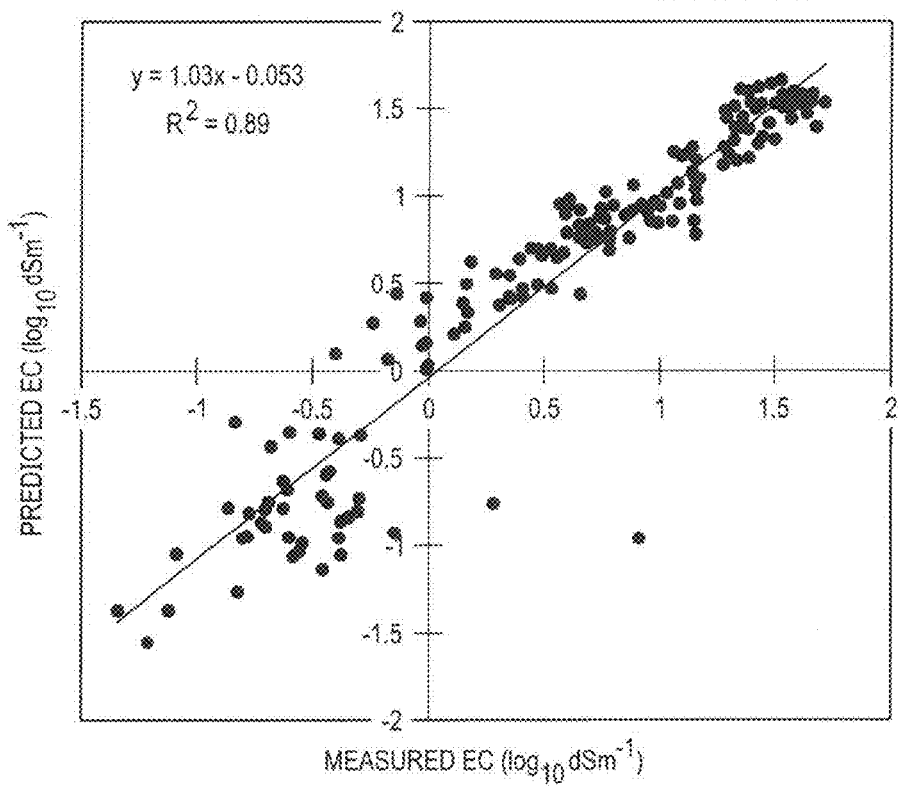
FIGS. 11A-11F are plots showing training models showing lab-measured vs. SVR predicted soil EC ($Log_{10}$ dS $m^{-1}$) for Raw (FIG. 11A), SG (FIG. 11B), MSC (FIG. 11C), SNV-DT (FIG. 11D), ABS (FIG. 11E), and NRA pretreatment (FIG. 11F)
Figure 11B:
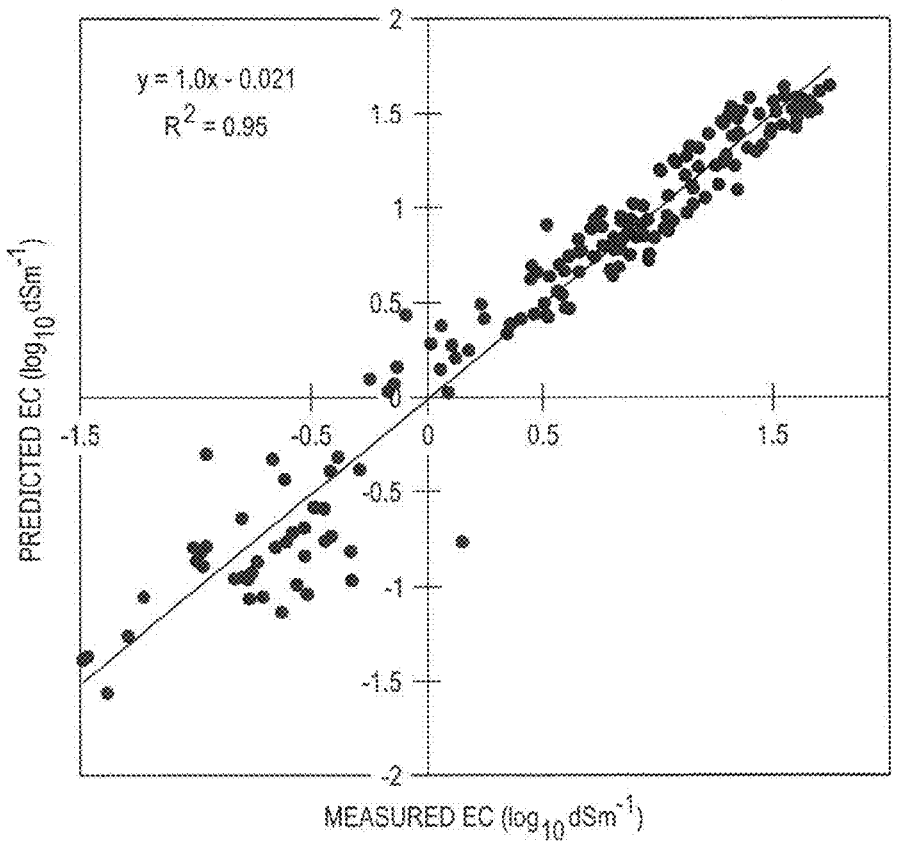
Figure 11C:
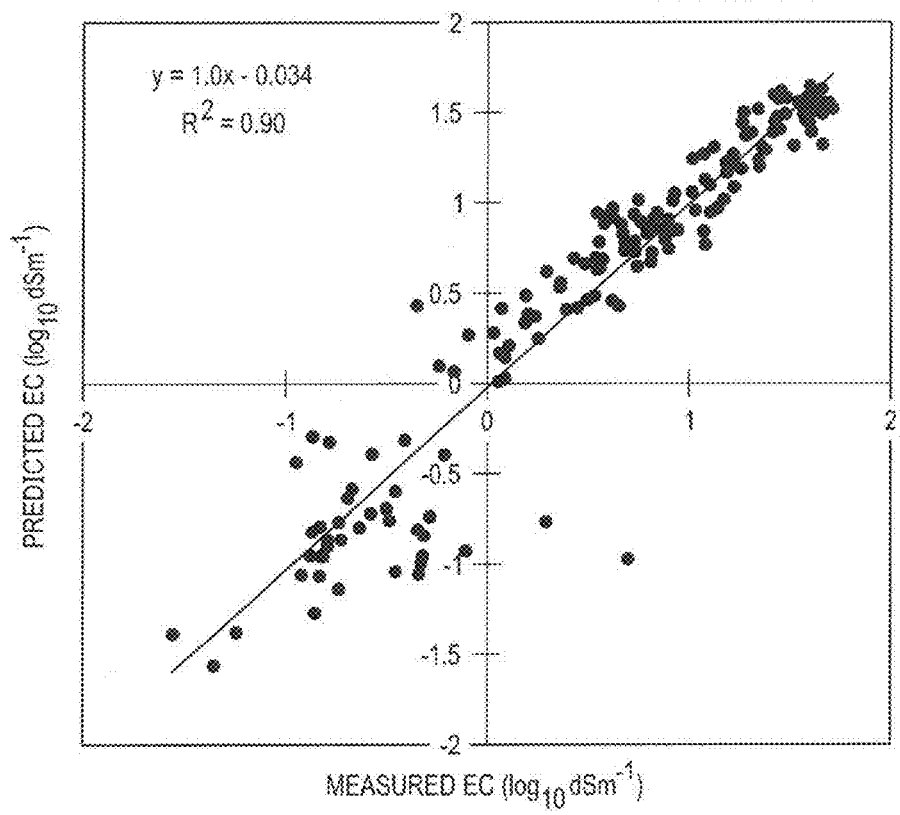
Figure 11D:
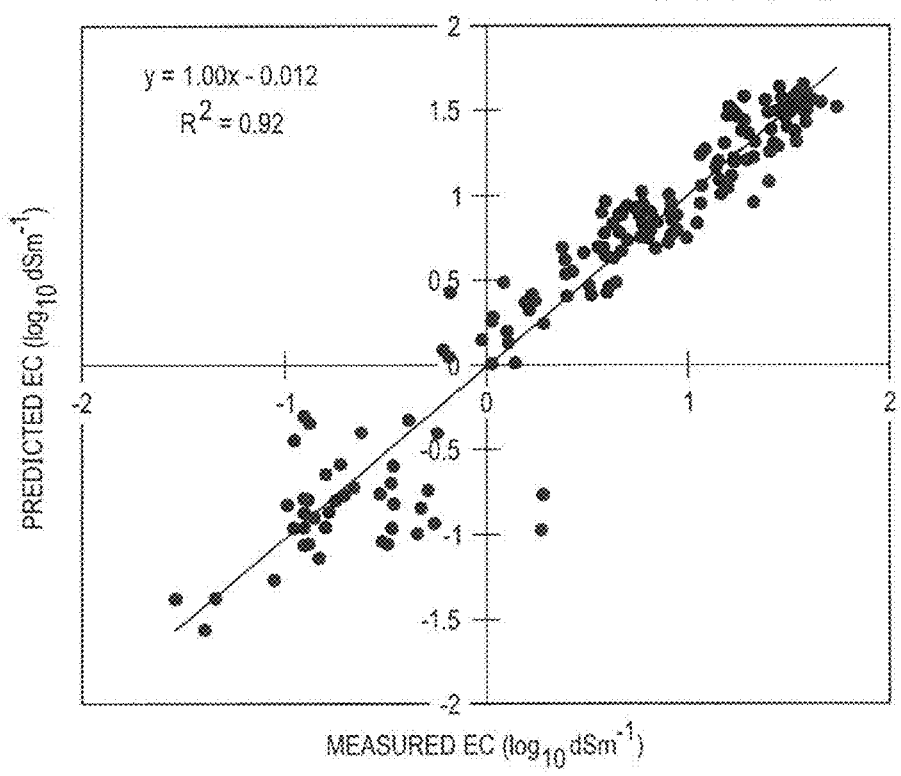
Figure 11E:
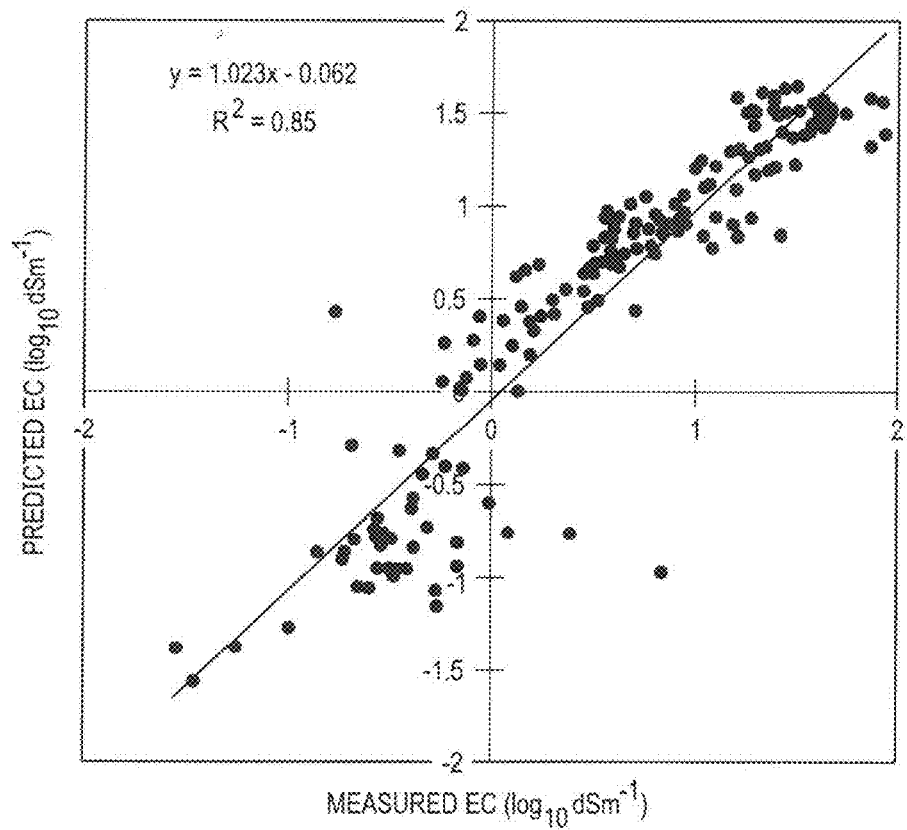
Figure 11F:
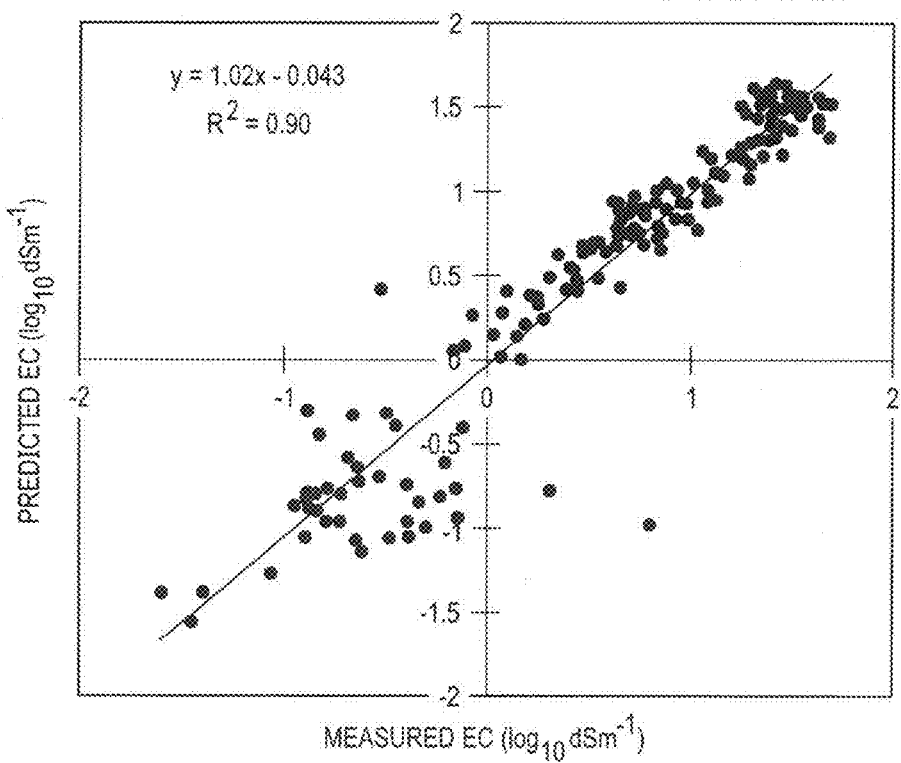

Multi element (Cl, K, S, Mg, and Ca) PXRF data was used for modeling soil EC (1:5). Though systems that offer electrostatic attraction to free cations in soil solution may effectively bind them to the exchange complex of clays or integrate them into the molecular structure of complex organics, anions such as Cl$^-$ would still be freely available as like charges repel each other. However, clays and organics may exchange/contribute cations to soil salinity, which would be reflected in higher overall soil EC (1:5), but not reflected by higher PXRF Cl readings, and not captured by simple linear regression with Cl as the single predictor element. However, only S (0.78) and Cl (0.60) were significantly positively correlated with log$_{10}$ transformed EC (1:5) (FIGS. 5A1-5G1), suggesting marked enrichment of SO$_4^-$ and Cl$^-$ salts. With respect to salinity assessment, current PXRF equipment is not able to quantify Na$^+$ directly, given its small, stable electron cloud. Nonetheless, the sensing of Cl⁻ salts by PXRF implied the probable occurrence of halite. This explanation was corroborated by XRD and SEM/EDS analyses (FIGS. 6A-6B, 7A-7B, and 8A-8B). For high salinity samples, mineralogical composition interpretation by XRD showed that the most common mineral types were then ardite ($Na_2SO_4$), blodite ($Na_2Mg(SO_4)_2(4H_2O)$), gypsum ($CaSO_4.2H_2O$), and halite (NaCl) (FIG. 6A). The non-saline samples contained mainly quartz alpha alpha ($SiO_2$) in addition to calcite and dolomite especially at Silver Lake (FIG. 7A).

Results of EDS showed that common elements related to high salinity samples are Na, S, O, Cl, Mg, Ca, K, and Al (FIG. 6B). Specifically, the prevalence of S and Cl was striking Conversely, non-saline samples showed a prevalence of Si, O, Al, K, Mg, and Ca (FIG. 7B). The correlation between $log_{10}$ transformed EC (1:5) and K, Mg, and Ca was not apparent and thus were excluded as predictors in the subsequent predictive models. This low correlation between latter elements and reference EC (1:5) can be attributed to the different degree of solubility of different compounds and to fact that not all dissolved solutes exist as charged species; and some of the ions merge to form less charged or even neutral ion-pairs, and therefore, add less proportionally to soil EC (1:5) than when fully dissociated [31]. Yet, both S and Cl exhibited higher CVs (85 and 87%, respectively) in sample sets, which showed that there were outliers for these two elements too. Results indicated that while a good negative curve-linear relationships between EC (1:5) and Ca and Mg was achieved for EC (1:5) values greater than 10 dS $m^{-1}$, the opposite was true for ED (1:5) values less than 10 dS $m^{-1}$. The relationship between EC (1:5) and K was rather poor (FIGS. 5A1-5G7).

Initially, among the two multivariate algorithms tested (PLS and SVR) with VisNIR spectral data, transformed EC (1:5) was estimated with slightly greater accuracy by SVR except for Raw and ABS (Table 3). Lab-measured versus PLS predicted EC (1:5) calibration models exhibited close $R^2$ values, ranging from 0.87 to 0.91 for all spectral pretreatments (Table 3). It was difficult to decide the optimal PLS calibration model. While the Raw reflectance based PLS calibration model with nine latent factors gave a $R^2$ of 0.91 and an RMSE of 0.258 $log_{10}$ dS $m^{-1}$, the SG model utilized five latent factors to produce the same $R^2$ (0.91) with non-significantly (randomization t-test p-values<0.01) higher RMSE of 0.262 $log_{10}$ dS $m^{-1}$. Therefore, the latter should be considered rather parsimonious [43, 46]. The prediction quality was judged by generalization capability (validation $R^2$, validation RMSE, and RPD) with LOOCV. RPD is the ratio of standard deviation and RMSE. Consequently, model predictability increases when validation set standard deviation (SD) is comparatively larger than estimation error (RMSE). Chang et al. [13] categorized the accuracy and stability of their spectroscopy models based on the RPD values of the validation set. While RPDs greater than 2.0 were considered stable and accurate predictive models; RPD values between 1.4 and 2.0 indicated fair models that could be improved by more accurate predictive techniques. Moreover, RPD values less than 1.4 indicated poor predictive capacity. Conversely, Saeys et al. [32] concluded that a value for $R^2$ between 0.66 and 0.80 signifies approximate quantitative predictions, while a value for $R^2$ between 0.81 and 0.90 reveals good prediction. Besides, calibration models having $R^2$ greater than 0.90 are considered to be excellent. Regarding the RPD statistic, a RPD less than 2 is considered insufficient for applications, while a value for RPD between 2 and 2.5 makes fairly accurate quantitative predictions possible. For values between 2.5 and 3, predictions can be classified as good; a RPD greater than 3 indicates excellent prediction.

In this study, successful prediction of soil EC (1:5) with RPDs ranging from 2.49 to 2.91 for PLS models confirmed the findings of Viscarra Rossel et al. [46] that infrared spectroscopy is a promising tool for estimating soil EC (1:5). However, the parsimonious SG model exhibited both stability and robustness with an RPD of 2.88 and a validation $R^2$ of 0.89 which could be attributed to its ability to smooth the spectra prior to calculating the derivative, ultimately decreasing the detrimental effect on the signal-to-noise ratio. This effect perhaps helped in increasing subsequent model's generalization capability. Additionally, MSC produced a validation $R^2$ of 0.86 by correcting differences in the base line and in the trend. This produces transformed spectra analogous to the original spectra which together lead to easier optical elucidation. Given that, the consistency of a NIR spectroscopic model is normally restricted to the range of parameter values, the wide range of soil EC (1:5) values (−1.56 to 1.63 $log_{10}$ dS $m^{-1}$) perhaps contributed to the overall satisfactory results.

Validation plots of observed vs. PLS predicted EC (1:5) for all spectral pretreatments are presented in FIG. 9A-9F. In general, PLS predictions of EC (1:5) for all pretreatments closely approximated the 1:1 line (the slope of the regression line was not substantially different from 1) and had less average bias (0.002 $log_{10}$ dS $m^{-1}$) than their SVR counterparts (0.024 $log_{10}$ dS $m^{-1}$, on average). All model biases were negligible than corresponding MSEs. Thus, model biases were accounted for a very trivial part of the overall lack of fit. Hence, model inaccuracy could be mainly attributed to a lack of correlation with regression line near unity. The weighted regression coefficients for both raw reflectance and SG based PLS models were plotted to elucidate the importance of the spectral pretreatments (FIGS. 10A-10B). The magnitude of the regression coefficient at each wavelength is proportional to the height of the bar. Wavebands with non-significant coefficients (P>0.05), as indicated by Tukey's jack-knife variance estimate procedure, are shown as thick, blue bars. All plots are on the same x axis. Note that, spectral variables with a large regression coefficient play an important role in the regression model. While a positive coefficient shows a positive link with the response (soil EC (1:5), in this study), a negative coefficient shows a negative link. Predictors with a small coefficient are considered as negligible. Although the number of important wavelengths did not vary significantly between raw (89) and SG based model (91), SG treatment appeared to remove negative spectral interferences in the raw untreated spectra originating from the ~350-425 nm and ~1340-1400 nm regions (Marked by A and B, respectively). Spectral interference from 350-425 nm could possibly arise from electronic transitions of the Fe3+ in the goethite or hematite component of iron oxides [19]. Moreover, the ~1340-1400 nm region gave an indication of O—H bonds in the hydroxyl or clay minerals, such as smectite and illite [48]. Although samples were air-dried, the masking effect from water was somewhat expected, and, indeed, has been observed at the ~1850-1900 nm region of raw reflectance spectra [9]. However, the large and important positive coefficients in the abovementioned region were clearly reduced in SG spectra, suggesting that higher spectral pretreatment was able to somewhat eliminate the influence of water.

Selecting appropriate pretreatment is a key factor in spectroscopic modeling. If, for instance, the dataset of interest does not follow Lambert-Beer's law, extra latent factors in PLS regression can frequently compensate for this non-ideal behavior of the spectral predictor, ultimately increasing model complexity and, in turn, reducing the model robustness for future predictions [25]. All spectral pretreatments aim to enhance the feature sought in the spectra, often a linear relation with the constituent of interest (EC (1:5) in this study) by reducing the un-modeled variability in the data. However, one must use caution since too severe pretreatment can sometimes remove the valuable information.

While considering the calibration generalizing capability, all SVR training models outweighed their PLS counterparts except for raw ($R^2$=0.89) and ABS($R^2$=0.85) and produced strong correlations to traditional lab analysis (FIGS. 11A-11F). Note that the prediction deteriorates considerably and also has a slight bias, a tendency to over-predict with decreasing EC (1:5) content. Validation statistics revealed that SG-SVR outperformed all other VisNIR models tested (RPD=3.1), producing high predictability. The other SVR model which exhibited similar high RPD used SNV-DT spectra (RPD=3.04).

Clearly, differences observed in the results, particularly in terms of RPD obtained in all cases by application of PLS or SVR were considered to be crucial. However, in depth elucidation of these differences would require the study of a larger number of samples with a better control of the factors that can influence these differences. Yet, it is possible to conclude that at least in the analysis soil EC (1:5), SVR provided quantitative results of similar quality if not better to those provided by the application of PLS.

Figure 12A:
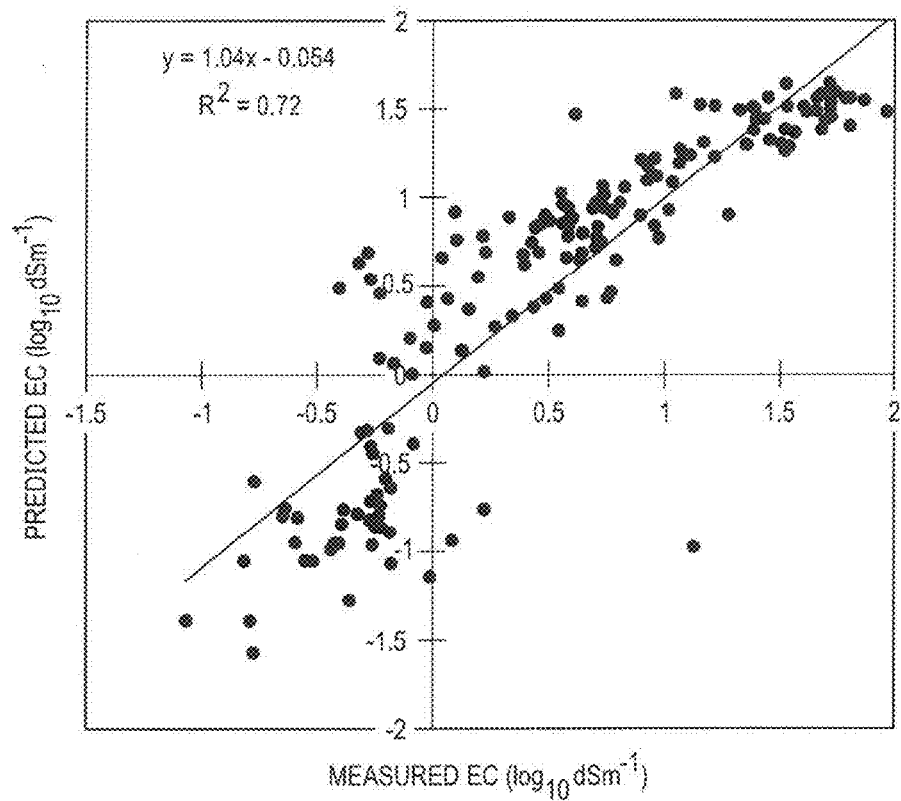
FIGS. 12A-12D are plots showing training models showing lab-measured vs. SVR predicted soil EC ($Log_{10}$ dS $m^{-1}$) for PXRF alone (FIG. 12A), RS alone (FIG. 12B), VisNIR (SG)+PXRF+RS (FIG. 12C), and VisNIR spectral separation of samples from the two sites via Principal Component Analysis (FIG. 12D)
Figure 12B:
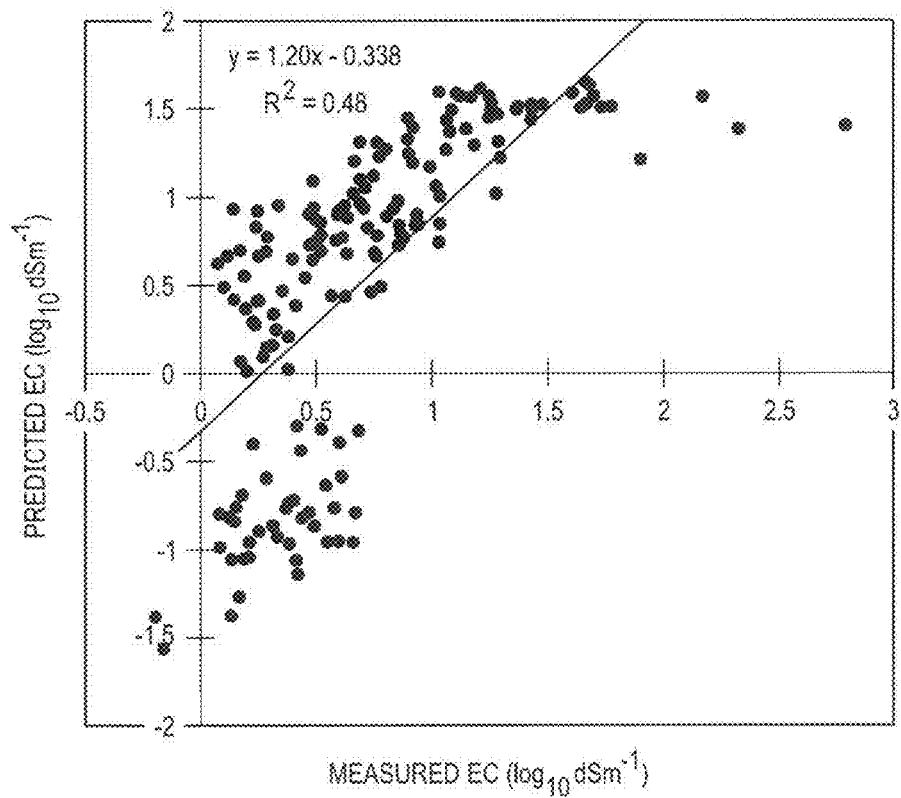

While comparing the relative training and testing accuracies of PXRF and remote sensing in predicting soil EC (1:5), both of these techniques underperformed relative to VisNIR DRS alone. Training models of PXRF showed poor match between lab-measured and predicted EC (1:5) values both at higher and lower ranges (FIG. 12A), which can be attributed to the variable sources contributing to salinity in both playas. The prediction worsened while using Landsat band reflectance alone (RPD=1.27) which can be ascribed to the spectral complexity arising from the variability of the soil surface conditions (crusts and gravels) and changes in bare soil surface conditions [1] (FIG. 12B).

Figure 12C:
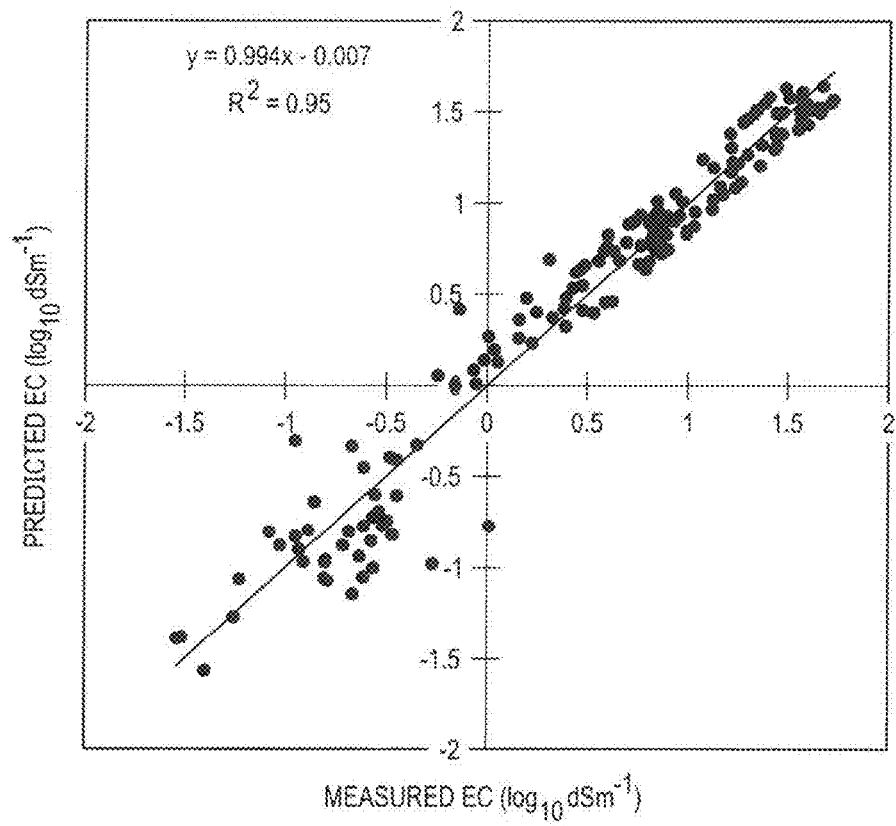
Figure 12D:
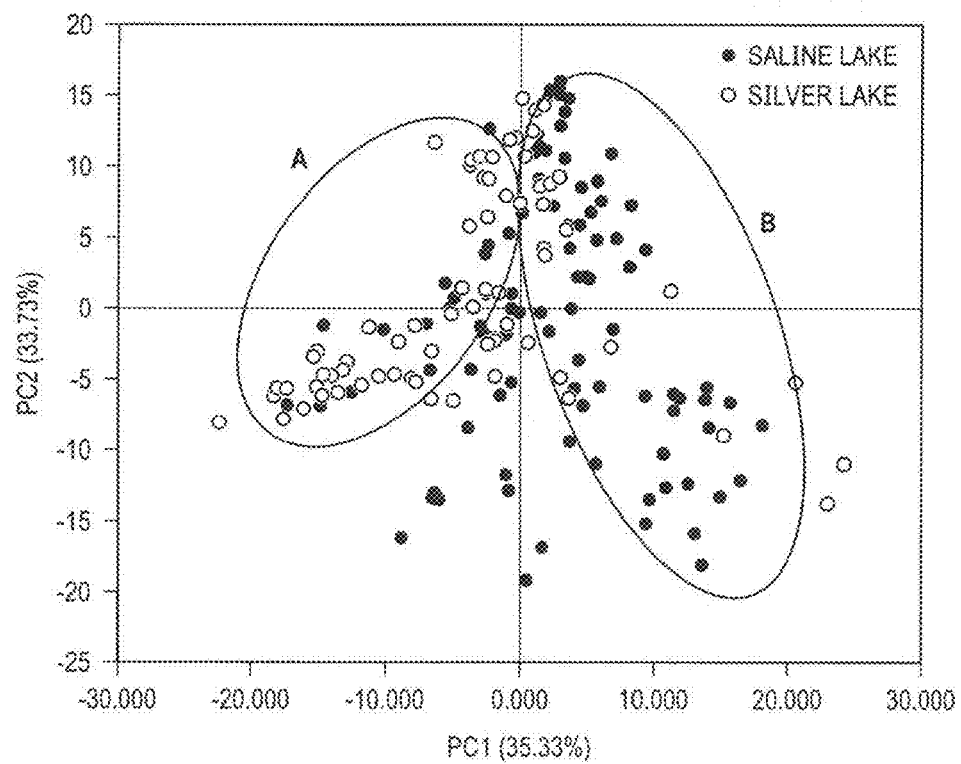

Strikingly, when combining all three approaches, the model generalizing capability was increased substantially and appeared better than any other model tested in this study (RPD=3.35) (FIG. 12C). Note that, only SG spectra was used since it exhibited the best generalizing potential irrespective of the multivariate model used. Moreover this spectral treatment was able to subtly separate samples from the two sites on PC1, further justifying the ability of VisNIR DRS to qualitatively discriminate sample spectra (FIG. 12D). This spectral separation could be explained by the heterogeneity which resulted partly from compositional variability of soil matrix and partly from variable salt accumulation.

Summarily, both PXRF and VisNIR DRS showed considerable promise in providing rapid EC (1:5) prediction is soils with reasonable accuracy, but the most pronounced one was VisNIR DRS. Adding PXRF data (especially S and Cl %) and RS reflectance values as predictors along with soil VisNIR spectra was beneficial and should be included to model soil EC (1:5). Acquisition of PXRF data is rapid, easy, and cost-effective. All three evaluated techniques share the advantage of determining soil EC (1:5) especially for unusual circumstances where non-destructive sampling is required. Additional research should be continued to include larger geographical ranges along with other soil properties, but the future of VisNIR DRS+PXRF+RS based soil EC (1:5) characterization appears promising. Although it is true that applications of VisNIR DRS and PXRF for in-situ prediction of soil EC (1:5) are perhaps inadequate in establishing soil variability and patterns of change, incorporating remotely sensed data can improve soil scientists' capability to map soil salinity across the landscape at high spatial resolution for enhanced soil management.

In this study, three alternative methods (VisNIR DRS, PXRF, and RS) for determining soil salinity were compared to traditional laboratory analysis (EC (1:5)). A total of 165 surface (0-5 cm) soil samples were collected from two playas in West Texas, USA. Salinity levels in these playas varied dramatically from 0.028 dS $m^{-1}$ in upland soils extending to the playa annulus and beyond to virtually pure salt crusts in the playa basins with EC (1:5) of up to 43.41 dS $m^{-1}$. Elemental concentrations (determined via PXRF) of S and Cl were found to be most strongly correlated to soil EC (1:5). With consideration of VisNIR DRS data, two multivariate algorithms were tested (PLS and SVR) and generally produced strong, significant relationships to soil EC (1:5). Comparing the relative accuracies of PXRF and RS in predicting soil EC (1:5), both produced suboptimal results relative to VisNIR DRS alone. Evaluated independently, the techniques were generally ranked as VisNIR DRS>PXRF>RS. Conversely, the synthesis of all three datasets produced the best predictive results; better than any one technique taken independently. The reported RPD values are acknowledged to be useful when the validation set is independent of the calibration set. However, with LOOCV they are still useful indicators for describing the potential of the technology. This study shows the potential of the present invention for use in future VisNIR+PXRF+RS based soil studies. As these types of data are quick, easy, and inexpensive to collect, two or three datasets can be combined for optimal soil salinity prediction. In doing so, researchers will obtain results of comparable quality to lab-derived data, yet with less time and effort than traditional laboratory salinity determinations. Additionally, the spectral and elemental datasets collected via scanning can be used for the prediction of multiple other soil parameters such as textural constituents (e.g., clay), soil pH, soil carbon content, and clay mineralogy.

Total Carbon and Total Nitrogen:

Given the success of the investigation described above, the application of synthesized spectroscopy models for TC and TN quantification seemed timely. Therefore, the objectives of this study were to: 1) evaluate soil TC and TN predictability using proximal soil sensing methods (VisNIR and PXRF) independently and, 2) investigate soil TC and TN predictability by combining VisNIR and PXRF approaches. In this study, soil TC and TN can be predicted from the direct elemental readings of PXRF and VisNIR spectra. Furthermore, predictive models from synthesized proximal soil sensing techniques will provide the best predictive ability; considerably better than each approach individually.

A total of 675 soil samples were collected from Seward County, Nebr., Kern County, Calif., and Lubbock County, Tex., USA during 2014. Specifically, in each state, 75 sampling points were randomly selected within a single agricultural field and collected at three depths (0-15, 15-30, and 30-45 cm). The fields in Nebraska, California, and Texas supported corn, wheat, and cotton, respectively. At each site, soils were sampled with a sharpshooter or auger, placed in sealed plastic bags, and shipped to the Texas Tech University Pedology Laboratory for analysis. Generally, the Nebraska soils were from the Hastings (Fine, smectitic, mesic Udic Argiustolls), Fillmore (Fine, smectitic, mesic Vertic Argialbolls), and Butler (Fine, smectitic, mesic Vertic Argiaquolls) soil series in major land resource area (MLRA) 75-Central Loess Plains [37]. In California, soils were from the Wasco (Coarseloamy, mixed, superactive, nonacid, thermic Typic Torriorthents) series in MLRA 17-Sacramento and San Joaquin Valleys [37]. In Texas, soils were from the Amarillo (Fine-loamy, mixed, superactive, thermic Aridic Paleustalfs), Acuff (Fine-loamy, mixed, superactive, thermic Aridic Paleustolls), and Estacado (Fine-loamy, mixed, superactive, thermic Aridic Paleustolls) soil series in MLRA 77C Southern High Plains, Southern Part [37]. In selecting the soil sampling sites, soils were chosen from disparate locations such that considerable variation would be represented in soil physicochemical properties. Importantly, samples at each depth at each site were composites of two subsamples, which were not necessarily vertically associated at the same collection point. Furthermore, all fields sampled were regularly plowed by farm machinery, causing wholesale mixing of the upper 45 cm of soil.

Upon arrival in the laboratory, all samples were air dried, and ground to pass a 2-mm sieve prior to general laboratory analysis. Soil samples for high temperature combustion analysis were further sieved to pass a 0.25 mm sieve prior to analysis. TC and TN values were determined for soil samples via Dumas method combustion using a Truspec® CHN analyzer (LECO Corp., St. Joseph, Mich., USA) per Soil Survey Staff [106] and Fultz et al. [69].

The spectra of the 675 soil samples were obtained using a PSR-3500® portable VisNIR spectroradiometer (Spectral Evolution, Lawrence, Mass., USA) with a spectral range of 350 to 2500 nm. The spectroradiometer had a 2-nm sampling interval and a spectral resolution of 3.5, 10, and 7-nm from 350 to 1000 nm, 1500 nm and 2100 nm, respectively. Scanning was facilitated with a contact probe featuring a 5 W built-in light source. Full contact with the sample was ensured to avoid outside interference. Each sample was scanned four times with a 90° rotation between scans to obtain an average spectral curve. Each individual scan was an average of 10 internal scans over a time of 1.5 s. The detector was white referenced (after four samples) using a 12.7 cm Å~12.7 cm NIST traceable radiance calibration panel, ensuring that fluctuating downwelling irradiance could not saturate the detector.

Raw reflectance spectra were processed via a statistical analysis software package, R version 2.11.0 [97] using custom "R" routines [11, 12]. These routines involved (i) a parabolic splice to correct for "gaps" between detectors, (ii) averaging replicate spectra, (iii) fitting a weighted (inverse measurement variance) smoothing spline to each spectra with direct extraction of smoothed reflectance at 10 nm intervals. This study used one spectral pretreatment to prepare the smoothed soil spectra for analysis, and two multivariate algorithms to develop the TC and TN predictive models. Spectral pretreatments helped in reducing the influence of the side information contained in the spectra. The pretreatment transformation applied was Savitzky-Golay (SG) first derivative using a first order polynomial across a ten band window. The transformation was implemented in the Unscrambler®X 10.3 software (CAMO Software Inc., Woodbridge, N.J.).

All samples were also scanned using a DP-6000 Delta Premium PXRF (Olympus, Waltham, Mass., USA). The instrument features a Rh x-ray tube operated at 15-40 keV with quantification via ultra-high resolution (b165 eV) silicon drift detector. Prior to soils analysis, the instrument was calibrated using a 316 alloy clip, containing 16.130% Cr, 1.780% Mn, 68.760% Fe, 10.420% Ni, 0.200% Cu, and 2.100% Mo, tightly fitted over the aperture. The instrument was operated in "Soil Mode" capable of detecting the following suite of elements: Sr, Zr, Mo, Ag, Cd, Sn, Sb, Ti, Ba, Cr, Mn, Fe, Co, Ni, Cu, Zn, Hg, As, Se, Pb, Rb, P, S, Cl, K, Ca, and V. Soil Mode consists of three beams which operate sequentially. Each beam was set to scan for 30 s such that one whole scan was completed in 90 s. As the PXRF analysis window is small (approximately 2 cm$^2$), it is important that the average composition of the sample is well represented within this area. Soil samples were carefully mixed to ensure sample homogeneity before scanning. Also, the aperture of the instrument was kept clean by air blowing to prevent soil or dust from contaminating the aperture window after each scan. Elemental data was stored in the on-board computer, and then downloaded into MS Excel for analysis.

The two multivariate methods tested included random forest (RF) regression and penalized spline regression (PSR). Both VisNIR-SG spectra and PXRF elements were combined in a single table and the whole dataset was randomly divided twice into i) a ~70% training set (n=472) for calibration and a ~30% independent test set (n=203) and ii) for a more honest evaluation of the prediction performance, a ~70% training set (n=472) for calibration and a ~30% independent test set (n=203) for validation keeping the three depths of a given profile together. Note that, no pre- or post-processing was applied on PXRF data.

Classical least squares modeling approaches usually fail on high dimensional multivariate calibration problems because the size of the regressors is larger than the sample size. Unlike most other approaches, a PSR model makes use of the ordered structure among the regressors [68]. The objective function on which the penalized spline minimizes is a tradeoff between the goodness-of-fit on the data through sum squared error (SSE) and the penalty function on the smoothness of the estimated regression coefficients (i.e. constraining the difference between the neighboring regression coefficients) [83]. Because of the additional smoothness penalty, penalized spline is well-suited for ill-posed problems (the dimensionality is much larger than the sample size) such as signal regression problems. Since PSR is a straightforward extension of the linear regression model, it inherits all the beneficial properties from linear regression, such as the confidence interval of estimated regression coefficients. The computation of the PSR model, including cross-validation, is relatively less penalizing. For leave-one-out cross-validation (LOOCV), a penalized spline model can directly output the validation error without recomputation of the model omitting each sample. In this study, the cubic B-spline was used via R version 2.14.1 [97] as the base function with 100 equally spaced knots. The order of the penalty was set to the default value of three. The optimal value for the penalty-tuning parameter was selected by minimizing the LOOCV error on the training set.

Random forest [56] is an ensemble learning method that combines hundreds of individual trees. To build each tree, first a bootstrap sample is drawn from the training samples; then a tree is built using the bootstrap sample of the data, and at each node split the candidate set of the regressor is a random subset (the size of the subset is denoted as mtry) of all the regressors. The final prediction of a new observation is the average of the predicted values (for the new observation) from all the trees in the forest. Studies have shown that the prediction accuracy of the random forest ensemble is usually better than the one from an individual tree [56]. In this study, the 'random forest' package was used in R to build the random forest model. The number of trees in random forest was set to the default value of 500. The coefficient of determination (R2), RMSE, residual prediction deviation (RPD) [49], and bias were used as rubrics for judging model generalizing capability. Since RPD is the ratio of standard deviation and RMSE, model predictability is enhanced when the validation set standard deviation (SD) is comparatively larger than the estimation error (RMSE). Chang et al. [13] categorized the accuracy and stability of their spectroscopy models based on the RPD values of the validation set. RPDs N 2.0 were considered stable and accurate predictive models; RPD values between 1.4 and 2.0 indicated fair models that could be improved by more accurate predictive techniques; RPD values b1.4 indicated poor predictive capacity.

In this study, five modeling approaches were employed as follows:

1. At first, both TC and TN were predicted using simply concatenating PXRF elements with VisNIR spectra via PSR and RF.
2. Next, both TC and TN were predicted using VisNIR spectra alone via PSR and RF.
3. A RF model was used to predict TC and TN using only PXRF elements.
4. As a conservative estimate of model performance, entire profiles were selected for calibration and validation to maintain independence between calibration and validation data [58]. Then, RF was applied to PXRF data only, PSR and RF were applied to VisNIR data only, and PSR and RF were applied to fused PXRF+VisNIR datasets. Scans for individual soil profiles were not split between calibration and validation datasets.
5. Finally, whole-field holdout validation was done for both TC and TN to determine how field to field heterogeneity affected prediction accuracies [58]. Whole-field holdouts were achieved by calibrating a model using RF with two of the three fields. The third field was held out as the validation sample. A total of 12 models were created to represent all three fields as a validation set using a) PXRF elements+VisNIR spectra, and b) PXRF elements only.

Importantly, not all elements were quantified with discreet values via PXRF. Thus, only 10 elements (K, Ca, Ti, V, Mn, Fe, Zn, Rb, Sr, Zr, and Pb) were viable for regression, with discreet values across all soil samples scanned. Soil samples varied widely in their estimated properties, likely a result of differences in land use, sampling depth, vegetation cover, and geologic origin. Statistical moments related with soil TN, TC, and PXRF sensed elements are explained as follows: compared to other properties, PXRF-sensed K (~3-fold), Rb (~4-fold), Zr (~4-fold), Fe (5-fold), Ti (5-fold), V (6-fold), Zn (7-fold) and Sr (9-fold) exhibited relatively lower ranges of variation (Table 4). The ranges of variation of other properties were markedly larger [15-(Mn) to 91-fold (TC)]. PXRF-sensed total Ca produced the highest range of variation (1729-fold). Both TN and TC were non-normally distributed (Shapiro-Wilk p-values b 0.0001) from 0.006 to 0.33% and 0.06 to 6.16%, respectively (FIGS. 13A and 13B. Most of the variables were significantly correlated between themselves with some exceptions (Table 5). Notably, TC was significantly correlated with TN ($\rho$=0.87). The C:N ratios for California (max 16.1, min 4.0, 8.5), Texas (max 97.9, min 5.9, 10.5), and Nebraska (max 15.2, min 4.8, 9.4) were all similar. Neither N nor C is measured by PXRF; both elements are too light. But previous research [104] has shown that other elements can and do have significant associations with light elements. Thus, while the PXRF does not directly measure C or N, the inclusion of other elements quantified by PXRF strengthens the predictive algorithms as auxiliary input data.

Figures 13A, 13B, 13C:
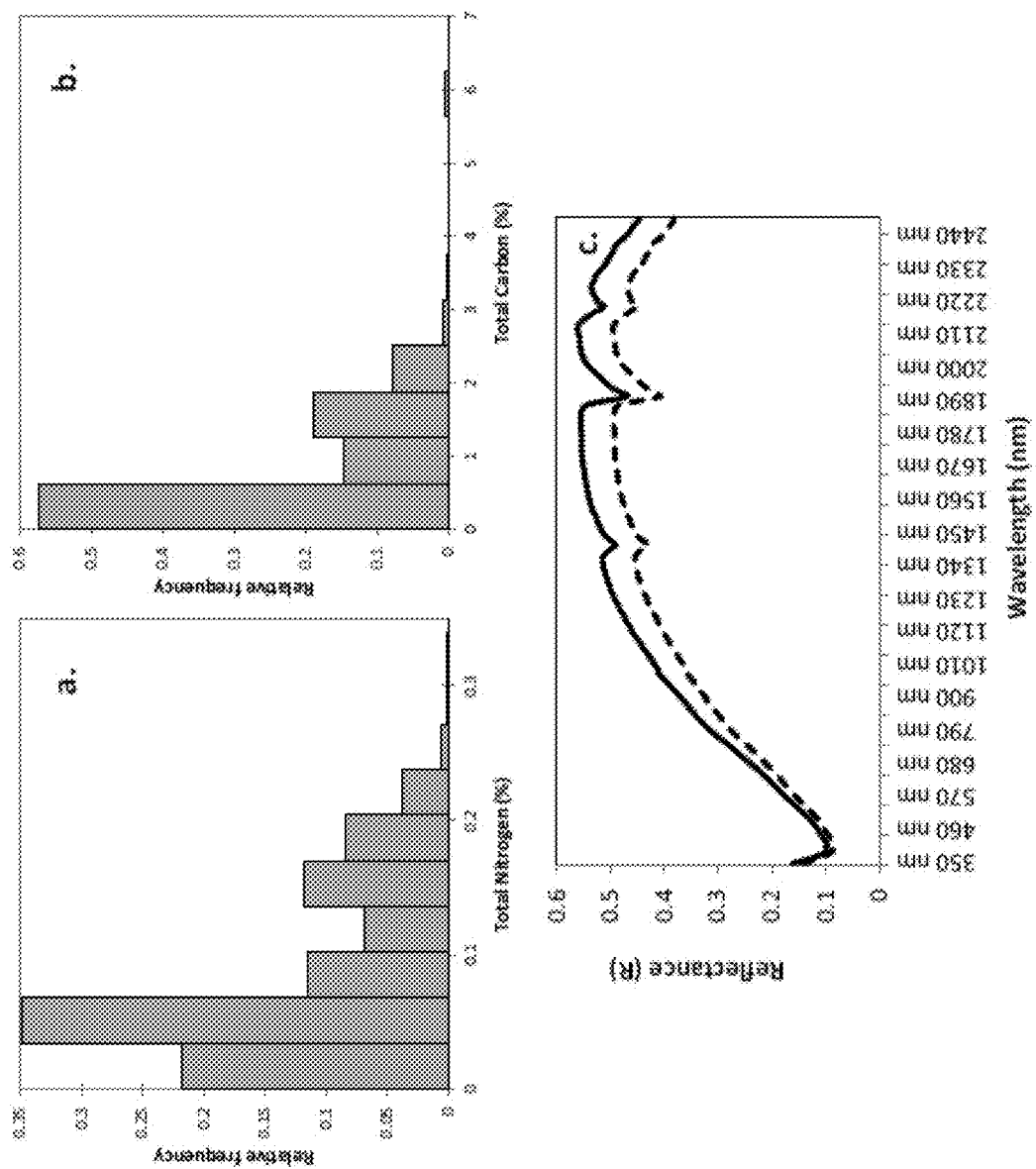
FIGS. 13A-13C are plots showing histograms of a) soil total N, b) total C, and c) average reflectance spectra of two randomly selected soil samples. Both soils exhibited two distinct absorption peaks around 1900 (water absorption bands) and 2200 nm (metal-hydroxyl stretching)

Average reflectance spectra of two randomly selected soil samples are shown in FIG. 13C. In general, reflectance spectra for both soils were similar regarding high optical density [log (1/R)] in the visible light region (350-750 nm) and two distinct absorption peaks around 1900 (water absorption bands) and 2200 nm (metal-hydroxyl stretching), as reported in the literature [64].

Figures 14A, 14B, 14C, 14D:
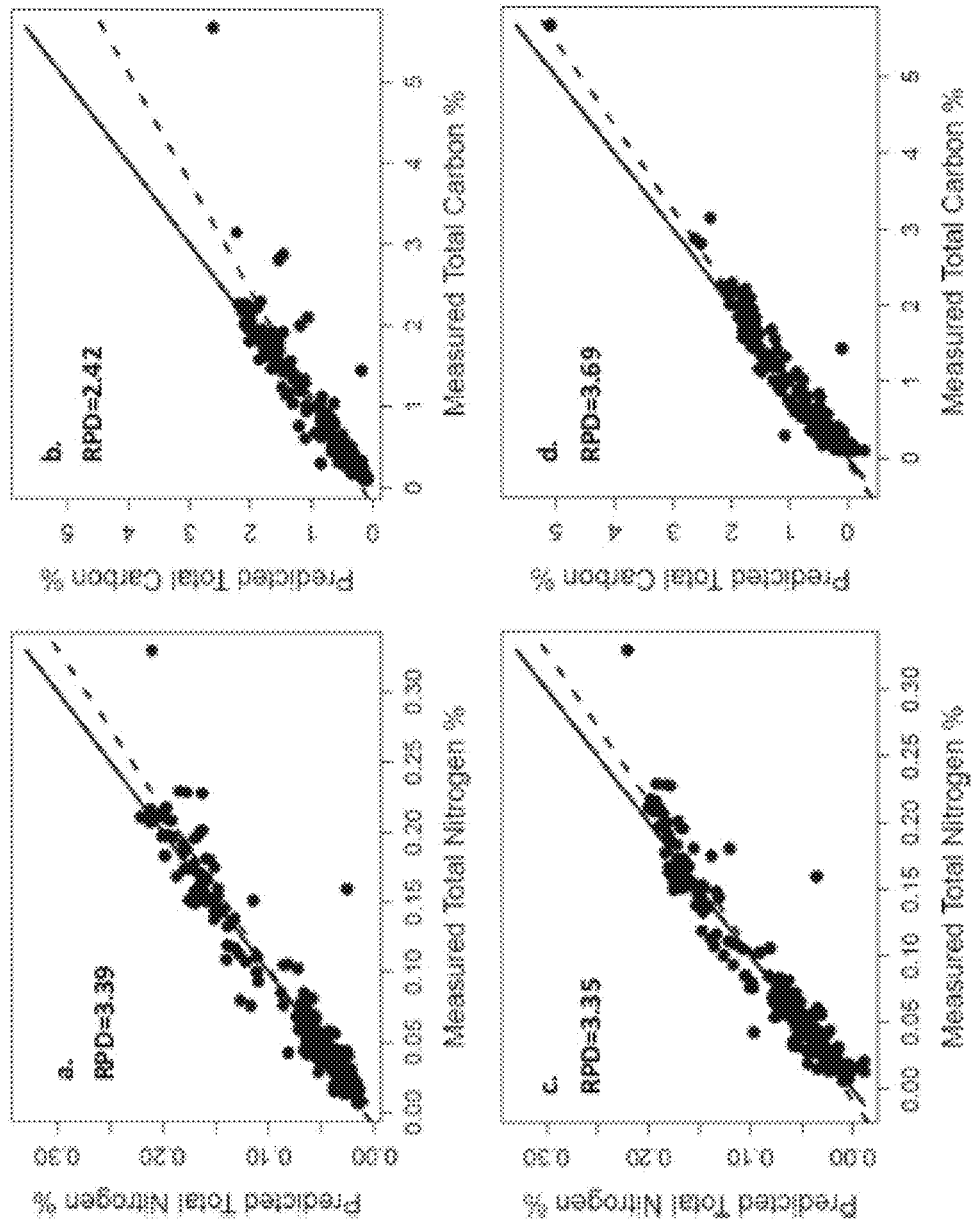
FIGS. 14A-14D are plots showing a) random forest model for total N, b) random forest model for total C, c) penalized spline model for total N, and d) penalized spline model for total C using randomly selected VisNIR spectra and PXRF elements.
Figure 15:
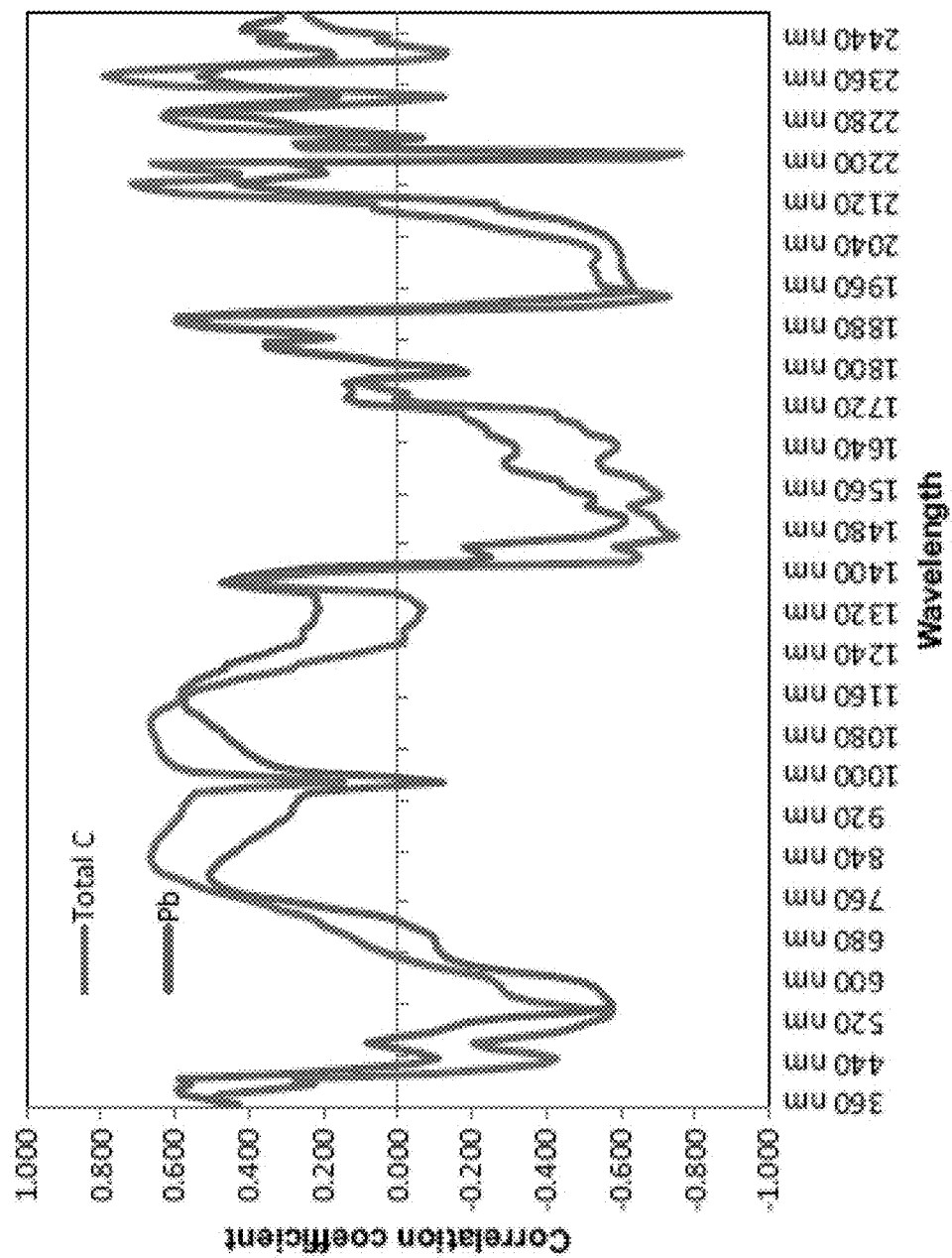
FIG. 15 are Correlation patterns between reflectance of VisNIR reflectance spectra and Pb contents of soil and total C.
Figures 16A, 16B, 16C, 16D:
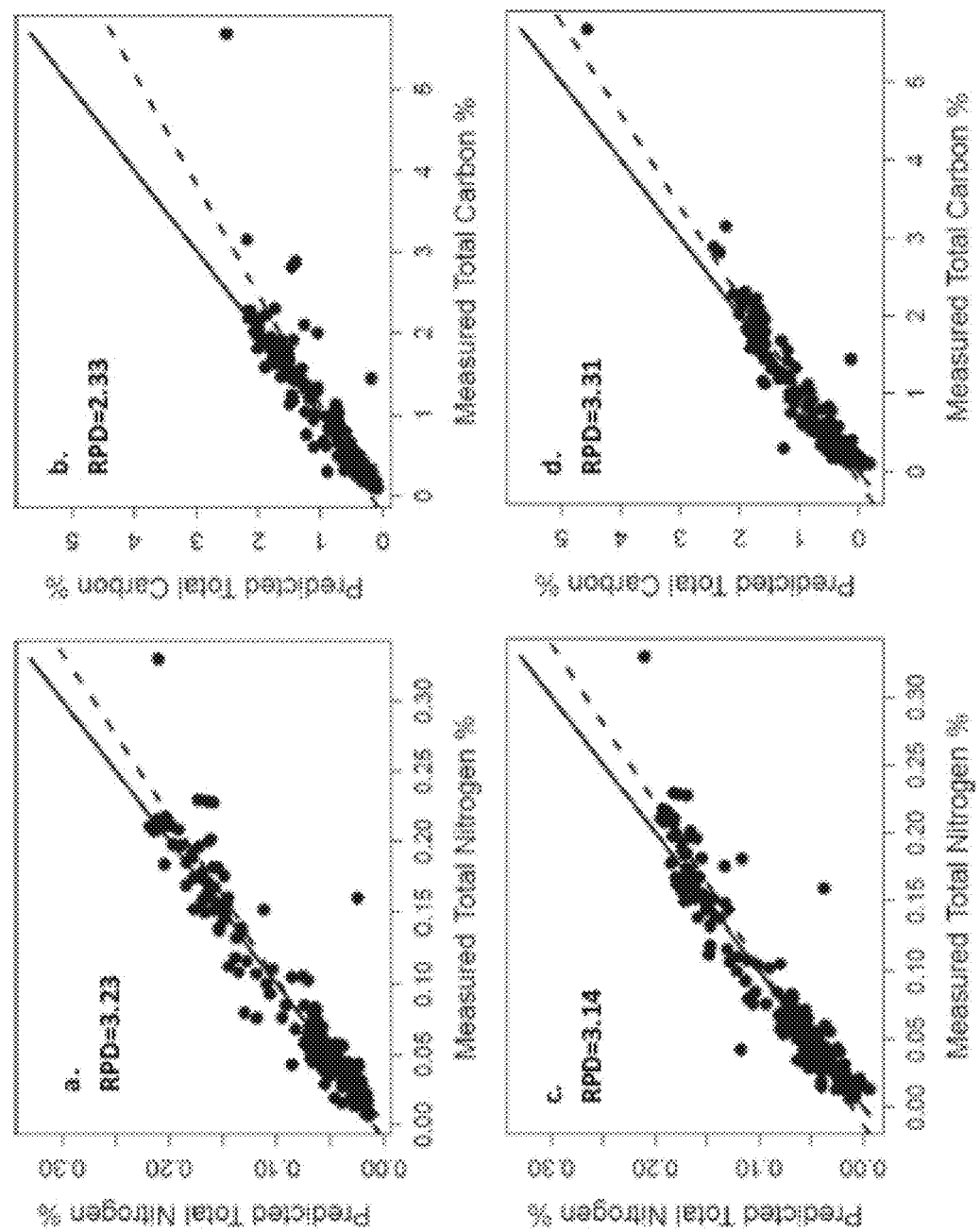
FIGS. 16A-16D are plots showing a) random forest model for total N, b) random forest model for total C, c) penalized splinemodel for total N, and d) penalized spline model for total C using randomly selected VisNIR spectra only.
Figures 17A, 17B, 17C, 17D:
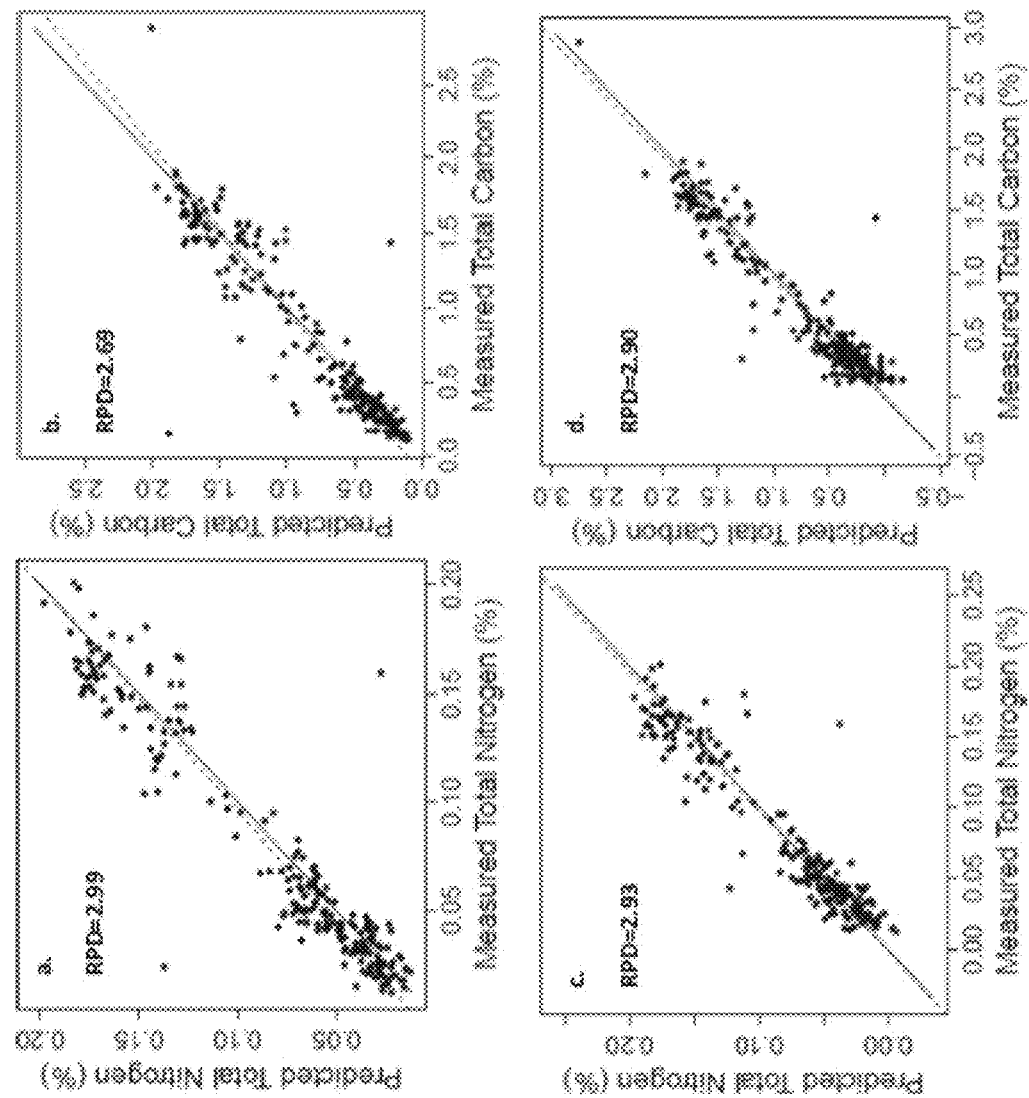
FIGS. 17A-17D are plots showing a) random forest model for total N, b) random forest model for total C, c) penalized spline model for total N, and d) penalized spline model for total C using whole soil profile VisNIR spectra and PXRF elements.
Figures 18A, 18B, 18C, 18D:
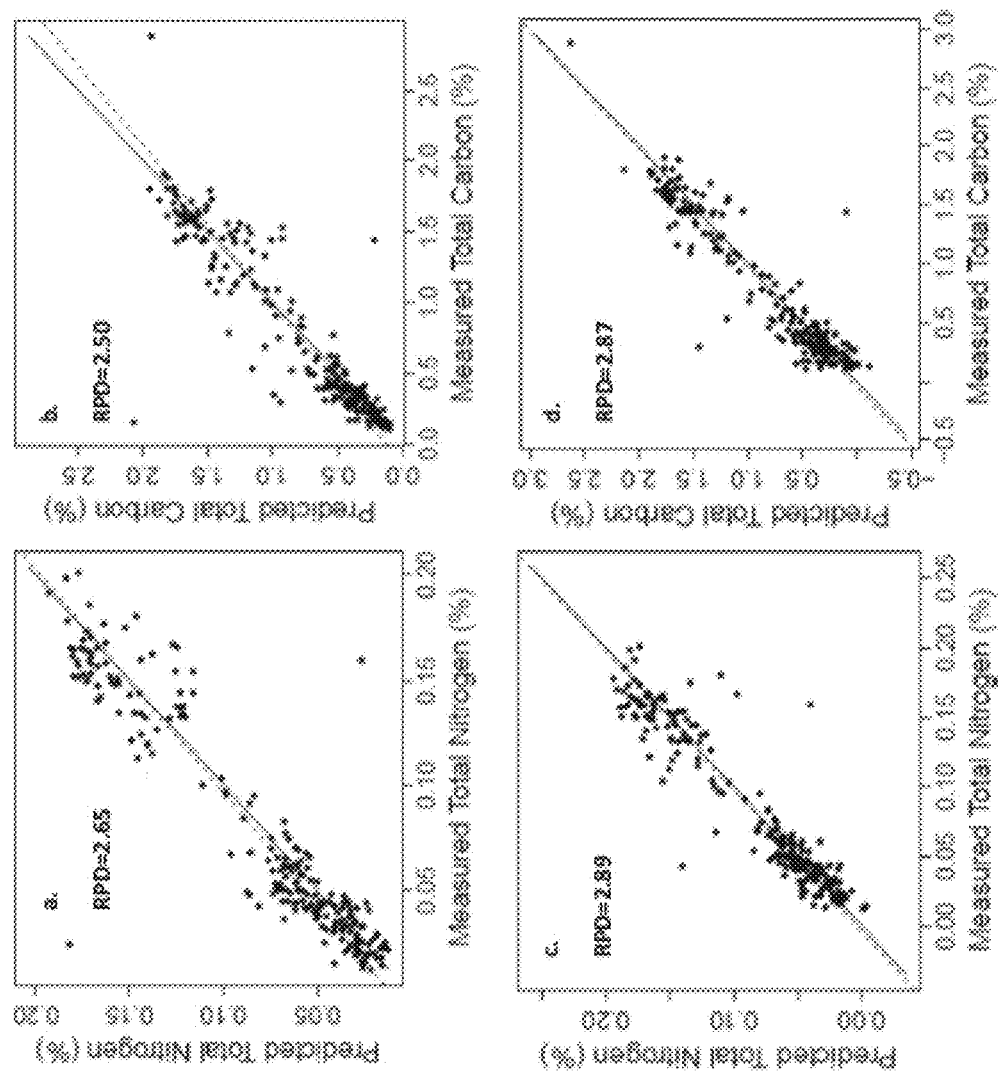
FIGS. 18A-18D are plots showing a) random forest model for total N, b) random forest model for total C, c) penalized spline model for total N, and d) penalized spline model for total C using whole soil profile VisNIR spectra only.

Initially, among the two multivariate algorithms tested (RF and PSR) by concatenating both VisNIR spectral data and PXRF elements irrespective of keeping the same profile intact, TC was estimated with greater accuracy by PSR while TN was estimated slightly better by RF (Table 6). Although both RF and PSR produced an identical R2 (0.91) for TN, the former exhibited a slightly higher RPD value of 3.39. Conversely, the PSR model for TC increased both validation R2 (0.93) and RPD (3.69) relative to its RF counterpart. In general, both RF and PSR models for TN exhibited slight underestimation at higher values (FIGS. 14A-14D). Some of these underestimations could be due to the relative scarcity of observations at the higher ends of the property scales, as previously outlined by Brown et al. [59]. On the contrary, while measured vs. PSR predicted TC closely approximated the 1:1 line with slight underestimation at higher values (FIG. 14D), exhibiting a greater deviation from the 1:1 line the prediction worsened further for the RF model (FIG. 14B). Given that the consistency of a NIR spectroscopic model is normally restricted to the range of parameter values, the wide ranges of soil TC (0.067-6.16%) and TN (0.006-0.33%) perhaps contributed to the overall satisfactory results (Table 4). Since regression coefficients of TN were rather similar to those of TC, it can be concluded that VisNIR detected a combination of soil constituents containing organic functional groups, which contain organic forms of N. Although intense bands in the VisNIR spectra are not directly associated with the presence of metals or other constituents, it is already established that metals can interact with the main spectrally active components of soil like soil C [107]. To further validate this hypothesis, we randomly selected PXRF sensed Pb which exhibited both positive and negative correlations with VisNIR reflectance spectra of soil (FIG. 15). Further, Pb showed strong negative correlations at ~520 nm, ~1480 nm, ~1890 nm, and ~2200 nm; where there was also a strong negative relationship with the TC content of the soils (FIG. 15). Thus, the above correlations gave an indication of the good relationship of the Pb (and perhaps for other PXRF elements) with TC. This explanation was supported by the significant correlations of the PXRF sensed elements (except Mn) with TC which represents soil organic matter (Table 5). Association with organic matter may be a main binding form of PXRF sensed elements in soils. These findings further rationalized the use of PXRF elements in predicting TC and TN of soil samples. These results also provide support for the synergistic use of diffuse reflectance spectra and PXRF elements in predicting TC contents of soil samples.

When both TC and TN were modeled with PSR and RF using only VisNIR data irrespective of keeping the same profile intact, a similar trend was observed. Indeed, while both PSR and RF models for TN exhibited almost the same generalization capacity, the PSR-TC model again showed improved predictability ($R^2$=0.90, RPD=3.31) as compared to the RF-TC ($R^2$=0.81, RPD=2.33) model (Table 6). Following the same trends of VisNIR+PXRF models for TN, both PSR-TN and RFTN models using VisNIR spectra showed close approximation to the 1:1 line with subtle underestimation at higher values (FIGS. 16A-16D). Furthermore, the prediction for TC deviated more from the 1:1 line in the RF model (FIG. 16B) than in the PSR model (FIG. 16D), corroborating the lesser predictability of the former. One important observation was that concatenation of Vis-NIR and PXRF data produced better predictability than using VisNIR spectra alone for modeling both TC and TN.

Additionally, to test the hypothesis that predictive models from synthesized proximal soil sensing techniques provide the best predictive ability irrespective of keeping the same profile intact, noticeably better than each approach individually, TC and TN were modeled with PXRF elements only. While predicting with PXRF elements via RF algorithm, a substantial reduction in model generalization was obtained in the case of TC ($R2=0.77$, RPD=2.11) (Table 7). Moreover, while considering RF-TN with PXRF elements only, a steady decrease of RPD values was obtained from its VisNIR+PXRF (RPD=3.39) and VisNIR only (RPD=3.23) counterparts.

While keeping the same profile intact for calibration and validation, similar trends were observed, although with slightly lowered model accuracy than those obtained when samples from the same profile were mixed between calibration and validation sets. Models obtained by combining both VisNIR and PXRF outperformed their VisNIR only and PXRF only counterparts (Table 7). While TC was estimated with noticeably greater accuracy by PSR (RPD=2.90) than RF, TN was estimated slightly better by RF (RPD=2.99) than its PSR counterpart (RPD=2.93). In general, while RF models for TC exhibited slight underestimation at higher values, PSR closely approximated the 1:1 line (FIGS. 17A-17D and 18A-18D). There were only a few predictions falling beyond ±10% of the reference data. Summarily, the results reported a remarkable accuracy suggesting that combination of VisNIR and PXRF could be convenient for estimating several soil properties with advanced empirical calibrations.

Figures 19A, 19B:
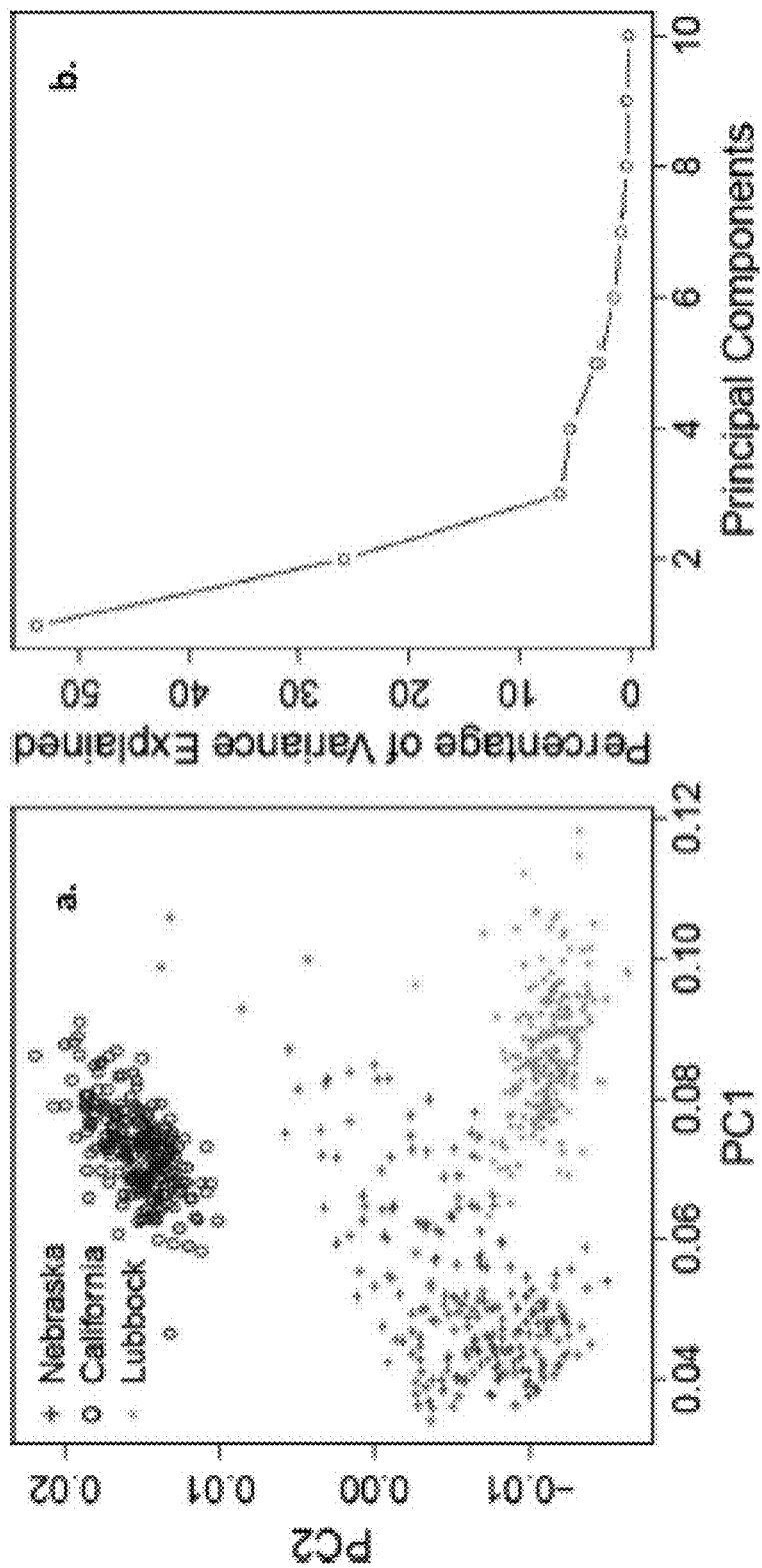
FIGS. 19A-19B are plots showing a) principal component plot for PC1 vs. PC2 of the first-derivative of VisNIR reflectance spectra. The red crosses, green dots, and blue circles represent soils from Nebraska, Lubbock, and California, respectively. Plot b) represents the "Screeplot" of the first ten principal components of the first derivative spectra.

Nevertheless, holding out whole fields reduced prediction accuracies in all cases where the soils of the field held out were not represented by another field, creating extrapolation (Table 8). Addition of PXRF data did not produce any visible improvement. Validation with an individual field exhibited significant increases in RMSEs and a reduction in RPDs relative to the 30% random validation set. As expected, when principal component analysis was implemented on the VisNIR spectrum only, it clearly demonstrated different spectral behaviors of the three locations (FIGS. 19A-19B). For example, the soil textures of Nebraska (silty clay loam, silty clay), California (sandy loam), and Texas (sandy loam, sandy clay loam) were largely different (FIGS. 19A-19B).

Summarily, both PXRF and VisNIR DRS showed considerable promise in providing rapid TC and TN prediction in soils with reasonable accuracy, but the most pronounced one was VisNIR DRS. Adding PXRF elemental data as predictors along with soil VisNIR spectra was beneficial and should be included to model soil TC and TN. One possible reason for the improved estimation of TC and TN by the PXRF+DRS approach can be the covariation of non-chromophores or spectrally inactive components (PXRF elements except Fe and Mn) with relevant chromophores or spectrally active components (especially organic carbon).

The better performance of PSR can be attributed to its stability and flexibility; more so than other parametric approaches like partial least squares regression and principal component regression since the shape of the functional relationship between covariates and the dependent variable (soil TC and TN, in this study) was managed by the data [68, 83]. Nonparametric PSR which has become a very powerful and applicable smoothing technique over the last 10-15 years can be considered as a simplification of smoothing splines with a more flexible choice of bases and penalties [77]. Given that, P-spline smoothing tied with ridge regression, mixed models, and Bayesian statistics, allows more sound handling of signal regression problems such as Vis-NIR DRS. The improvement of model generalization capability by implementing PSR followed the same trend reported elsewhere for other soil and compost properties [62, 63]. However, in this study PSR could not be applied on only PXRF elements since PSR is only applicable for signal regression. In other words, since PSR assumes smoothness of the coefficient for each channel, the X should be a signal (reflectance).

Acquisition of PXRF data is rapid, easy, and cost-effective. Both evaluated techniques share the advantage of determining TC and TN especially for unusual circumstances where non-destructive sampling is required. Evaluated independently, the techniques were generally ranked as VisNIR DRS>PXRF. Conversely, the synthesis of both datasets produced the best predictive results; better than any one technique taken independently. These results strongly support the previously described study where synthesizing PXRF data with VisNIR spectra boosted the prediction of soil EC [51].

In this study, one obvious question was: is it possible to directly analyze soil TC and TN in fresh samples by VisNIR DRS+PXRF? This question was critical as we attempted to develop models which could ultimately lead to in situ measurements in future. Given that VisNIR DRS can sense the changes in the matrix material scanned, particularly moisture (as it relates to O\H bonding and color) [55, 126], bringing the soil samples to standard water content prior to scanning is critical for obtaining consistent results. In the present study, soil samples were air-dried. Despite that, it cannot be excluded that even in low soil moisture conditions, there was still remaining water adsorbed on the surface areas of clay minerals (e.g., hygroscopic water) and organic matter in equilibrium with atmospheric water vapor. Interestingly, even pre-treatment methods like quick-freezing and freeze-drying were unable to remove the water completely from the layer minerals of soil [111]. However, these minor variations perhaps did not cause much difference in the NIR spectra, as previously identified by Minasny et al. [88]. Maintaining homogeneous water content in the field during in situ scanning is not easy. Establishing the best sample pretreatment (field-moist or air-dried) was beyond the scope of this study and requires further investigations. Hence, the question of "how best to develop calibrations when moisture is present" is one of the big issues that remains to be properly answered about calibrations for soil TC and TN with VisNIR DRS and PXRF.

In conclusion, 675 soil samples representing disparate physicochemical conditions from three different states in the USA were evaluated for TC and TN using synthesized PXRF and VisNIR spectroscopy datasets, and traditional laboratory analysis (Dumas method high temperature combustion). Specifically, random forest (RF) regression and penalized spline regression (PSR) were used as multivariate tools for relating the two datasets in terms of R2, RMSE, and RPD. Results were compelling, with validation sub-datasets producing optimized total carbon predictions via PSR (RPD=3.69; $R^2=0.93$) and total nitrogen predictions via RF (RPD=3.39; $R^2=0.91$). Even while keeping the same profile intact for calibration and validation, independent validation data for synthesized (PXRF+VisNIR) models produced quality predictive statistics for soil TC (RPD=2.90; $R^2$=0.88 via PSR) and TN (RPD=2.99; $R^2$=0.89 via RF) and outperformed other models tested. Predictions were also made with both PXRF and VisNIR data independently; both were less robust than the synthesized dataset approach utilizing both in tandem for predictions. The general predictive ability can be summarized as follows: PXRF+VisNIR N VisNIR N PXRF. The synthesized dataset approach is a revolutionary step forward in soil chemical analysis as proximally captured data can effectively predict both TC and TN contents in soils quickly, non-destructively, and with little need for traditional laboratory analysis. Furthermore, as has been previously described, the data from such proximal sensing (both spectral and elemental) can be used for the simultaneous prediction of any number of different soil properties, by simply applying the appropriate modeling equation. Such an approach has widespread applicability in both agronomic (e.g., plant essential element) and environmental (e.g., carbon stock assessment, carbon sequestration) applications.

Identification of Petroleum Contaminated Soils:

While the value, utility, and application of these two techniques (VisNIR DRS and PXRF) have been proven repeatedly in independent studies, these technologies have not yet been combined into a singular approach for rapid, on-site environmental quality assessment. As described above, combining the approaches described herein will allow for comprehensive assessment of both organic and inorganic soil contaminants and allow for instant quantitative results on-site. Because these approaches require no consumables and provide results within seconds, they offer tremendous advantages over traditional sampling, allowing for pervasive, high density spatial and temporal assessment of soil contaminants. Previous studies have elucidated the relationship of various elements with crude oil (hydrocarbons) [146, 144]. Furthermore, the traditional analytical test procedures used to evaluate soil contamination by petroleum products are petroleum hydrocarbons and heavy metals quantification [157, 154, 151, 128]. The inclusion of metal/elemental data into VisNIR DRS hydrocarbon predictive models will enhance TPH predictive ability.

Thus, the objective of this study was to examine whether predictive models from synthesized proximal soil sensing techniques can provide better predictive ability than VisNIR DRS alone. This study is the first attempt to utilize VisNIR-DRS spectra in combination with PXRF elemental data for the determination of petroleum hydrocarbons in contaminated soils. The proposed methodology could be applied in real time to provide rapid soil petroleum contamination assessment.

Figures 20A, 20B:
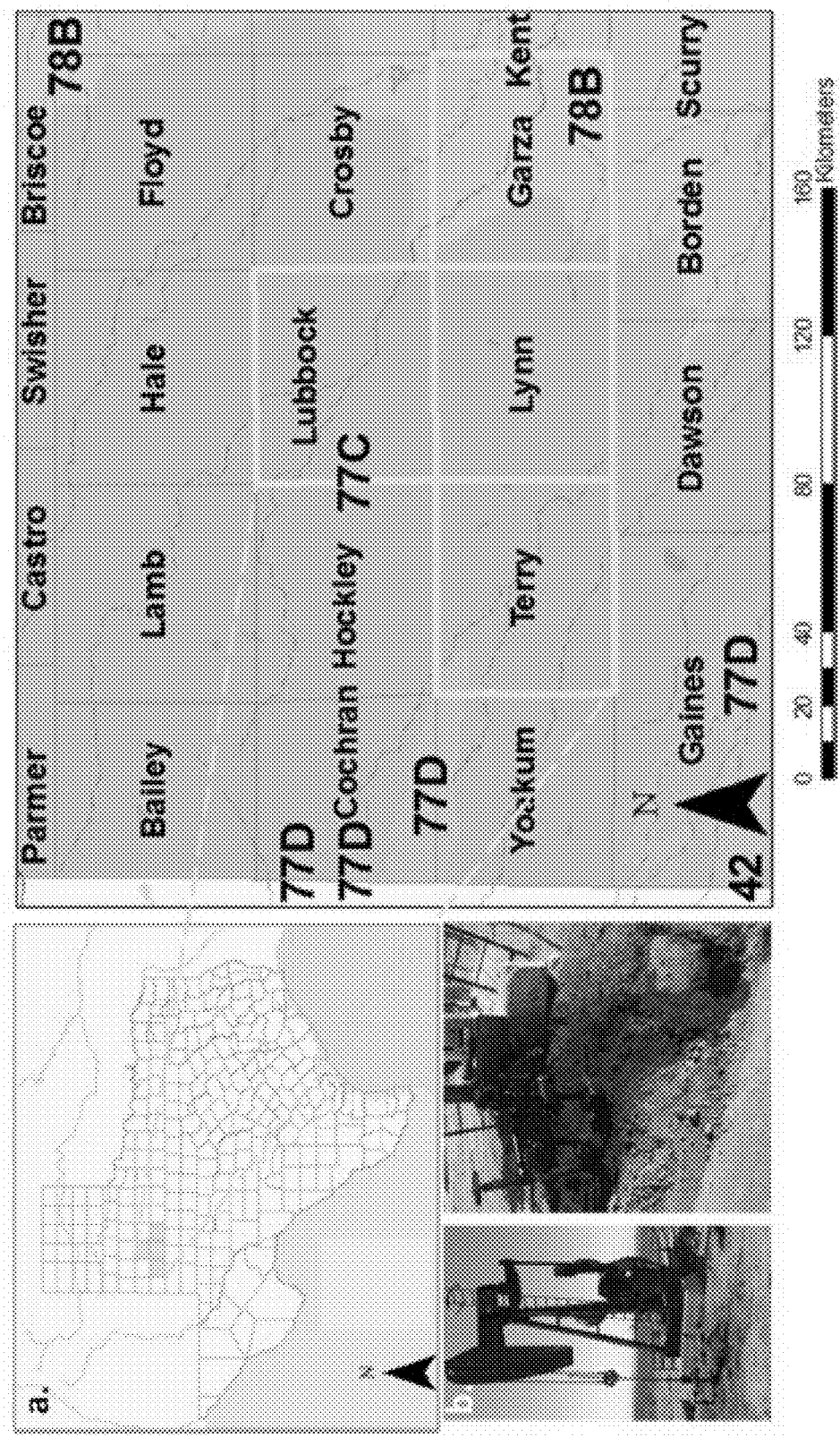
FIGS. 20A-20B depict a) map showing the counties in West Texas, USA where the soil samples were collected and, b) pump jack with contaminated soil in the foreground and active cotton production in the background; pump jack with pervasive contamination at a rangeland site.

Soil samples were collected at active oil production sites in Lubbock, Garza, Lynn, and Terry Counties, Tex., USA in January, 2014. For each site, efforts were made to collect surface (0-2 cm) soil samples from sites clearly impacted by hydrocarbon contamination (e.g., odor, visual evidence of oil) as well as from adjacent soils nearby with no evidence of contamination (control samples) (FIG. 20A-20B). Some of the sampling sites were in active crop fields, while other sites were in native rangeland for beef cattle production. In total, 108 samples were collected from the soils presented in Table 8. Sampling sites were within major land resource areas (MLRAs) 77C (Southern High Plains—Southern Part) and 78B (Central Rolling Red Plains—Western Part) [36]. These areas are characterized by a semi-arid climate with average annual precipitation totaling 405-560 mm and average annual temperatures of 13 to 17° C. Prevailing winds are from the south with an average freeze free period of 225 days y-1. Geologically, the area is covered largely with aeolian deposits of the Blackwater Draw formation (Pleistocene age). In Garza County, Permian shale, sandstone, gypsum and dolomite in the Whitehorse, and Blain Formations are common. Aeolian deposits are on top of a large escarpment (caprock), extend westward some 100 km, and generally are used for irrigated agricultural production of cotton (*Gossypium hirsutum* L.). Rangeland to the east of the escarpment is commonly comprised of mesquite (*Prosopis glandulosa* Torr.), mixed grasses, and cacti.

At each sampling site, samples were placed in glass jars and sealed for transport back to the Texas Tech University Pedology Laboratory for spectral analysis. Upon arrival, samples were refrigerated at 5° C. At each site, a brief site description was made and mapped soil recorded with the use of the SoilWeb application for iPhone; an application which uses geolocation to reference current position with soil survey geographic data for a given location.

The spectra of the soil samples were obtained using a PSR-3500® portable VisNIR spectroradiometer (Spectral Evolutions, Lawrence, Mass., USA) with a spectral range of 350 to 2500 nm. The spectroradiometer had a 2-nm sampling interval and a spectral resolution of 3.5, 10, and 7-nm from 350 to 1000 nm, 1500 nm and 2100 nm, respectively. Scanning was facilitated with a contact probe featuring a 5 W built-in light source. VisNIR experimental parameters and scanning procedures followed as part of this study are given by Aldabaa et al. [51].

Raw reflectance spectra were processed via a statistical analysis software package, R version 2.11.0 [97] using custom "R" routines per Brown et al. [59]. These routines involved (i) a parabolic splice to correct for "gaps" between detectors, (ii) averaging replicate spectra, (iii) fitting a weighted (inverse measurement variance) smoothing spline to each spectra with direct extraction of smoothed reflectance at 1 nm intervals. Furthermore, in order to reduce the influence of the side information contained in the original reflectance spectra, Savitzky-Golay first derivative transformation was applied using a first-order polynomial across a ten band window. The transformation was implemented in the Unscrambler®X 10.3 software (CAMO Software Inc., Woodbridge, N.J.). Only first derivative spectra were used in subsequent multivariate models.

All samples were also scanned using a DP-6000 Delta Premium PXRF (Olympus, Waltham, Mass., USA). The instrument features a Rh X-ray tube operated at 15-40 keV with quantification via ultra-high resolution (b165 eV) silicon drift detector. Prior to soil analysis, the instrument was calibrated using a 316 alloy clip, containing 16.13% Cr, 1.78% Mn, 68.76% Fe, 10.42% Ni, 0.20% Cu, and 2.10% Mo, tightly fitted over the aperture. The instrument was operated in "Soil Mode" capable of detecting the following suite of elements: Sr, Zr, Mo, Ag, Cd, Sn, Sb, Ti, Ba, Cr, Mn, Fe, Co, Ni, Cu, Zn, Hg, As, Se, Pb, Rb, P, S, Cl, K, Ca, and V. Soil Mode consists of three beams which operate sequentially. Each beam was set to scan for 30 s such that one whole scan was completed in 90 s. As the PXRF analysis window is small (approximately 2 $cm^2$), it is important that the average composition of the sample is well represented within this area. Soil samples were carefully mixed to ensure sample homogeneity before scanning. Also, the aperture of the instrument was kept clean by air blowing to prevent soil or dust from contaminating the aperture window after each scan. Elemental data was stored in the onboard computer, and then downloaded into MS Excel for analysis.

In this study, AR grade (Sigma) chemicals were used without further purification. All solutions were prepared with MilliQ™ (18.2 M®) water and sterilized by filtration (0.44 μm pore) or by autoclave at 120° C.

A general TPH method was used to analyze oil content in soil samples (EPA method 8015 M); soils were first extracted using methylene chloride, and then extracts were analyzed by an HP6890 gas chromatograph (Hewlett-Packard, CA, USA) with flame ionization detection (GC-FID). Initial oven temperature (100° C.) was held for 1 min, followed by a 10° C. min-1 ramp to 275° C. and final hold for 5 min. The FID temperature was 330° C.

A 7-point calibration curve was constructed using weathered (30 days) Macondo collected off the coast of Louisiana following the 2010 Deepwater Horizon oil spill. Quantification of TPHs was accomplished by summing the areas for 2-3 integrations of all gas chromatographic peaks beginning with n-hexane (n-C6) and ending with n-pentatriacontane (n-C35) similar to TNRCC Method 1005.

All statistical modeling was performed using R version 2.11.0 [97] software. A normality check was performed using the Shapiro-Wilk test statistic at a 5% significance level. In the present study, Box-Cox transformation [6] was applied to the original positively skewed TPH data (Pearson skewness coefficient: 1.10) using $\lambda=0$ ($\log_{10}$ transformed). Moreover, due to the presence of several control samples with 0 mg kg-1 TPH values, $\log_{10}$ (TPH+1) was predicted as a target instead of $\log_{10}$ TPH.

Initially, $\log_{10}$ (TPH+1) was targeted with VisNIR data via partial least squares regression (PLS), random forest regression (RF), and penalized spline regression (PSR) [56, 148]. The whole dataset was randomly divided only into a ~75% training set (n=81) for calibration and a ~25% independent validation set (n=27) to prevent overfitting. Each time, the three methods were applied on the training set and validated by test samples. The optimum number of PLS latent factors (rotations of principal components for a slightly different optimization criterion) was selected on the basis of the number of factors with the smallest total residual validation Y-variance or highest total explained validation Y-variance. Outliers were carefully examined by marking the one-by-one and plotting the X-Y relation outliers for several model factors to monitor their influence on the shape of the X-Y relationship. For PSR, the cubic B-spline was used via R version 2.14.1 [97] as the base function with 100 equally spaced knots. The order of the penalty was set to the default value of three. The optimal value for the penalty-tuning parameter was selected by minimizing the leave-one-out-cross-validation (LOOCV) error on the training set. Moreover, the 'random Forest' package was used in R to build the random forest model. The number of trees in random forest was set to the default value of 500. The coefficient of determination ($R^2$), RMSE, residual prediction deviation (RPD) (Eq. (2)), ratio of performance to inter-quartile distance (RPIQ), and bias (Eq. (3)) were used as rubrics for judging model generalizability [13, 143, 131].

$$RPD = \left[\frac{1/(n-1)\sum_{i=1}^{n}(Yobs - Ymean)^2}{1/n\sum_{i=1}^{n}(Yobs - Ypred)^2}\right]^{0.5}_{Validation} \quad \text{Equation 2}$$

$$Bias = \sum_{i=1}^{n}(Ypred - Ymean)/n \quad \text{Equation 3}$$

where, Yobs and Ypred are the observed and predicted response variables, respectively, Ymean is the mean of the Yobs values, and n is the number of soils in the validation data set.

Figure 21:
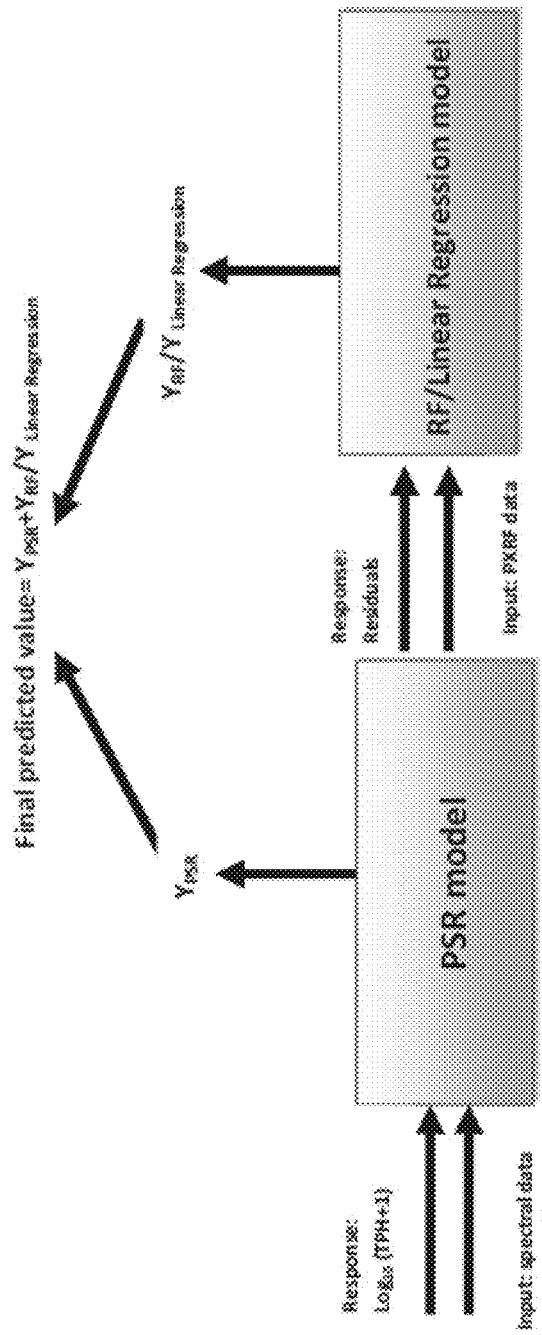
FIG. 21 is a schematic diagram of fused PSR+RF and PSR+linear regression prediction models used in the study.

Subsequently, to test whether simple concatenation of PXRF elemental data with VisNIR DRS spectra can improve TPH accuracy, the aforementioned algorithms were used further. Besides, an advanced fused modeling approach (PSR+RF) was employed where PSR was used to fit the training set (containing spectra only) using LOOCV to choose the tuning parameter. Next, RF was used to fit the residual on the PXRF elemental data (FIG. 21). Further, another fused model (PSR+linear regression) was tried to compare with PSR+RF, since linear regression is a popular classic model.

Additionally, principal component analysis (PCA) was applied for qualitative PXRF+VisNIR DRS-based discrimination of contaminated and control soil samples. The cumulative proportion of variance explained by the leading principal components (PC) was used to extract optimum PCs. Furthermore, pairwise scatterplots of the first two PCs were produced to provide visual assessment of how contaminated and control samples were separated in the PC space. PCA was performed using R version 2.11.0 (function: prcomp).

Descriptive statistics of the different soil properties analyzed in this study are given in Table 9. Notably, not all elements were quantified with discreet values via PXRF. Thus, only Al, Si, K, Ca, Ti, Mn, Fe, Cu, Zn, Rb, Sr, Y, Zr, and Pb were viable for regression, with discreet values across all soil samples scanned. Half of the collected samples exhibited the incidence of V, Ni, and As which are normal constituents of crude oil. As reported earlier, some of the abovementioned metals perhaps originated as organo-metallic compounds in crude oil from which researchers have identified the geoporphyrins of V, Ni, Cu, and Zn [144].

The results converged with Grujic et al. [147] who reported contamination of Pb, Cu, and Zn while investigating heavy metals in petroleum-contaminated surface soils of Serbia. The results also corroborated the salient findings of Gondal et al. [144], where laser induced breakdown spectroscopy revealed the presence of several trace elements in the residue of crude oil samples. While original TPH values were non-normally (Shapiro-Wilk stat=0.873, p-value b 0.0001) distributed from 0 to ~3 Å~106 mg kg-1, log 10 (TPH+1) contents ranged from 0 to 5.51 mg kg$^{-1}$ and were used as the dependent variable for subsequent predictive modeling (Table 9). For control samples, the mean TPH content of 203.2 mg kg$^{-1}$ was expectedly lower than mean TPH of contaminated samples (89,518.6 mg kg$^{-1}$) and also exhibited less variability. A similar trend was observed in earlier studies [129, 157, 158, 128], signifying petroleum hydrocarbon pollution. Strikingly, the magnitude of mean TPH obtained for the control samples (203.2 mg kg$^{-1}$) was several folds higher than the range of 1.00-26.63 mg kg$^{-1}$ earlier reported for unpolluted soils [127, 149, 157, 128], underlining that several seemingly control samples were actually somewhat contaminated, yet undetected by simple visual inspection.

Figure 22:
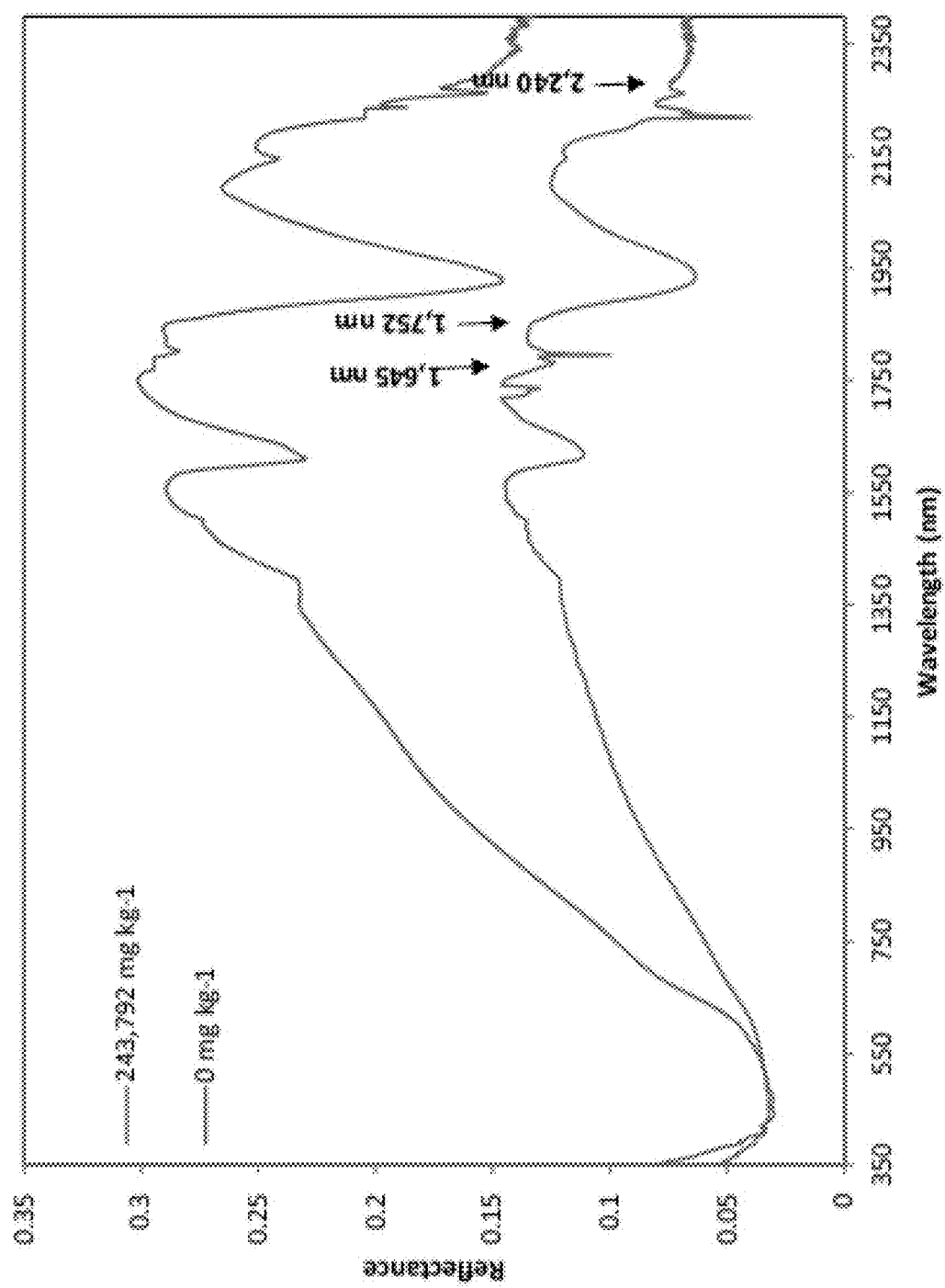
FIG. 22 is a graph of average reflectance spectra are shown for two soil samples of the Olton soil series with high total petroleum hydrocarbon content (243,792 mg $kg^{-1}$, blue) and zero total petroleum hydrocarbon (control, red). Spectral absorption maximums of petroleum at ~1645 nm, 1752 nm, and ~2240 nm are apparent in mean spectral reflectance curve of contaminated sample.

Average reflectance spectra for two soil samples from the Olton soil series with high TPH content (243,792 mg kg$^{-1}$) and no TPH (control) are shown in FIG. 22. In general, reflectance spectra for both contaminated and control soils were similar regarding high optical density [log (1/R)] in the visible light region (350-750 nm) and two distinct absorption peaks around 1900 (water absorption bands) and 2200 nm (metal-hydroxyl stretching), as reported in the literature [138]. In the NIR region (700-2500 nm), mean spectral reflectance decreased as contamination increased causing higher absorbance and reflecting less light than control samples [150]. The specific absorption minima of petroleumat ~1645 nm (C—H stretching modes of ArCH linked to polycyclic aromatic hydrocarbons), 1752 nm (C—H stretching mode of saturated $CH_2$ group in the first overtone region), and ~2240 nm (stretch+bend) of the NIR band were obvious [155, 159, 167]. While the locations of aforementioned first and last signature were a bit shifted from the exact anticipated positions (1647 nm and 2298 nm, respectively), it was natural in the sense that real molecules do not behave totally harmonically. Other researchers identified that the first overtone of the C—H band makes the most important contribution for analysis of oil systems [130]. However, these features were practically absent in the control reflectance curve.

Figure 23:
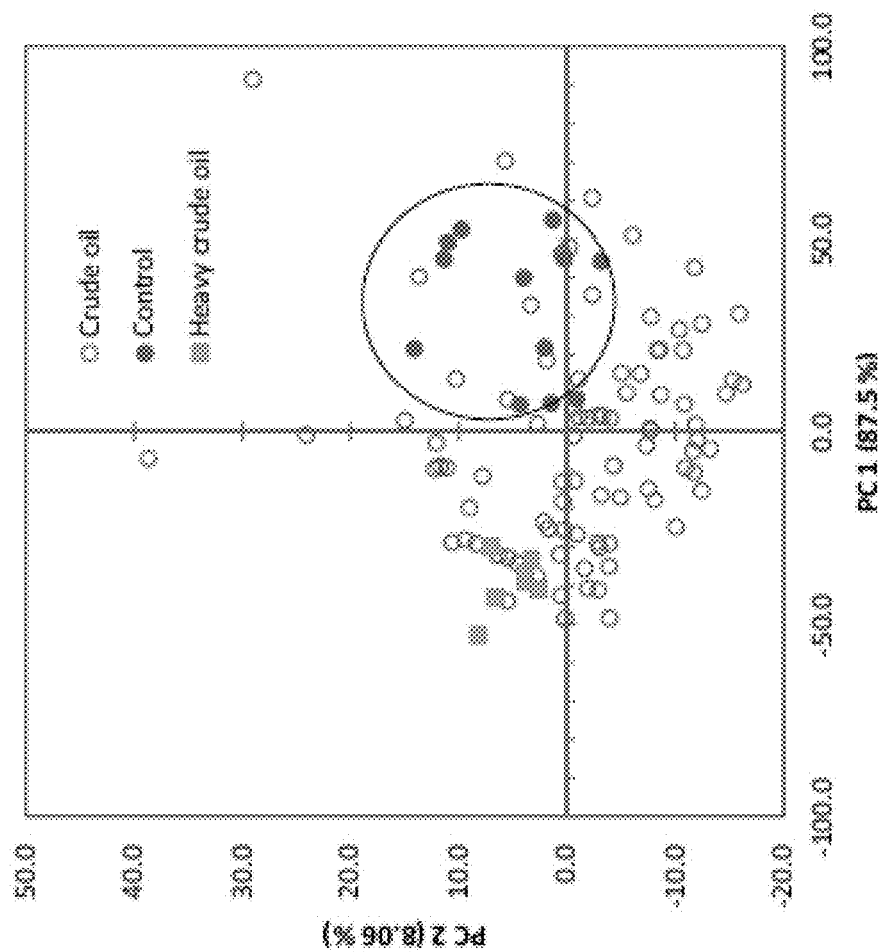
FIG. 23 is a pairwise principal component plot for PC1 vs. PC2 for qualitative PXRF+VisNIR DRS based discrimination of contaminated and control soil samples. Red circles, hollow circles, and green squares represent control samples, crude oil contaminated samples, and heavy crude oil contaminated samples, respectively.

Despite the high dimensionality of the spectral data (2151 channels from 350 to 2500 nm at 1-nm intervals) and PXRF data (14 elements), almost 100% of the variation was primarily explained by the first six PCs (99.22%). FIG. 23 illustrates how the pairwise PC score plot discriminated control soils from soils contaminated with crude oil and heavy crude oil (six samples containing N90,000 mg $kg^{-1}$ TPH) along PC 1. Conversely, heavy crude oil samples were mixed with crude oil samples due to their compositional resemblance. Since the samples in the heavy crude oil set belonged to a single soil series (Mobeetie/Potter), they showed smaller spectral variation and their data cloud was compact. Conversely, the higher spectral diversity exhibited by the crude oil contaminated set indicated that it was compositionally diverse. The results justified the ability of the PXRF+VisNIR DRS system to capture the intrinsic data structure in a two-dimensional representation.

Three multivariate regression techniques were used to relate the PXRF elements and VisNIR DRS reflectance spectra to TPH contents with independent validation. Accuracy and stability of different multivariate models were evaluated according to the RPD-based rules of Chang et al. [13]. Since RPD is the ratio of standard deviation and RMSE, model predictability is enhanced when the validation set standard deviation (SD) is comparatively larger than the estimation error (RMSE). Good, fair, and unreliable prediction models are characterized by RPDs of N2.0, 1.4-2.0, and b1.40, respectively. In this study, model RMSE and bias of (TPH+1) were reported as $log_{10}$ mg $kg^{-1}$ and these values were only used for comparing multivariate models as they did not represent the expected error in concentration.

While using VisNIR spectra only, the PLS model ($R^2$=0.73, RMSE=0.59 $log_{10}$ mg $kg^{-1}$, RPD=1.96, RPIQ=0.63) outperformed both PSR and RF models (Table 10). In order to investigate whether using PXRF elemental data as predictors in addition to VisNIR spectra can improve TPH predictability, a PSR+RF model was constructed and produced the best accuracy relative to other models tested. Moreover, while incorporating PXRF data, the PLS model was somewhat able to prevent overfitting with fewer PLS latent factors (1). Apart from producing the highest RPD of 2.19, the PSR+RFmodel also exhibited the highest validation coefficient of determination (0.78) and RPIQ (0.75), suggesting satisfactory and effective calibration of (TPH+1).

Figures 24A, 24B, 24C:
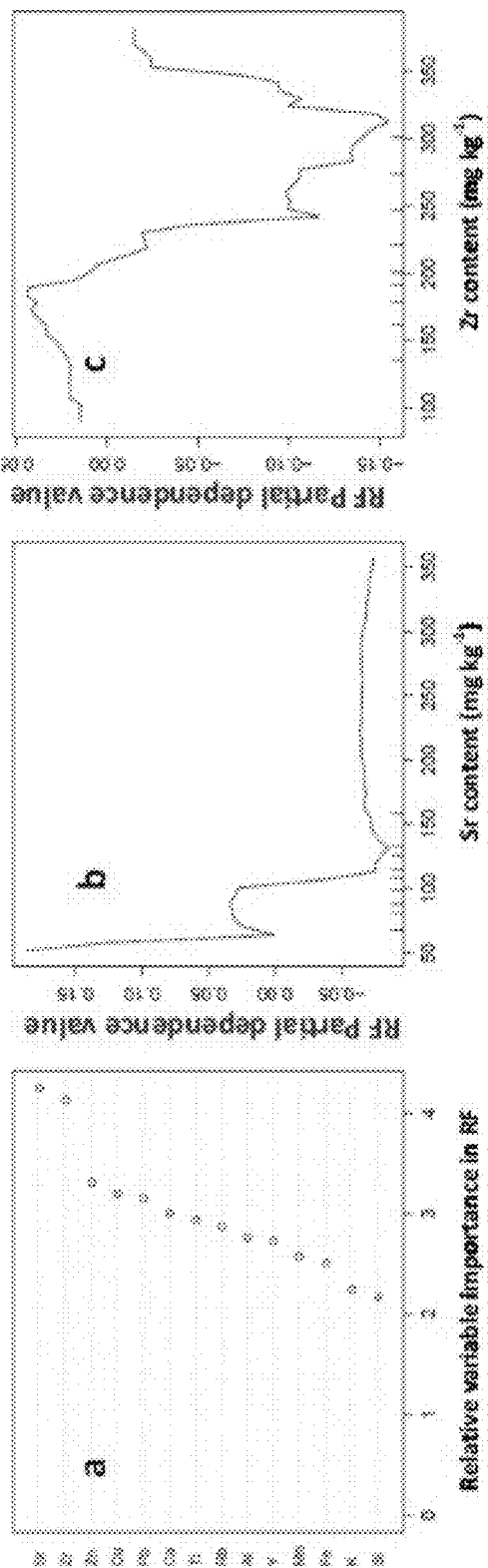
FIGS. 24A-24C are plots showing a) RF relative variable importance for each of the PXRF elements used in PSR+RFmodel and RF partial dependence function of b) Sr and c) Zr on the residuals of PSR model.
Figure 25B:
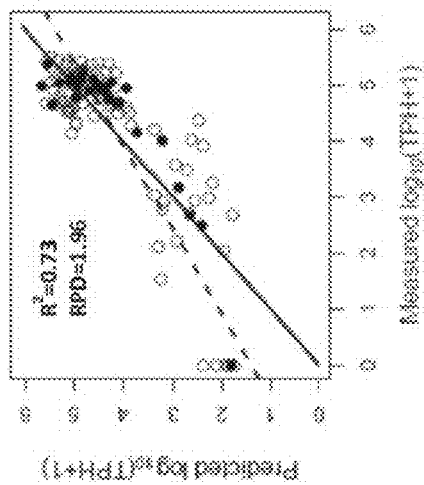
FIGS. 25A-25D are laboratory measured versus PXRF+VisNIR DRS predicted (TPH+1) concentration ($\log_{10}$ mg $kg^{-1}$) using four multivariate models. LR represents linear regression. The dashed line is the regression line, and the solid line is a 1:1 line. White and black circles represent calibration and validation samples, respectively.
Figure 25D:
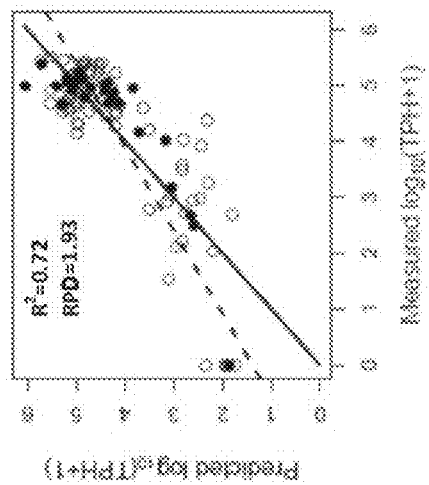
Figure 25A:
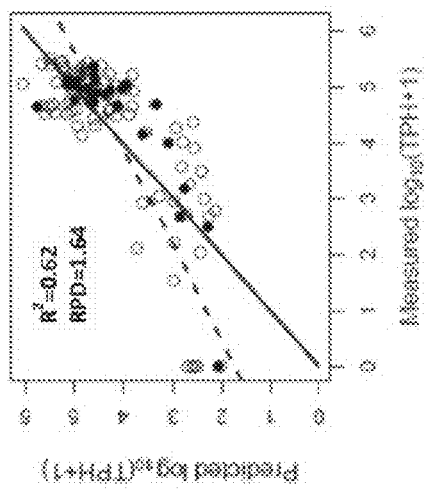
Figure 25C:
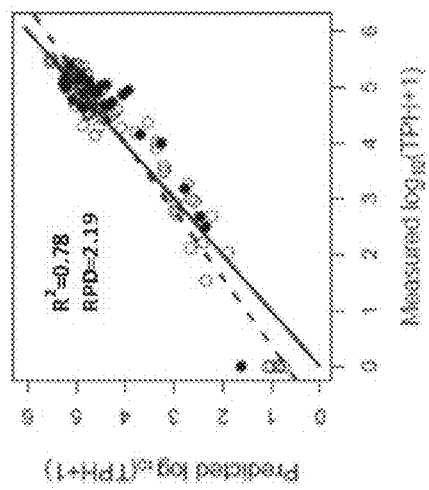

Conversely, PSR+linear regression performed similarly as PSR, producing a fair RPD of 1.93. While comparing the PSR+RF and PSR+linear regression, it was evident that using RF on the residuals achieved better performance than linear regression. FIGS. 24A-24C comprehensively explains the rationale behind the better performance of PSR+RF, where FIG. 24A exhibits the RF relative variable importance for each of the PXRF elements. It was apparent that Sr and Zr were the two most influential ones, corroborating earlier studies [139]. Moreover, RF partial dependence plots (FIGS. 24B and 24C) exhibit clear non-linear effects of Sr and Zr on the residuals of the PSR model, respectively. Note that the partial dependence function shows the effect of a variable on the response in deciles (e.g., 10 percentile, 20 percentiles, etc.) after accounting for the average effects of all other variables in the model. Partial dependence plots provide a useful tool for interpreting the effects of a variable on the response particularly when there are no or weak interactions in the data or predictors. Details of the partial dependence function can be found in Friedman [142]. Another possible explanation for better performance of RF could be its ability to handle the interactions among these elemental variables implicitly while in a linear regression model the researcher has to select wisely and explicitly the interaction terms in the model.

From lab-measured versus model predicted (TPH+1) plots, it was clear that the PSR model showed overestimation at lower values [i.e., $log_{10}$ (TPH+1) is b2 mg $kg^{-1}$] and underestimation at higher values [i.e., $log_{10}$ (TPH+1) between 2 and 4.5 mg $kg^{-1}$] (FIGS. 25A-25D). Exhibiting a similar trend and scattering from the 1:1 line, the prediction decreased further for the PLS model. There were only a few observations with zero $log_{10}$ (TPH+1) mg $kg^{-1}$ which contributed to the overprediction of low (TPH+1) values. Conversely, PSR+RF models closely approximated the 1:1 line, improving prediction accuracy. However, bias made a significant contribution to the overall lack of validation fit (>20% of MSE) for all models tested. The bias was expected due to the fact that the heterogeneity of sample origin was so large and that the validation set was perhaps quite different from the calibration set. A key requirement for model validation is that the validation samples should be independent and preferably scanned with different spectroradiometers [59]. While the latter requirement was not logistically achieved, the samples used in this study were otherwise independent.

Figure 26:
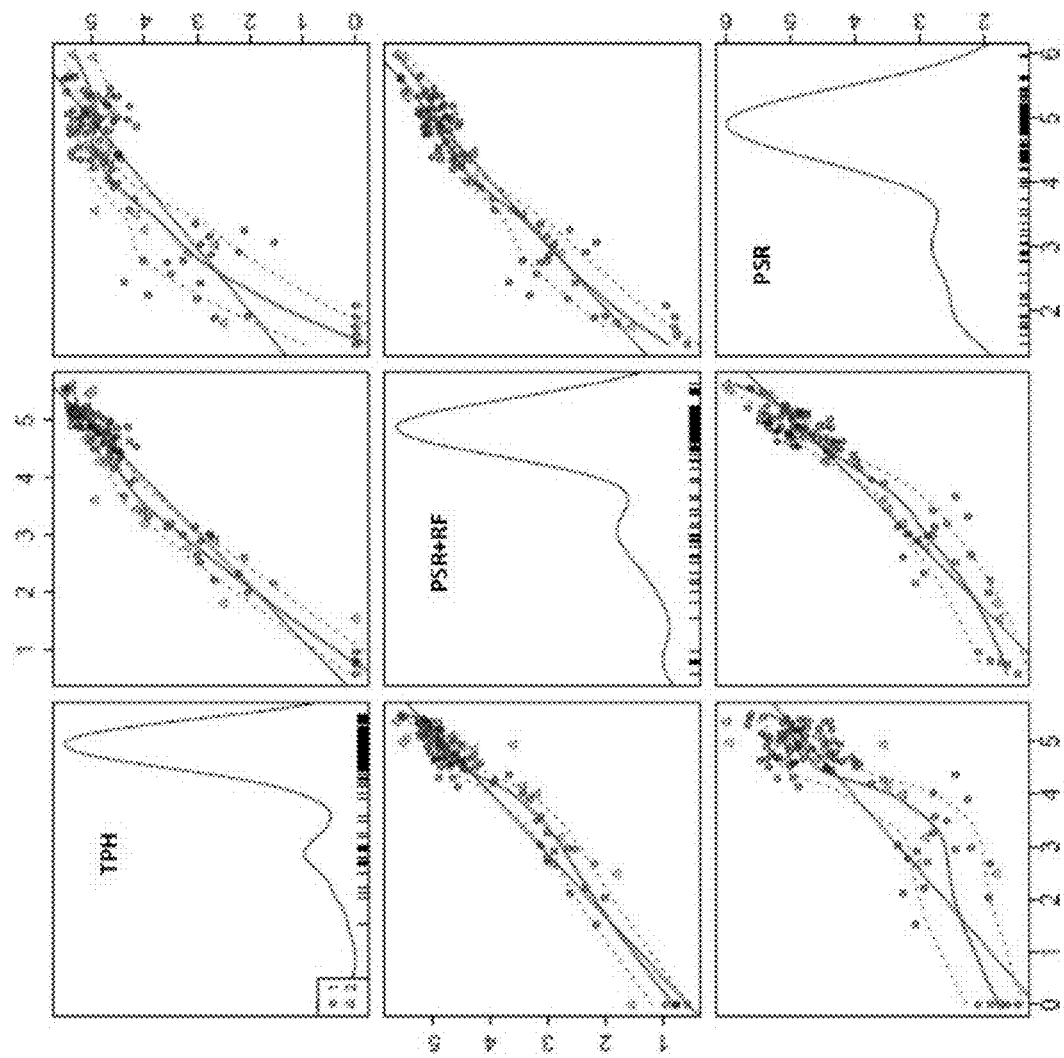
FIG. 26 are diagnostic scatter plot matrix showing density plots for three competitors: observed value (TPH+1), penalized spline regression (PSR), and fused penalized spline random forest regression (PSR+RF). Black circles and red triangles are training and validation samples, respectively. The black and red solid lines are the fitted linear regression line and the loess smoother fit, respectively. The red dash lines represent one standard error above 15 and below the estimated function. For diagonal plots, the vertical axis shows the density function for its corresponding values. For example, the top left one is the density plot of log 10 (TPH+1). In the off-diagonal plots, their axes are all in the $\log_{10}$ mg $kg^{-1}$ unit. For example, for the bottom left one, the horizontal axis is the $\log_{10}$ (TPH+1) mg $kg^{-1}$ and the vertical axis title is the predicted $\log_{10}$ (TPH+1) mg $kg^{-1}$ values from PSR.

To clearly visualize the prediction improvement by using the fused PSR+RF model, FIG. 26 represents a scatterplot matrix produced in R using the spm function in the car library. The diagonal elements are the density plots for the three competitors [observed value (TPH+1), PSR, and PSR+RF]. For example, the upper left one is the density plot of TPH [i.e., log 10 (TPH+1)]. While the tick marks at the bottom axis show the observed values in the data, the curve is the smoothed density function of TPH and skewed to the left. The off-diagonal elements are the pairwise scatter plots of three competitors, together with the best linear and nonlinear smoothers. For example, the upper middle one shows the scatter plot of observed TPH (on the vertical axis) and predicted PSR+RF values (on the horizontal axis) using spectral data. The black and red solid lines are the fitted linear regression line and the loess smoother (a popular nonlinear smoother using local linear regression) fit, respectively. The red dash lines represent one standard error above and below the estimated function. It can be observed that the density functions of TPH and PSR+RF were more similar to each other than PSR to TPH. PSR estimates had a heavier tail than the ones from the observed TPH and PSR+RF estimates. This implied that PSR tended to underestimate the samples with small values of TPH between 2 and 4.5 [i.e., $\log_{10}$ (TPH+1)]. This was further confirmed by observing the lower left scatter plot of TPH (on the horizontal axis) and PSR estimates (on the vertical axis). It can be seen that many points were below the linear regression line when TPH was between 2 and 4.5, implying that those underestimated samples from the PSR model have been lifted up by applying the RF on the PSR residuals. This was not surprising given the non-linear and contingent relationships between VisNIR DRS reflectance and soil composition [64].

In addition, the ratio of PSR+RF to other model results revealed some interesting trends, where the PSR+RF fused model clearly improved the coefficient of determination and RPD and lowered RMSE as compared to other models tested. A 14% increase in RPD was observed while using PSR+RF as compared to PSR+linear regression. Notably, the fused model alone produced ~20% higher RPD than average RPDs of VisNIR DRS-based models, clearly highlighting the improvement by including PXRF elements with reflectance spectra.

In this study, one obvious question was whether it is possible to directly analyze soil petroleum contamination in fresh samples by PXRF+VisNIRDRS. This question was critical as we attempted to develop models which could ultimately lead to in-situ measurements. Given that, VisNIR DRS can sense the changes in the matrix material scanned, particularly moisture (as it relates to O—H bonding and color) [55, 126], bringing the soil samples to standard water content (field capacity) prior to scanning is critical for obtaining consistent results. However, although under laboratory controlled conditions soil can be scanned under uniform moisture content, maintaining unique water content in the field is not easy. Even in air-dried conditions, water remains adsorbed on the surface areas of clay minerals (e.g., hygroscopic water) and organic matter in equilibrium with atmospheric water vapor. Interestingly, even pretreatment methods like quick-freezing and freeze-drying were unable to remove the water completely from the layer minerals of soil [111]. Thus, in this study we relied on our earlier finding that the presence of moisture does not substantially reduce the predictability of TPH [12]. Researchers have also reported that NIR spectra calibrated using field soil samples can be used for field prediction of soil properties [137, 152, 57]. Despite that, establishing the best sample pretreatment (field-moist or air-dried) was beyond the scope of this study and requires further investigations. Hence, influence of variable moisture remains one of the big issues to be addressed about calibrations for soil petroleum contamination. Even so, our approaches may be minimally impacted by soil moisture in many arid regions of the world where oil production is commonplace (e.g., Middle East, West Texas).

Summarily, although VisNIR DRS earlier showed considerable promise in providing rapid soil petroleum contamination prediction with reasonable accuracy, adding PXRF elemental data as auxiliary predictors was beneficial and should be included to model soil TPH. Brown et al. [59] postulated that VisNIR DRS alone will never give complete soil characterization, thus application in parallel with other sensing technologies should be a focus of future research. Acquisition of PXRF data is rapid, easy, and cost-effective. While we concede that the initial purchase/investment of the equipment might seem high (perhaps ~$100,000), the savings moving forward quickly recover the capital investment. As stated earlier, the proposed hybrid PXRF+VisNIR DRS system requires no consumables, minimum to no laboratory preparation time, and no laboratory facilities. In a traditional laboratory, analysis of TPH and heavy metals can easily cost $100 per sample or more and require days or weeks of laboratory processing. At that price, the cost of the hybrid PXRF+VisNIR DRS system would be recovered after 1000 or fewer samples; an attractive benefit for regulators and remediation specialists alike. Besides, as these instruments are field portable, direct assessment in-situ is also possible. Both evaluated techniques share the advantage of determining soil TPH especially for unusual circumstances where non-destructive sampling is required. Finally, our approaches provide more than just soil petroleum contamination, they provide specific elemental analyses; thus, more comprehensive information than simple TPH readings. Additional research should be continued to include larger geographical ranges along with other soil properties, but the future of PXRF+VisNIR DRS-based soil TPH characterization appears promising.

Summarily, we have demonstrated the potential of using a PSR+RF model using PXRF+VisNIR DRS data as a viable method for rapid and low-cost quantification of soil petroleum contamination as an addition to the standard methods for soil TPH analysis. We intended to test the capability of PXRF+VisNIR DRS viability instead of making a labgrade predictive model. This study used a total of 108 petroleum contaminated and control soil samples from West Texas for scanning via VisNIR spectrometer and PXRF, followed by correlating diffuse reflectance data and elemental data with lab-determined soil TPH values. The advanced fused PSR+RF model using first derivative spectra outperformed all models tested, producing 78% variability of the independent validation set and a quality RPD (2.19). Unsupervised PCA also qualitatively separated contaminated soils from control samples. Hence, PXRF+VisNIR DRS showed the potential to be used as a postspill rapid soil contamination monitoring tool. In this present feasibility study, we have presented a preliminary contribution to this problem and further intensive research is recommended to confirm the results here obtained. We anticipate that the future development of synthesized PXRF+VisNIR DRS methods and the expansion of soil-spectral libraries will support the assessment of soil petroleum contamination variability at a scale and resolution not previously possible.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

All of the systems, devices, computer programs, compositions and/or methods disclosed and claimed herein can be made and executed without undue experimentation in light of the present disclosure. While the systems, devices, computer programs, compositions and methods of this invention have been described in terms of preferred embodiments, it will be apparent to those of skill in the art that variations may be applied to the systems, devices, computer programs, compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] AlaviPanah, S. K., Goossens, R., 2001. Relationship between the Landsat TM, MSS Data and soil salinity. J. Agric. Sci. Technol. 3, 21-31.
[2] Andrews, S. S., Karlen, D. L., Cambardella, C. A., 2004. The soil management assessment framework. Soil Sci. Soc. Am. J. 68, 1945-1962.
[3] Argyraki, A., Ramsey, M. H., Potts, P. J., 1997. Evaluation of portable X-ray fluorescence instrumentation for in situ measurements of lead on contaminated land. The Analyst. 122,743-749.
[4] Barnes, R. J., Dhanoa, M. S., Lister, S. J., 1989. Standard normal variate transformation and de-trending of near infrared diffuse reflectance spectra. Appl. Spectrosc. 43, 772-777.
[5] Bilgili, A. V., Cullu, M. A., Van Es, H. M., Aydemir, A., Aydemir, S., 2011. The use of hyperspectral visible and near infrared reflectance spectroscopy for the characterization of salt-affected soils in the Harran lain, Turkey. Arid Land Res. and Mgt. 25(1), 19-37.
[6] Box, G. E. P., Cox, D. R., 1964. An analysis of transformations. J. Roy. Stat. Soc. Ser. B. Methodol. 26, 211-252.
[7] Brady, N.C., Weil, R. R., 2008. The nature and properties of soils. 14th Ed. Prentice Hall, Upper Saddle River, N.J. pp. 975.
[8] Buddenbaum, H., Steffens, M., 2012. The effects of spectral pre-treatments on chemometric analyses of soil profiles using laboratory imaging spectroscopy. Appl. Environ. Soil. Sci. http://dx.doi.org/10.1155/2012/274903.
[9] Clark, R. N., King, T. V. V., Klejwa, M., Swayze, G. A., Vergo, N., 1990. High spectral resolution reflectance spectroscopy of minerals. Journal of Geophysical Research 95 (B8), 12653-12680.
[10] Clay, D. E., Chang, J., Malo, D. D., Carlson, C. G., Reese, C., Clay, S. A., Ellsbury, M., Berg, B., 2001. Factors influencing spatial variability of soil apparent electrical conductivity. Communications in Soil Science and Plant Analysis 32(19-20), 2993-3008.
[11] Chakraborty, S., Weindorf, D. C., Ali, N., Li, B., Ge, Y., Darilek, J. L., 2013. Spectral data mining for rapid measurement of organic matter in unsieved moist compost. Appl. Opt. 52, B82-B92.
[12] Chakraborty, S., Weindorf, D. C., Li, B., Ali, N., Majumdar, K., Ray, D. P., 2014. Analysis of petroleum contaminated soils by spectral modeling and pure response profile recovery of n-hexane. Env. Poll. 190, 10-18.
[13] Chang, C., Laird, D. A., Mausbach, M. J., Hurburgh, C. R., 2001. Near infrared reflectance spectroscopy: Principal components regression analysis of soil properties. Soil Sci. Soc. Am. J. 65, 480-490.
[14] Csillag, F., Pásztor, L., Biehl, L. L., 1993. Spectral band selection for the characterization of salinity status of soils. Remote Sensing of Env. 43, 231-242.
[15] Eldeiry, A. A., Garcia, L. A., 2008. Detecting soil salinity in alfalfa fields using spatial modeling and remote sensing. Soil Sci. Soc. Am. J. 72(1), 201-211.
[16] Farifteh, J., Farshad, A., George, R. J., 2006. Assessing salt-affected soils using remote sensing, solute modelling, and geophysics. Geoderma 130(3), 191-206.

[17] Farifteh, J., Van der Meer, F., Atzberger, C., Carranza, E. J. M., 2007. Quantitative analysis of salt-affected soil reflectance spectra: A comparison of two adaptive methods (PLSR and ANN). Remote Sensing of Env. 110(1), 59-78.

[18] Haaland, D. M., Thomas, E. V., 1988. Partial least-squares methods for spectral analyses. 1. Relation to other quantitative calibration methods and the extraction of qualitative information. Anal. Chem. 60, 1193-1202.

[19] Ji, J. F., Balsam, W., Chen, J., Liu, L. W., 2002. Rapid and quantitative measurement of hematiteand goethite in the Chinese loess-paleosol sequence by diffuse reflectancespectroscopy. Clays and Clay Minerals 50 (2), 208-216.

[20] Jones, A. A., 1982. Methods of Soil Analysis—Part 2: Chemical and Microbiological Properties. Soil Science Society of America, Madison, Wis.

[21] Kalra, N. K., Joshi, D. C., 1996. Potentiality of Landsat, SPOT and IRS satellite imagery, for recognition of salt affected soils in Indian Arid Zone. International J. of Remote Sensing 17(15), 3001-3014.

[22] Karlen, D. L., Tomer, M. D., Neppel, J., Cambardella, C. A., 2008. A preliminary watershed scale soil quality assessment in north central Iowa, USA. Soil and Tillage Res. 99(2), 291-299.

[23] Khan, N. M., Rastoskuev, V. V., Shalina, E. V., Sato, Y., 2001. Mapping salt-affected soils using remote sensing indicators—a simple approach with the use of GIS IDRISI. Paper presented at the 22nd Asian Conference on Remote Sensing. Vol. 5, p. 9.

[24] Loveday, J., 1974. Recognition of gypsum responsive soils. Aust. J. Soil Res. 12, 87-96.

[25] Martens, H., Naes, T., 1989. Multivariate Calibration, Wiley, New York, USA.

[26] Metternicht, G., Zinck, A., (eds). 2008. Remote sensing of soil salinization: Impact on land management. CRC Press, Boca Raton, Fla.

[27] National Aeronautics and Space Administration, 2014. NASA's earth observing system data and information system (EOSDIS). Available at http://reverb.echo.nasa.gov/reverb/#utf8=%E2%9C%93&spatial_map=satellite&spatial_type=rectangle (verified 21 Apr. 2014).

[28] Otto, O., 1998. Statistics and Computer Application in Analytical Chemistry. Wiley-VCH, Weinheim, Germany.

[29] Pozdnyakova, L., Zhang, R., 1999. Geostatistical analyses of soil salinity in a large field. Precision Agriculture 1(2), 153-165.

[30] Rayment, G. E., Higginson, F. R., 1992. Australian laboratory handbook of soil and water chemical methods. Inkata Press, Sydney.

[31] Rhoades, J. D., Chanduvi, F., Lesch, S. M., 1999. Soil salinity assessment: Methods and interpretation of electrical conductivity measurements. Food and Agricultural Organization, Rome, Italy.

[32] Saeys, W., Mouazen, A. M., Ramon, H., 2005. Potential for onsite and online analysis of pig manure using visible and near infrared reflectance spectroscopy. Biosystems Engineering 91, 393-402.

[33] Shacklette, H. T., Boerngen, J. G., 1984. Element concentrations in soils and other surficial materials of the conterminous United States. U.S. Geol. Surv. Prof. Pap. 1270. U.S. Geological Survey, Alexandria, Va.

[34] Sonmez, S., Buyuktas, D., Okturen, F., Citak, S., 2008. Assessment of different soil to water ratios (1:1, 1:2.5, 1:5) in soil salinity studies. Geoderma 144, 361-369.

[35] Soil Salinity Staff, 1954. Diagnosis and improvement of saline and alkali soils. USDA Agricultural Handbook No. 60. US Gov. Print. Office, Washington, D.C.

[36] Soil Survey Staff, 2006. Land resource regions and major land resource areas of the United States, the Caribbean, and the Pacific Basin. USDA-NRCS. Available at http://www.nrcs.usda.gov/wps/portal/nrcs/detail/soils/survey/?cid=nrcs142p2_053624 (verified 10 Mar. 2014).

[37] Soil Survey Staff, 2014a. Official soil series descriptions. USDA-NRCS. Available online at https://soilseries.sc.egov.usda.gov/osdname.asp (verified 10 Mar. 2014).

[38] Soil Survey Staff, 2014b. Web soil survey. USDA-NRCS. Available online at http://websoilsurvey.sc.egov.usda.gov/App/HomePage.htm (verified 21 Apr. 2014).

[39] Swanhart, S., 2013. Measuring soluble salts in soils via portable x-ray fluorescence spectrometry. MS thesis. Louisiana State University, Baton Rouge.

[40] Tamás, J., Lénárt, C., 2006. Analysis of a small agricultural watershed using remote sensing techniques. International J. of Remote Sensing 27(17), 3727-3738.

[41] United State Geological Survey (USGS), 2014a. Frequently asked questions about the Landsat missions. Available online at http://landsat.usgs.gov/band_designations_ landsat_satellites.php (verified 21 Apr. 2014).

[42] United States Geological Survey (USGS), 2014b. Earth explorer. Available at http://earthexplorer.usgs.gov (verified 21 Apr. 2014).

[43] Van der Voet, H., 1994. Comparing the predictive accuracy of models using a simple randomisation test. Chemometrics and Intelligent Laboratory Systems 25, 313-323.

[44] Vapnik, V., 1995. The Nature of Statistical Learning Theory. Springer, N.Y.

[45] Vinogradov, A. P., 1959. The geochemistry of rare and dispersed chemical elements in soils. 2nd ed. Consultants Bureau, New York, N.Y.

[46] Viscarra Rossel, R. A., Walvoort, D. J. J., McBratney, A. B., Janik, L. J., Skjemstad, J. O., 2006. Visible, near infrared, mid infrared or combined diffuse reflectance spectroscopy for simultaneous assessment of various soil properties. Geoderma 131, 59-75.

[47] Weindorf, D. C., Herrero, J., Castañeda, C., Bakr, N., Swanhart, S., 2013. Direct soil gypsum quantification via portable x-ray fluorescence spectrometry. Soil Sci. Soc. Am. J. 77, 2071-2077.

[48] White, W., 1971. Infrared characterization of water and hydroxyl ion in the basic magnesiumcarbonate minerals. American Mineralogist 56, 46-53.

[49] Williams, P. C., 1987. Variables affecting near-infrared reflectance spectroscopic analysis. In: Williams, P., Norris, K., (Eds.), Near-infrared technology in the agricultural and food industries. Am. Assoc. of Cereal Chemists, St. Paul, Minn., pp. 143-167.

[50] Zhu, Y., Weindorf, D. C., Zhang, W. 2011. Characterizing soils using a portable X-ray fluorescence spectrometer: 1. Soil texture. Geoderma 167-168, 167-177.

[51] Aldabaa, A. A. A., Weindorf, D. C., Chakraborty, S., Sharma, A., 2015. Combination of proximal and remote sensing methods for rapid soil salinity quantification. Geoderma 239-240, 34-46.

[52] An, X., Li, M., Zheng, L., Liu, Y., Sun, H., 2014. A portable soil nitrogen detector based on NIRS. Precis. Agric. 15, 3-16.

[53] Batjes, N. H., 1996. Total carbon and nitrogen in the soils of the world. Eur. J. Soil Sci. 47, 151-163.

[54] Bermner, J. M., 1996. Nitrogen-Total. In: Sparks, D. L. (Ed.), Methods of Soil Analysis—Part 3: Chemical Methods. SSSA, Madison, Wis., pp. 1085-1122.

[55] Bishop, J. L., Pieters, C. M., Edwards, J. O., 1994. Infrared spectroscopic analyses on the nature of water in montmorillonite. Clay Clay Miner. 42, 702-716.

[56] Breiman, L., 2001. Random forests. Mach. Learn. 45, 5-32.

[57] Bricklemyer, R. S., Brown, D. J., 2010. On-the-go VisNIR: potential and limitations for mapping soil clay and organic carbon. Comput. Electron. Agric. 70, 209-216.

[58] Brown, D. J., Bricklemeyer, R. S., Miller, P. R., 2005. Validation requirements for diffuse reflectance soil characterization models with a case study of VNIR soil C prediction in Montana. Geoderma 129, 251-267.

[59] Brown, D. J., Shepherd, K. D., Walsh, M. G., Dewayne Mays, M., Reinsch, T. G., 2006. Global soil characterization with VNIR diffuse reflectance spectroscopy. Geoderma 132, 273-290.

[60] Brunet, D., Bernoux, M., Barthès, B. G., 2008. Comparison between predictions of C and N contents in tropical soils using a Vis-NIR spectrometer including a fibre-optic probe versus a NIR spectrometer including a sample transport module. Biosyst. Eng. 100, 448-452.

[61] Carpenter, S. R., Caraco, N. F., Corell, D. L., Howarth, R. W., Sharpley, A. N., Smith, V. H., 1998. Nonpoint pollution of surface waters with phosphorus and nitrogen. Ecol. Appl. 8, 559-568.

[62] Chakraborty, S., Weindorf, D. C., Zhu, Y., Li, B., Morgan, C. L. S., Ge, Y., Galbraith, J., 2012. Spectral reflectance variability from soil physicochemical properties in oil contaminated soils. Geoderma 177-178, 80-89.

[63] Chakraborty, S., Das, B. S., Ali, N., Li, B., Sarathjith, M. C., Majumdar, K., Ray, D. P., 2014a. Rapid estimation of compost enzymatic activity by spectral analysis method combined with machine learning. Waste Manag. 34, 623-631.

[64] Clark, R. N., 1999. Spectroscopy of rocks and minerals, and principles of spectroscopy. In: Rencz, N. (Ed.), Remote Sensing for the Earth Sciences: Manual of Remote Sensing. John Wiley & Sons, New York, pp. 3-58.

[65] Compton, J. E., Boone, R. D., 2002. Soil nitrogen transformations and the role of light fraction organic matter in forest soils. Soil Biol. Biochem. 34, 933-943.

[66] Craswell, E. T., Lefroy, R. D. B., 2001. The role and function of organic matter in tropical soils. Nutr. Cycl. Agroecosyst. 61, 7-18.

[67] Dumas, J. B. A., 1831. Procedes De l'analyse organique. Ann. Chim. Phys. 247, 198-213.

[68] Eilers, P. H. C., Marx, B. D., 1996. Flexible smoothingwith B-spline and penalties (with comments and rejoinder). Stat. Sci. 11, 89-121.

[69] Fultz, L. M., Moore-Kucera, J., Zobeck, T. M., Acosta-Martinez, V., Wester, D. B., Allen, V. G., 2013. Organic carbon dynamics and soil stability in five semiarid agro-ecosystems. Agric. Ecosyst. Environ. 181, 231-240.

[70] Ge, Y., Morgan, C. L. S., Ackerson, J. P., 2014. VisNIR spectra of dried ground soils predict properties of soils scanned moist and intact. Geoderma 221-222, 61-69.

[71] Gogé, F., Gomez, C., Jolivet, C., Joffre, R., 2014. Which strategy is best to predict soil properties of a local site from a national Vis-NIR database? Geoderma 213, 1-9.

[72] Hoylea, F. C., Murphya, D. V., Fillery, I. R. P., 2006. Temperature and stubblemanagement influence microbial CO2-C evolution and gross N transformation rates. Soil Biol. Biochem. 38, 71-80.

[73] Hu, W., Huang, B., Weindorf, D. C., Chen, Y., 2014. Metals analysis of agricultural soils via portable X-ray fluorescence spectrometry. Bull. Environ. Contam. Toxicol. 92, 420-426.

[74] Hunt, G. R., 1977. Spectral signatures of particulate minerals in the visible and near infrared. Geophysics 42, 501-513.

[75] ISO (International Organisation for Standardisation), 2013. ISO 13196: 2013(E). Soil Quality—Screening Soils for Selected Elements by Energy-Dispersive X-Ray Fluorescence Spectrometry Using a Handheld or Portable Instrument. BSI Standards Publication, London, UK.

[76] Kjeldahl, J., 1983. Neue methode zur Bestmmung des Stickstoffs in organischen Korpern. Z. Anal. Chem. 22, 366-382.

[77] Krivobokova, T., 2006. Theoretical and Practical Aspects of Penalized Spline Smoothing. (Ph.D. dissertation). Bielefeld University, Bielefeld, Germany.

[78] Kuang, B., Mahmood, H. S., Quraishi, M. Z., Hoogmoed, W. B., Mouazen, A. M., van Henten, E. J., 2012. Chapter four—sensing soil properties in the laboratory, in situ, and online: a review. In: Donald, L. S. (Ed.), Advances in Agronomy. Academic Press, pp. 155-223. Lal, R., 2004. Soil carbon sequestration impacts on global climate change and food security. Science 304, 1623-1627.

[79] Lal, R., Kimble, J. M., Follett, R. F., Stewart, B. S., 2001. Methods of Assessment of Soil Carbon. CRC Press, Boca Raton, Fla.

[80] Lang, M., Cai, Z., Mary, B., Hao, X., Chang, S. X., 2010. Land-use type and temperature affect gross nitrogen transformation rates in Chinese and Canadian soils. Plant Soil 334, 377-389.

[81] Ledley, T. S., Sundquist, E. T., Schwartz, S. E., Hall, D. K., Fellows, J. D., Killeen, T. L., 1999. Climate change and greenhouse gases. EOS Trans. Am. Geophys. Union 80, 453-474.

[82] Lobell, D. B., Asner, G. P., 2002. Moisture effects on soil reflectance. Soil Sci. Soc. Am. J. 66, 722-727.

[83] Marx, B. D., Eilers, P. H. C., 1999. Generalized linear regression on sampled signals and curves: a P-spline approach. Technometrics 41, 1-13.

[84] McCarty, G. W., Reeves, J. B., 2006. Comparison of IR and MIR diffuse reflectance spectroscopy for field-scale measurement of soil fertility parameters. Soil Sci. 171, 94-102.

[85] McCarty, G. W., Reeves III, J. B., Reeves, V. B., Follett, R. F., Kimble, J. M., 2002. Mid-infrared and near-infrared diffuse reflectance spectroscopy for soil carbon measurement. Soil Sci. Soc. Am. J. 66, 640-646.

[86] McDowell, M. L., Bruland, G. L., Deenik, J. L., Grunwald, S., Knox, N. M., 2012. Soil total carbon analysis in Hawaiian soils with visible, near-infrared and mid-infrared diffuse reflectance spectroscopy. Geoderma 189-190, 312-320.

[87] Miller, R. W., Gardiner, D. T., 1998. Soils in Our Environment. Prentice Hall, Upper Saddle River, N.J.

[88] Minasny, B., McBratney, A., Bellon-maurel, V., Roger, J. M., Gobrecht, A., Ferrand, L., Joalland, S., 2011. Removing the effect of soil moisture from NIR diffuse reflectance spectra for the prediction of soil organic carbon. Geoderma 167-168, 118-124.

[89] Morgan, C. L. S., Waiser, T. H., Brown, D. J., Hallmark, C. T., 2009. Simulated in situ characterization of soil organic and inorganic carbon with visible near-infrared diffuse reflectance spectroscopy. Geoderma 151, 249-256.

[90] Mouazen, A. M., Maleki, M. R., De Baerdemaeker, J., Ramon, H., 2007. On-linemeasurement of some selected soil properties using a VIS-NIR sensor. Soil Tillage Res. 93, 13-27.

[91] Muñoz, J. D., Kravchenko, A., 2011. Soil carbon mapping using on-the-go near infrared spectroscopy, topography and aerial photographs. Geoderma 166, 102-110.

[92] Nelson, D. W., Sommers, L. E., 1996. Total carbon, organic carbon, and organic matter. In: Sparks, D. L. (Ed.), Methods of soil analysis—Part 3: Chemical methods. SSSA, Madison, Wis., pp. 961-1010.

[93] NIOSH, 1998. NIOSHmethod 7702: Lead by field portable XRF. Available online at, http://www.caslab.com/Test-Method-7702/ (verified 7 Oct. 2014).

[94] Olympus, 2013. Periodic table of detectable elements. Available online at, http://www.olympus-ims.com/en/innovx-xrf-xrd/pdf-brochures/ (verified 7 Oct. 2014).

[95] Oren, R., Ellsworth, D. S., Johnsen, K. H., Phillips, N., Ewers, B. E., Maier, C., Schafer, K. V. R., McCarthy, H., Hendrey, G., McNulty, S. G., Katul, G. G., 2001. Soil fertility limits carbon sequestration by forest ecosystems in a CO2 enriched atmosphere. Nature 411, 469-472.

[96] Parsons, C., Margui Grabulosa, E., Pili, E., Floor, G. H., Roman-Ross, G., Charlet, L., 2013. Quantification of trace arsenic in soils by field-portable X-ray fluorescence spectrometry: considerations for sample preparation and measurement conditions. J. Hazard Mater. 262, 1213-1222.

[97] R Development Core Team, 2008. R: A Language and Environment for Statistical Computing. R Foundation for Statistical Computing, Vienna, Austria (Available online at http://www.cran.r-project.org. (verified 18 Jul. 2014)).

[98] Reeves, D. W., 1997. The role of soil organic matter in maintaining soil quality in continuous cropping systems. Soil Tillage Res. 43, 131-167.

[99] Reeves III, J., McCarty, G., Mimmo, T., 2002. The potential of diffuse reflectance spectroscopy for the determination of carbon inventories in soils. Environ. Pollut. 116 (Supplement 1), S277-S284.

[100] Rossel, R. A. V., Behrens, T., 2010. Using data mining to model and interpret soil diffuse reflectance spectra. Geoderma 158, 46-54.

[101] Sankey, J. B., Brown, D. J., Bernard, M. L., Lawrence, R. L., 2008. Comparing local vs. global visible and near-infrared (VisNIR) diffuse reflectance spectroscopy (DRS) calibrations for the prediction of soil clay, organic C and inorganic C. Geoderma 148, 149-158.

[102] Sarkhot, D. V., Grunwald, S., Ge, Y., Morgan, C. L. S., 2011. Comparison and detection of total and available soil carbon fractions using visible/near infrared diffuse reflectance spectroscopy. Geoderma 164, 22-32.

[103] Selige, T., Bohner, J., Schmidhalter, U., 2006. High resolution topsoil mapping using hyperspectral image and field data in multivariate regression modeling procedures. Geoderma 136, 235-244.

[104] Sharma, A., Weindorf, D. C., Man, T., Aldabaa, A. A. A., Chakraborty, S., 2014a. Characterizing soils via portable X-ray fluorescence spectrometer: 3. Soil reaction (pH). Geoderma 232-234, 141-147.

[105] Sharma, A., Weindorf, D. C., Wang, D., 2014b. Characterization of soils via portable X-ray fluorescence spectrometer: 4. Cation exchange capacity (CEC). Geoderma 239-240, 130-134.

[106] Soil Survey Staff, 2014b. Kellogg soil survey laboratory methods manual. Soil survey investigations report No. 42, Version 5.0. USDA-NRCS, Lincoln, Nebr.

[107] Song, Y., Li, F., Yang, Z., Ayoko, G. A., Frost, R. L., Ji, J., 2012. Diffuse reflectance spectroscopy for monitoring potentially toxic elements in the agricultural soils of Changjiang River Delta, China. Appl. Clay Sci. 64, 75-83.

[108] Stenberg, B., Viscarra Rossel, R. A., Mouazen, A. M., Wetterlind, J., 2010. Chapter five—visible and near infrared spectroscopy in soil science. In: Sparks, D. L. (Ed.), Advances in Agronomy. Academic Press, pp. 163-215.

[109] Stevens, A., Udelhoven, T., Denis, A., Tychon, B., Lioy, R., Hoffmann, L., van Wesemael, B., 2010. Measuring soil organic carbon in croplands at regional scale using airborne imaging spectroscopy. Geoderma 158, 32-45.

[110] Swanhart, S., Weindorf, D. C., Chakraborty, S., Bakr, N., Zhu, Y., Nelson, C., Shook, K., Acree, A., 2015. Measuring soil salinity via portable X-ray fluorescence spectrometry. Soil Sci. (Accepted; in press 12.5.14).

[111] Terhoeven-Urselmans, T., Schmidt, H., Georg Joergensen, R., Ludwig, B., 2008. Usefulness of near-infrared spectroscopy to determine biological and chemical soil properties: importance of sample pre-treatment. Soil Biol. Biochem. 40 (5), 1178-1188.

[112] Ulmanu, M., Anger, I., Gament, E., Mihalache, M., Plopeanu, G., Ilie, L., 2011. Rapid determination of some heavy metals in soil using an x-ray fluorescence portable instrument. Res. J. Agric. Sci. 43, 235-241.

[113] USEPA, 2007. Method 6200: Field Portable X-ray fluorescence Spectrometry for the Determination of Elemental Concentrations in Soil and Sediment. Available online at, http://www.epa.gov/osw/hazard/testmethods/sw846/pdfs/6200.pdf (verified 7 Oct. 2014).

[114] Vasques, G. M., Grunwald, S., Sickman, J. O., 2008. Comparison of multivariate methods for inferential modeling of soil carbon using visible/near-infrared spectra. Geoderma 146, 14-25.

[115] Vasques, G. M., Grunwald, S., Sickman, J. O., 2009. Modeling of soil organic carbon fractions using visible-near-infrared spectroscopy. Soil Sci. Soc. Am. J. 73, 176-184.

[116] Wang, K., Zhang, C., Li, W., 2013a. Predictive mapping of soil total nitrogen at a regional scale: a comparison between geographically weighted regression and cokriging. Appl. Geogr. 42, 73-85.

[117] Wang, S., Li, W., Li, J., Liu, X., 2013b. Prediction of soil texture using FT-NIR spectroscopy and PXRF spectrometry with data fusion. Soil Sci. 178, 626-638.

[118] Weindorf, D. C., Zhu, Y., Ferrell, R., Rolong, N., Barnett, T., Allen, B. L., Herrero, J., Hudnall, W., 2009. Evaluation of portable X-ray fluorescence for gypsum quantification in soils. Soil Sci. 174, 556-562.

[119] Weindorf, D. C., Zhu, Y., Chakraborty, S., Bakr, N., Huang, B., 2012a. Use of portable X-ray fluorescence spectrometry for environmental quality assessment of peri-urban agriculture. Environ. Monit. Assess. 184, 217-227.

[120] Weindorf, D. C., Zhu, Y., Haggard, B., Lofton, J., Chakraborty, S., Bakr, N., Zhang, W., Weindorf, W. C., Legoria, M., 2012b. Enhanced pedon horizonation using portable Xray fluorescence spectrometry. Soil Sci. Soc. Am. J. 76, 522-531.

[121] Weindorf, D. C., Zhu, Y., McDaniel, P., Valerio, M., Lynn, L., Michaelson, G., Clark, M., Ping, C. L., 2012c. Characterizing soils via portable x-ray fluorescence spectrometer: 2. Spodic and albic horizons. Geoderma 189-190, 268-277.

[122] Weindorf, D. C., Paulette, L., Man, T., 2013b. In-situ assessment of metal contamination via portable X-ray fluorescence spectroscopy: Zlatna, Romania. Environ. Pollut. 182, 92-100.

[123] Wiedenbeck, M., 2013. Field-portable XRF: a geochemist's dream? Elements 9, 7-8.

[124] Zhao, Y., Xia, X. H., Yang, Z. F., Xia, N., 2011. Temporal and spatial variations of nutrients in Baiyangdian Lake, North China. J. Environ. Inf. 17, 102-108.

[125] Zhu, Y., Weindorf, D. C., 2009. Determination of soil calcium using field portable x-ray fluorescence. Soil Sci. 174, 151-155.

[126] Zhu, Y., Weindorf, D. C., Chakraborty, S., Haggard, B., Johnson, S., Bakr, N., 2010. Characterizing surface soil water with field portable diffuse reflectance spectroscopy. J. Hydrol. 391, 133-140.

[127] Adekambi, E. O., 1989. Petroleum Hydrocarbon Pollution in Nigerian Waters and Sediments Around Lagos and Niger Delta Areas of Nigeria. (PhD thesis). University of Ibadan, Ibadan, Nigeria.

[128] Adeniyi, A. A., Afolabi, J. A., 2002. Determination of total petroleum hydrocarbons and heavy metals in soils within the vicinity of facilities handling refined petroleum products in Lagos metropolis. Environ. Int. 28, 79-82.

[129] Albers, P. H., 1995. Petroleum and individual polycyclic aromatic hydrocarbons. In: Haffman, D. T., Rattner, B. A., Burton, G. A., Cairns, J. (Eds.), Handbook of Ecotoxicology. Lewis, London, pp. 330-355.

[130] Balabin, R. M., Safieva, R. Z., 2007. Capabilities of near infrared spectroscopy for the determination of petroleum macromolecule content in aromatic solutions. J. Near Infrared Spectrosc. 15, 343-349.

[131] Bellon-Maurel, V., Fernandez-Ahumada, E., Palagos, B., Roger, J. M., McBratney, A., 2010. Critical reviews of chemometric indicators commonly used for assessing the quality of the prediction of soil attributes by NIR spectroscopy. Trends Anal. Chem. 29, 1073-1081.

[132] Brevik, E. C., Burgess, L. C. (Eds.), 2013. Soils and Human Health. Taylor Francis Press, Boca Raton, Fla.

[133] Camilli, R., Reddy, C. M., Yoerger, D. R., Van Mooy, B. A. S., Jakuba, M. V., Kinsey, J. C., McIntyre, C. P., Silva, S. P., Maloney, J. P., 2010. Tracking hydrocarbon plume transport and biodegradation at Deepwater Horizon. Science 330, 201-204.

[134] Chakraborty, S., Weindorf, D. C., Morgan, C. L. S., Ge, Y., Galbraith, J., Li, B., Kahlon, C. S., 2010. Rapid identification of oil contaminated soils using visible near-infrared diffuse reflectance spectroscopy. J. Environ. Qual. 39, 1378-1387.

[135] Chakraborty, S., Weindorf, D. C., Zhu, Y., Li, B., Morgan, C. L. S., Ge, Y., Galbraith, J., 2012b. Assessing spatial variability of soil petroleum contamination using visible near infrared diffuse reflectance spectroscopy. J. Environ. Monit. 14, 2886-2892.

[136] Chakraborty. S., et al./Science of the Total Environment 514 (2015) 399-408 407

[137] Christy, C. D., 2008. Real-time measurement of soil attributes using on-the-go near infrared reflectance spectroscopy. Comput. Electron. Agric. 61, 10-19.

[138] Clark, R. N., King, T. V. V., Klejwa, M., Swayze, G. A., Vergo, N., 1990. High spectral resolution reflectance spectroscopy of minerals. J. Geophys. Res. 95 (B8), 12653-12680.

[139] Collins, A. G., 1975. Geochemistry of Oilfield Waters. Elsevier, The Netherlands (508 pp.).

[140] Dent, A., Young, A., 1981. Soil Survey and Land Evaluation. George Allen & Unwin Publ, Boston, Mass.

[141] Forrester, S., Janik, L., McLaughlin, M., 2010. An infrared spectroscopic test for total petroleum hydrocarbon (TPH) contamination in soils. Proceedings of the 19th World Congress of Soil Science, Soil Solutions for a Changing World, Brisbane, Australia, August 1-6, pp. 13-16.

[142] Friedman, J. H., 2001. Greedy function approximation: a gradient boosting machine. Ann. Stat. 29, 1189-1232.

[143] Gauch, H. G., Hwang, J. T. G., Fick, G. W., 2003. Model evaluation by comparison of model based predictions and measured values. Agron. J. 95, 1442-1446.

[144] Gondal, M. A., Hussain, T., Yamani, Z. H., Baig, M. A., 2006. Detection of heavy metals in Arabian crude oil residue using laser induced breakdown spectroscopy. Talanta 69 (5), 1072-1078.

[145] Graham, K. N., 1998. Evaluation of analyticalmethodologies for diesel fuel contaminants in soil. MS thesis. The University of Manitoba, Canada (Unpublished results).

[146] Groudeva, V. I., Groudev, S. N., Doycheva, A. S., 2001. Bioremediation of waters contaminated with crude oil and toxic heavy metals. Int. J. Miner. Process. 62, 293-299.

[147] Grujic, S., Ristic, M., Lausevic, M., 2004. Heavy metals in petroleum-contaminated surface soils in Serbia. Ann. Chim. 94 (12), 961-970.

[148] Guyon, I., Weston, J., Barnhill, S., Vapnik, V., 2002. Gene selection for cancer classification using SVM. Mach. Learn. 46, 389-422.

[149] Hewari, J., Beaulie, C., Oullete, D., Pontbriand, Y., Halsaz, A. M., Vanata, H., 1995. Determination of petroleum hydrocarbons in soil: SFE versus Soxhlet andwater effect on recovery. Int. J. Environ. Anal. Chem. 60, 123-137.

[150] Hoerig, B., Kuehn, F., Oschuetz, F., Lehmann, F., 2001. HyMap hyperspectral remote sensing to detect hydrocarbons. Int. J. Remote Sens. 8, 1413-1422.

[151] Kelly, J. J., Tate, R. L., 1998. Effects of heavy metals contamination and remediation on soil microbial communities in the vicinity of a Zn smelter. J. Environ. Qual. 27, 609-617.

[152] Kusumo, B. H., Hedley, C. B., Hedley, M. J., Hueni, A., Tuohy, M. P., Arnold, G. C., 2008. The use of diffuse reflectance spectroscopy for in situ carbon and nitrogen analysis of pastoral soils. Aust. J. Soil Res. 46, 623-635.

[153] Malley, D. F., Hunter, K. N., BarrieWebster, G. R., 1999. Analysis of diesel fuel contamination in soils by near-infrared reflectance spectrometry and solid phase microextraction-gas chromatography. J. Soil Contam. 8 (4), 481-489.

[154] Massoud, M. S., Al-Abdali, F., Al-Ghadban, A. N., Al-Sarawi, M., 1996. Bottom sediments of the Arabian Gulf: II. TPH and TOC contents as indicators of oil pollution and implications for the effect and fate of the Kuwait oil slick. Environ. Pollut. 93, 27-284.

[155] Mullins, O. C., Mitra-Kirtley, S., Zhu, Y., 1992. The electronic absorption edge of petroleum. Appl. Spectrosc. 46, 1405-1411.

[156] Okparanma, R. N., Coulon, F., Mouazen, A. M., 2014. Analysis of petroleum-contaminated soils by diffuse reflectance spectroscopy and sequential ultrasonic solvent extraction-gas chromatography. Environ. Pollut. 184, 298-305.

[157] Onianwa, P. C., 1995. Petroleum hydrocarbon pollution of urban top soil in Ibadan City, Nigeria. Environ. Int. 21, 341-343.

[158] Chukwuma, C. S., 1996. Evaluating baseline data for trace elements pH, organic matter content and bulk density in agricultural soils in Nigeria. Water Air Soil Pollut. 86, 13-34.

[159] Osborne, B. G., Fearn, T., Hindle, P. H., 1993. Practical NIR Spectroscopy with Applications in Food and Beverage Analysis. 2nd ed. Longman Group UK Limited, England.

[160] Oyedeji, A. A., Adebiyi, A. O., Omotoyinbo, M. A., Ogunkunle, C. O., 2012. Effect of crude oil-contaminated soil on germination and growth performance of *Abelmoschus esculentus* L. Moench—a widely cultivated vegetable crop in Nigeria. Am. J. Plant Sci. 3, 1451-1454.

[161] Paulette, L., Man, T., Weindorf, D. C., Person, T., 2015. Rapid assessment of soil and contaminant variability via portable X-ray fluorescence spectroscopy: Coma Mica, Romania. Geoderma 243-244, 130-140.

[162] Schwartz, G., Ben-Dor, E., Eshel, G., 2012. Quantitative analysis of total petroleum hydrocarbons in soils: comparison between reflectance spectroscopy and solvent extraction by 3 certified laboratories. Appl. Environ. Soil Sci. 2012, 1-11.

[163] Smith, L. C., Smith, L. M., Ashcroft, P. A., 2011. Analysis of environmental and economic damages from British Petroleum's Deepwater Horizon oil spill. Albany Law Rev. 74 (1), 563-585.

[164] Vasques, G. M., Grunwald, S., Harris, W. G., 2010. Spectroscopic models of soil organic carbon in Florida, USA. J. Environ. Qual. 39, 923-934.

[165] Wang, D., Chakraborty, S., Weindorf, D. C., Li, B., Sharma, A., Paul, S., Ali, M. N., 2015. Synthesized use of VisNIR DRS and PXRF for soil characterization: Total carbon and total nitrogen. Geoderma 243-244, 157-167.

[166] Weindorf, D. C., Bakr, N., Zhu, Y., 2014. Advances in portable X-ray fluorescence (PXRF) for environmental, pedological, and agronomic applications. Adv. Agron. 128, 1-45.

[167] Workman Jr., J., Weyer, L., 2008. Practical Guide to Interpretive Near-infrared Spectroscopy. CRC Press, Taylor and Francis Group, Boca Raton, Fla., USA.

The invention claimed is:

1. A computerized method for determining one or more properties of a soil sample comprising the steps of:
   providing a visible near infrared diffuse reflectance (VisNIR) spectroradiometer, a x-ray fluorescence (PXRF) spectrometer, a probe connected to the VisNIR spectroradiometer and the PXRF spectrometer, one or more processors communicably coupled to the VisNIR spectroradiometer and the PXRF spectrometer, and one or more input/output interfaces communicably coupled to the one or more processors;
   scanning the soil sample using the VisNIR spectroradiometer;
   scanning the soil sample using the PXRF spectrometer;
   receiving a diffuse reflectance spectra from the VisNIR spectroradiometer and elemental data from the PXRF spectrometer;
   determining one or more properties of the soil sample using the one or more processors and a predictive model that relates the diffuse reflectance spectra and the elemental data to the one or more properties; and
   providing the one or more properties of the soil sample to the one or more input/output interfaces.

2. The method as recited in claim 1, further comprising the step of receiving a set of multispectral reflectance values related to the soil sample from a remote sensing device, and wherein the predictive model further relates the set of multispectral reflectance values to the one or more properties.

3. The method as recited in claim 2, wherein the remote sensing device comprises a satellite and further comprising the step of extracting the multispectral reflectance values from a satellite imagery using a soil and vegetation based indices.

4. The method as recited in claim 2, wherein the step of receiving the set of multispectral reflectance values related to the soil sample from the remote sensing device comprises the step of retrieving the set of multispectral reflectance values from a memory or a data storage communicably coupled to the one or more processors.

5. The method as recited in claim 1, further comprising the step of reducing dimensionality and qualitative discrimination of the diffuse reflectance data.

6. The method as recited in claim 1, wherein the predictive model uses a partial least squares regression (PLS) multivariate algorithm or a support vector regression (SVR) multivariate algorithm.

7. The method as recited in claim 1, further comprising the step of placing the probe in contact with or proximate to the soil sample.

8. The method as recited in claim 1, further comprising the step of calibrating the predictive model.

9. The method as recited in claim 1, wherein the one or more properties comprise one or more chemical properties of the soil sample, one or more physical properties of the soil sample or a combination thereof.

10. The method as recited in claim 1, wherein the one or more properties of the soil sample comprise a soil salinity and the elemental data comprises a Chlorine % and a Sulfur %.

11. The method as recited in claim 1, wherein the one or more properties of the soil sample comprise textural constituents, soil pH, soil carbon content or clay mineralogy.

12. The method as recited in claim 1, wherein the scanning, receiving, determining and providing steps are performed in situ.

13. The method as recited in claim 1, further comprising the step of determining a geographic location of the soil sample using a space-based satellite navigation system.

14. The method as recited in claim 1, further comprising the step of determining an elevation of the soil sample.

15. The method as recited in claim 1, wherein the one or more input/output interfaces comprise a display, a data storage, a printer or a communications interface.

16. The method as recited in claim 1, wherein the visible near infrared diffuse reflectance (VisNIR) spectroradiometer, the x-ray fluorescence (PXRF) spectrometer, the probe, the one or more processors, and the one or more input/output interfaces are integrated into a portable device.

17. The method as recited in claim 1, wherein the elemental data comprises one or more elements selected a list of elements detectable by the PXRF spectrometer.

18. The method as recited in claim 17, further comprising selecting the one or more elements based on the one or more properties of the soil sample to be determined.

19. The method as recited in claim 1, wherein the diffuse reflectance spectra is a primary predictor and the elemental data is an auxiliary predictor within the predictive model.

20. The method as recited in claim 1, further comprising step of retrieving a set of multispectral reflectance values from a memory or a data storage communicably coupled to the one or more processors, and using the set of multispectral reflectance values in combination with the diffuse reflectance spectra and the elemental data to determine the one or more properties of the soil sample.

21. The method as recited in claim 1, wherein the scanning, receiving, determining and providing steps are performed on site proximate to where the soil sample was taken.

22. An apparatus comprising:
a probe;
a visible near infrared diffuse reflectance (VisNIR) spectroradiometer connected to the probe;
a x-ray fluorescence (PXRF) spectrometer connected to the probe;
one or more processors communicably coupled to the VisNIR spectroradiometer and PXRF spectrometer;
one or more input/output interfaces communicably coupled to the one or more processors; and
the one or more processors scan the soil sample using the VisNIR spectroradiometer, scan the soil sample using the PXRF spectrometer, receive a diffuse reflectance spectra from the VisNIR spectroradiometer and elemental data from the PXRF spectrometer, determine one or more properties of the soil sample using the one or more processors and a predictive model that relates the diffuse reflectance spectra and the elemental data to the one or more properties, and provide the one or more properties of the soil sample to the one or more input/output interfaces.

23. The apparatus as recited in claim 22, wherein the one or more processors further receive a set of multispectral reflectance values related to the soil sample from a remote sensing device, and the predictive model further relates the set of multispectral reflectance values to the one or more properties.

24. The apparatus as recited in claim 23, wherein the remote sensing device comprises a satellite and the one or more processors further extract the multispectral reflectance values from a satellite imagery using a soil and vegetation based indices.

25. The apparatus as recited in claim 23, wherein the one or more processors receive the set of multispectral reflectance values related to the soil sample from the remote sensing device by retrieving the set of multispectral reflectance values from a memory or a data storage communicably coupled to the one or more processors.

26. The apparatus as recited in claim 22, wherein the one or more processors further reduce dimensionality and qualitative discrimination of the diffuse reflectance data.

27. The apparatus as recited in claim 22, wherein the predictive model uses a partial least squares regression (PLS) multivariate algorithm or a support vector regression (SVR) multivariate algorithm.

28. The apparatus as recited in claim 22, wherein the one or more processors further calibrate the predictive model.

29. The apparatus as recited in claim 22, wherein the one or more properties comprise one or more chemical properties of the soil sample, one or more physical properties of the soil sample or a combination thereof.

30. The apparatus as recited in claim 22, wherein the one or more properties of the soil sample comprise a soil salinity and the elemental data comprises a Chlorine % and a Sulfur %.

31. The apparatus as recited in claim 22, wherein the one or more properties of the soil sample comprise textural constituents, soil pH, soil carbon content or clay mineralogy.

32. The apparatus as recited in claim 22, wherein the one or more processors perform the scanning, receiving, determining and providing steps in situ.

33. The apparatus as recited in claim 22, wherein the one or more processors further determine a geographic location of the soil sample using a space-based satellite navigation system.

34. The apparatus as recited in claim 22, wherein the one or more processors further determine an elevation of the soil sample.

35. The apparatus as recited in claim 22, wherein the one or more input/output interfaces comprise a display, a data storage, a printer or a communications interface.

36. The apparatus as recited in claim 22, wherein the apparatus is portable.

37. A computer program embodied on a non-transitory computer readable medium that causes one or more processors to perform the steps of:
scanning a soil sample using a visible near infrared diffuse reflectance (VisNIR) spectroradiometer;
scanning the soil sample using a x-ray fluorescence (PXRF) spectrometer;
receiving a diffuse reflectance spectra from the VisNIR spectroradiometer and an elemental data from the PXRF spectrometer;
determining one or more properties of the soil sample using a predictive model that relates the diffuse reflectance spectra and the elemental data to the one or more properties; and
providing the one or more properties of the soil sample to one or more input/output interfaces.

38. The method as recited in claim 1, wherein the soil sample has a moisture content less than 20%.

* * * * *